United States Patent
Schobben et al.

(10) Patent No.: US 11,110,271 B1
(45) Date of Patent: Sep. 7, 2021

(54) METHOD FOR IMPLANTING A STIMULATOR WITH A FOIL-LIKE ELECTRODE PORTION

(71) Applicant: Salvia BioElectronics B.V., Eindhoven (NL)

(72) Inventors: Daniel Schobben, Eindhoven (NL); Hubert Martens, Eindhoven (NL); Marjolein Schets, Eindhoven (NL); Wim Pollet, Eindhoven (NL)

(73) Assignee: Salvia BioElectronics B.V.

( * ) Notice: Subject to any disclaimer, the term of this patent is extended or adjusted under 35 U.S.C. 154(b) by 0 days.

(21) Appl. No.: 17/079,316

(22) Filed: Oct. 23, 2020

(51) Int. Cl.
*A61N 1/36* (2006.01)
*A61N 1/05* (2006.01)
(Continued)

(52) U.S. Cl.
CPC ....... *A61N 1/0551* (2013.01); *A61M 25/0662* (2013.01); *A61M 25/09041* (2013.01); *A61N 1/36075* (2013.01)

(58) Field of Classification Search
CPC .. A61N 1/0504; A61N 1/0526; A61N 1/0551; A61N 1/36075; A61N 1/0529;
(Continued)

(56) References Cited

U.S. PATENT DOCUMENTS

| 9,480,845 B2 | 11/2016 | Harris |
| 2007/0073356 A1 | 3/2007 | Rooney |

(Continued)

FOREIGN PATENT DOCUMENTS

| WO | 2019200270 A1 | 10/2019 |

OTHER PUBLICATIONS

Hassler, Boretius, Steglitz, Polymers for neural implants, Journal of Polymer Science Part B: Polymer Physics / vol. 49, Iss. 1, Nov. 23, 2010, online, 10.1002/polb.22169.

*Primary Examiner* — Jon Eric C Morales
(74) *Attorney, Agent, or Firm* — Fresh IP PLC; Clifford D. Hyra; Aubrey Y. Chen

(57) ABSTRACT

In general, implantation of neurostimulation systems or device includes subcutaneous or percutaneous placement of at least the electrodes. Preferred are minimally invasive implantation procedures, systems and devices that can reliably operate for extended periods, and systems and devices providing a high degree of comfort for the subject. The implantation specialist may need to address adequate placement of the electrodes with respect to the nerve tissue to be stimulated, and to choose between one or more convenient locations for the elements of the system or device.

Methods are provided comprising forming a first 1250 and second 1260 incision on opposite sides of a target location, and introducing a first introducer sheath 3050a under the skin with a maximum internal transverse cross-section less than the further maximum transverse cross-section 710 of an implantable stimulator. Such a method is advantageous if the maximum transverse cross-section 710 of the further portion is at least 1.2 times greater than the maximum transverse cross-section 730 of the first portion—the dimensions of the implantation tools may be reduced.

A further method is provided wherein the first portion 630 with at least two electrodes 200, 400 is introduced in the skin layers between the nerve tissue 2003 to be stimulated and above or in the aponeurosis layer 2009.

By being implanted deeper and/or more accurately, comfort and/or reliability for the subject may be improved. In addition, the chance that the stimulator is implanted under the nerve tissue is greatly increased.

28 Claims, 27 Drawing Sheets

(51) Int. Cl.
  *A61M 25/09*   (2006.01)
  *A61M 25/06*   (2006.01)
  *A61B 17/34*   (2006.01)
(58) Field of Classification Search
  CPC ........... A61N 1/37514; A61M 5/14276; A61B 5/0006; A61B 5/0031; A61B 5/369; A61B 5/4094
  See application file for complete search history.

(56)     References Cited

U.S. PATENT DOCUMENTS

| | | |
|---|---|---|
| 2010/0057165 A1 | 4/2010 | Moffitt |
| 2011/0093043 A1 | 4/2011 | Torgerson |
| 2016/0166828 A1 | 6/2016 | Yu |
| 2017/0072200 A1 | 3/2017 | Fletcher |
| 2017/0252568 A1 | 9/2017 | Reed |
| 2018/0093096 A1 | 4/2018 | Mashiach |
| 2018/0117332 A1 | 5/2018 | Robinson |
| 2019/0091480 A1* | 3/2019 | Reed ................ A61N 1/37211 |

\* cited by examiner

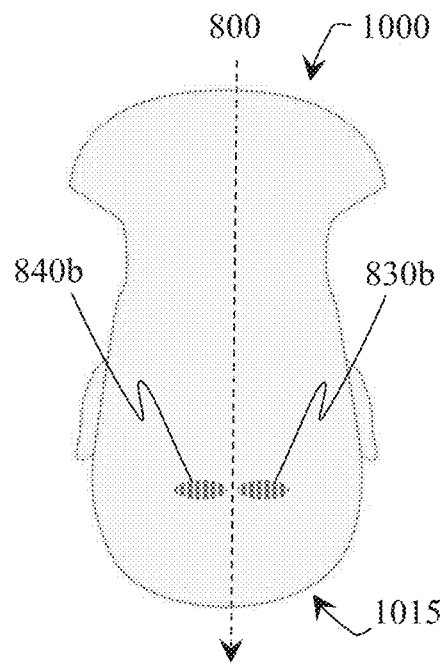
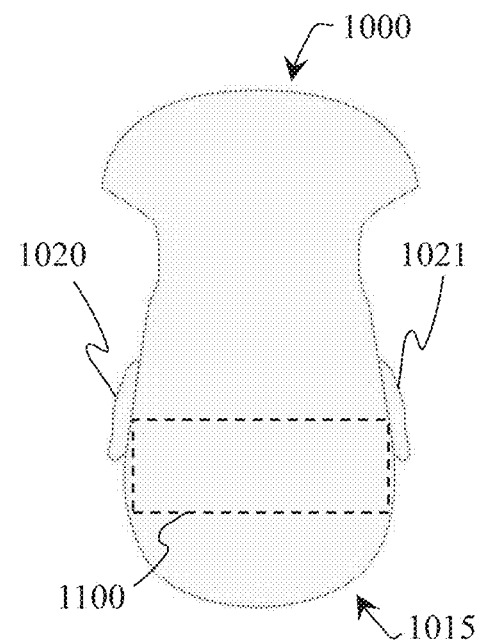
Fig. 8A
Fig. 8B
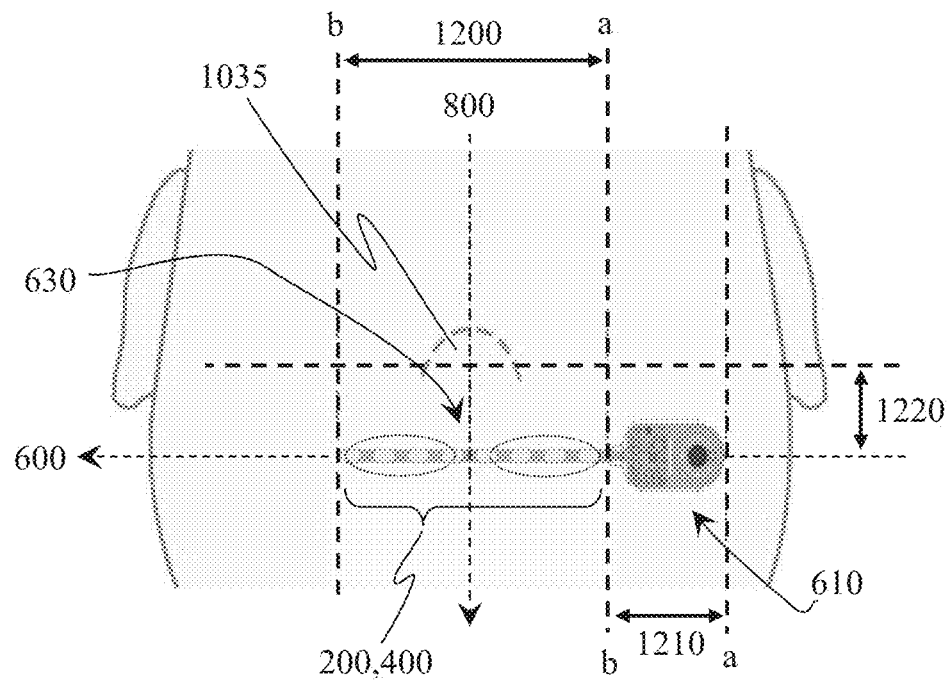
Fig. 8C

METHOD FOR IMPLANTING A STIMULATOR WITH A FOIL-LIKE ELECTRODE PORTION

FIELD OF THE DISCLOSURE

The present application relates generally to methods for implanting a medical device, more particularly an implantable stimulator with a foil-like portion. The implantable stimulator may have a foil-like substrate, and be configured and arranged for providing electrical stimulation to human or animal tissue. In particular, the implantable stimulator may have a conformable foil-like portion comprising at least two electrodes. This application also relates to methods for implanting an implantable stimulator under nerve tissue of a subject.

BACKGROUND

The present application relates to the field of implantable electrical stimulation systems, which may be used to deliver electrical stimulation therapy to subjects to treat a variety of symptoms or conditions such as headaches, lower back pain and incontinence. In many electrical stimulation applications, it is desirable for a stimulator, typically comprising a therapeutic lead (a lead comprises electrodes and electrical wire connections), to provide electrical stimulation to one or more precise locations within a body.

Such systems and devices may be implanted for improving headache disorders, chronic pain of peripheral origin or other disorder in a subject suffering therefrom by electrically modulating neural tissue.

In general, implantation includes subcutaneous or percutaneous placement of at least the electrodes of the neurostimulation system or device. One or more elements of the device may remain located external to be body, being connected wirelessly and/or wired to the rest of the system or device. Preferred are minimally invasive implantation procedures, systems and devices that can reliably operate for extended periods, and systems and devices providing a high degree of comfort for the subject. Incorrect placement may create unexpected and/or unpredictable electrical resistance between one or more electrodes and the underlying tissue. Subcutaneous placement, particularly in bodily regions where the skin is relatively thin, such as the cranium, may affect subject comfort, and can cause irritation of the overlying skin.

The specialist performing the implantation may need to address practical issues which can reduce the degree of satisfaction with the implantation, such as an adequate placement of the electrodes with respect to the nerve tissue to be stimulated, and the availability of one or more convenient locations for the electrode leads, interconnecting wires, any operating electronics/electrical components and any power supplies.

SUMMARY

It is to be understood that both the following summary and the detailed description are exemplary and explanatory and are intended to provide further explanation of the invention as claimed. Neither the summary nor the description that follows is intended to define or limit the scope of the invention to the particular features mentioned in the summary or in the description. Rather, the scope of the invention is defined by the appended claims In certain embodiments, the disclosed embodiments may include one or more of the features described herein.

Products and methods described herein provide methods to implant stimulators that are not symmetrically dimensioned. Additionally, they may be advantageously used with stimulators having a relatively high degree of conformability, which may increase the comfort for the subject. Improved implantation procedures disclosed herein are repeatable and reproducible for a wide range of subjects, while providing a high degree of satisfaction for the subjects A method is provided for implanting an implantable stimulator under nerve tissue of a subject, the implantable stimulator comprising: a substrate, comprising a first surface and a second surface, wherein a thickness of the substrate is defined by the first and second surfaces; and at least two electrodes located along a conformable first portion of the substrate, the thickness of the substrate along the conformable first portion being equal to or less than 0.5 millimeters; the method comprising: identifying a target location for stimulation which in transverse cross-section comprises an outer skin layer, nerve tissue to be stimulated, and an inner aponeurosis layer; forming one or more incisions proximate the target location; introducing the conformable first portion in the skin layers at the target location, whereby the at least two electrodes are disposed under the nerve tissue to be stimulated and above or in the inner aponeurosis layer.

It may be advantageous to introduce the first portion such that the at least two electrodes are disposed in skin layers above or in aponeurosis layer. There are typically fewer blood vessels, so the risk of damage to other anatomical structures may be reduced. In addition, implantation "under" the nerve tissue is simplified for the specialist—in this context, "under" the nerve means a skin depth location between the nerve tissue and the underlying bone tissue. By using a first portion with a greatly reduced thickness, such as 0.5 mm or less, introduction deeper under the skin becomes possible. Additionally or alternatively, comfort for the subject may be improved if the stimulator is located deeper under the skin. By using a conformable first portion, insertion may be made more precisely at the interfaces between skin layers—the risk may be reduced of tissue damage during insertion, and the conformable first portion may more easily follow anatomical curvature. Also, by selecting locations where aponeurosis tissue is present, the risk that muscle tissue is disposed between the stimulator and the nerve tissue to be stimulated is greatly reduced.

An implantation method is provided, wherein the method comprises: introducing the conformable first portion, whereby the at least two electrodes are disposed in the skin layers between subcutaneous fat and the aponeurosis layer. Additionally or alternatively, the method comprises: introducing the first portion, whereby the at least two electrodes are disposed in the skin layers directly adjacent to the aponeurosis layer. Additionally or alternatively, the method comprises: removing one or more skin layers, including an outer skin layer and subcutaneous fat, before introducing the first portion.

Deeper locations within the skin further increase the chance that the first portion is introduced below the nerve. Comfort for the subject may also be improved if the stimulator is located deeper under the skin. Additionally or alternatively, it is relatively straightforward for a specialist to identify the transition between the subcutaneous fat layer and the underlying tissue.

An implantation method is provided, wherein the method comprises: forming an incision proximate an implantation location; and introducing a further portion of the substrate in the skin layers, whereby the further portion is disposed between subcutaneous fat and above or in muscle tissue.

This may allow a more complete implantation of the implantable stimulator, which may reduce infection risk, and may increase the positional stability of the first portion.

Additionally or alternatively, the method comprises: introducing the further portion, whereby the further portion is disposed in the skin layers between subcutaneous fat and a bone layer. Additionally or alternatively, the method comprises: introducing the further portion, whereby the further portion is disposed in the skin layers directly adjacent to the muscle tissue. Additionally or alternatively, the method comprises: removing one or more skin layers, including an outer skin layer and subcutaneous fat, before introducing the further portion.

By implanting deep or below subcutaneous fat, comfort may be improved for the subject as the further portion is covered by more skin layers. It may also be advantageous for the specialist to implant the first portion and further portion at approximately the same depth in the skin.

The methods described may be used to reliably implant below nerve tissue to be stimulated. Additionally, the methods described using one or more introducer sheaths may be used to further improve the under-nerve implantation methods.

Additionally or alternatively, the substrate is longitudinally-extended, further comprising a further portion; the first portion has a first maximum transverse cross-section and the further portion has a further maximum transverse cross-section, the further maximum transverse cross-section being at least 1.2 times greater than the first maximum transverse cross-section; the method comprising: forming a first and second incision on opposite sides of the target location; introducing a first introducer sheath under the skin from the second incision to the first incision, the first introducer sheath having a maximum internal transverse cross-section less than the further maximum transverse cross-section of the substrate; introducing the conformable first portion, comprising the at least two electrodes, into the first introducer sheath from the first incision to the second incision; removing the first introducer sheath, whereby the implantable stimulator extends under the skin from the further portion at the first incision to the conformable first portion at the second incision, whereby the at least two electrodes are arranged to transfer treatment energy to the target location.

By using a first introducer with a minimum internal transverse cross-section greater than the maximum cross-section of the first portion, the first portion may be introduced into the first introducer. It is not necessary to introduce the further portion, so the maximum internal transverse cross-section of the first introducer may be significantly less than the maximum transverse cross-section of the further portion of the stimulator. Using an introducer sheath and two incisions, the stimulator may be implanted at many target locations of the subject. This may be even more advantageous if the first portion is conformable.

Additionally or alternatively, the method comprises: forming a third incision between the first and second incisions; introducing the first introducer sheath under the skin from the second incision to the third incision instead of from the second incision to the first incision; introducing a second introducer sheath under the skin from the third incision to the first incision, the second introducer sheath having a maximum internal transverse cross-section less than the further maximum transverse cross-section of the substrate; introducing the first portion of the implantable stimulator, comprising the at least two electrodes, into the second introducer sheath from the first incision to the third incision position; removing the second introducer sheath; introducing the first portion of the implantable stimulator, comprising the at least two electrodes, into the first introducer sheath from the third incision to the second incision; and removing the first introducer sheath, whereby the implantable stimulator extends under the skin from the further portion at the first incision to the first portion at the second incision.

Using a first and second introducer sheaths and three incisions, the stimulator may be implanted at many target locations in the body of the subject where the first portion and the further portion are to be separated by at least one portion of curved skin. This may be even more advantageous if the first portion is conformable A method is provided for implanting an implantable stimulator, the implantable stimulator comprising: a longitudinally-extended substrate having a conformable first portion and a further portion; at least two electrodes, comprised in the conformable first portion; wherein the first portion has a first maximum transverse cross-section and the further portion has a further maximum transverse cross-section, the further maximum transverse cross-section being at least 1.2 times greater than the first maximum transverse cross-section; the method comprising: identifying a target location of a subject for stimulation; forming a first and second incision on opposite sides of the target location; introducing a first introducer sheath under the skin from the second incision to the first incision, the first introducer sheath having a maximum internal transverse cross-section less than the further maximum transverse cross-section of the substrate; introducing the conformable first portion, comprising the at least two electrodes, into the first introducer sheath from the first incision to the second incision; removing the first introducer sheath, whereby the implantable stimulator extends under the skin from the further portion at the first incision to the conformable first portion at the second incision whereby the at least two electrodes are arranged to transfer treatment energy to the target location.

By using a first introducer with a minimum internal transverse cross-section greater than the maximum cross-section of the first portion, the first portion may be introduced into the first introducer. It is not necessary to introduce the further portion, so the maximum internal transverse cross-section of the first introducer may be significantly less than the maximum transverse cross-section of the further portion of the stimulator. Using an introducer sheath and two incisions, the stimulator may be implanted at many target locations of the subject. This may be even more advantageous if the first portion is conformable.

Additionally or alternatively, the method comprises: introducing a guide wire under the skin between the first and second incisions, the guide wire having a maximum transverse cross-section less than the minimum internal transverse cross-section of the introducer sheath; introducing the first introducer sheath over the guide wire under the skin from the second incision to the first incision; and removing the guidewire, whereby the first introducer sheath extends under the skin from the second incision to the first incision.

By using a guide wire dimensioned to accept the first introducer, it may speed up the procedure. Additionally or alternatively, it may reduce unwanted tissue damage during insertion of the first introducer. Additionally or alternatively, it may allow a smaller dimensioned introducer to be used as it does not need to be as rigid.

Additionally or alternatively, the method comprises: inserting the tip of an guidewire introducer needle into the first incision and further inserting the guidewire introducer needle under the skin until the tip emerges from the second incision, the guidewire introducer needle having a minimum internal transverse cross-section greater than the maximum transverse cross-section of the guide wire; inserting the guide wire through the guidewire introducer needle; and removing the guidewire introducer needle from under the skin to leave the guide wire extending under the skin through the first incision to the second incision.

By using a guidewire introducer needle dimensioned to accept the guide wire, it may further speed up the procedure. Additionally or alternatively, it may reduce unwanted tissue damage during insertion of the guide wire. Additionally or alternatively, it may allow a smaller dimensioned guide wire to be used as it does not need to be as rigid.

Additionally or alternatively, the method comprises: forming a skin pocket around the first incision, arranged to accept the further portion of the implantable stimulator; and introducing the further portion of the implantable stimulator into the skin pocket at the first incision.

Conventionally, implants are implanted just under the outer layer of skin. However, by implanting deep or below subcutaneous fat, comfort may be improved for the subject as the further portion is covered by more skin layers. It may also be advantageous for the specialist to implant the first portion and further portion at approximately the same depth in the skin.

Additionally or alternatively, the method comprises: implanting at a target location is under nerve tissue of the subject.

It is advantageous to implant the stimulator with one or more electrodes under the nerve to be stimulated. By being implanted deeper, comfort for the subject may be improved. In addition, if it the chance that the stimulator is implanted under the nerve tissue is relatively high, it may allow a first portion with electrodes on only one surface (either the first or second surface) to be more reliably used.

Additionally or alternatively, the substrate comprises a first and second surface defining a thickness of the substrate, the thickness of the substrate along the conformable first portion being 0.5 millimeter or less.

By using a first portion with a greatly reduced thickness, such as 0.5 mm or less, introduction deeper under the skin becomes possible. Additionally or alternatively, comfort for the subject may be improved if the stimulator is located deeper under the skin. By using a conformable first portion, insertion may be made more precisely at the interfaces between skin layers—the risk may be reduced of tissue damage during insertion, and the conformable first portion may more easily follow anatomical curvature.

Additionally or alternatively, the method comprises: forming a third incision between the first and second incisions; introducing the first introducer sheath under the skin from the second incision to the third incision instead of from the second incision to the first incision; introducing a second introducer sheath under the skin from the third incision to the first incision, the second introducer sheath having a maximum internal transverse cross-section less than the further maximum transverse cross-section of the substrate; introducing the first portion of the implantable stimulator, comprising the at least two electrodes, into the second introducer sheath from the first incision to the third incision position; removing the second introducer sheath; introducing the first portion of the implantable stimulator, comprising the at least two electrodes, into the first introducer sheath from the third incision to the second incision; and removing the first introducer sheath, whereby the implantable stimulator extends under the skin from the further portion at the first incision to the first portion at the second incision.

By using a first and second introducer with a minimum internal transverse cross-section greater than the maximum cross-section of the first portion, the first portion may be introduced into the first and second introducer. It is not necessary to introduce the further portion, so the maximum internal transverse cross-section of the first introducer may be significantly less than the maximum transverse cross-section of the further portion of the stimulator. Using a first and second introducer sheaths and three incisions, the stimulator may be implanted at many target locations in the body of the subject where the first portion and the further portion are to be separated by at least one portion of curved skin. This may be even more advantageous if the first portion is conformable.

The methods described using one or more introducer sheaths may be used to reliably position a stimulation device at an implantation site sufficiently close to the nerve to be stimulated. Additionally, the methods described for reliably implanting under the nerve may be used to further improve the introducer sheath methods.

Additionally or alternatively, wherein the target location identified for stimulation comprises, in transverse cross-section, an outer skin layer, nerve tissue to be stimulated, and an inner aponeurosis layer; the method comprises: introducing the conformable first portion in the skin layers at the target location, whereby the at least two electrodes are disposed under the nerve tissue to be stimulated and above or in the aponeurosis layer.

It may be advantageous to implant above or in aponeurosis layer. There are typically fewer blood vessels, so the risk of damage to other anatomical structures may be reduced.

For performing the implantation using the one or more introducers, a kit of parts is advantageously provided comprising: a stimulator comprising: a longitudinally-extended substrate having a conformable first portion and a further portion; at least two electrodes, comprised in the conformable first portion; wherein the first portion has a first maximum transverse cross-section and the further portion has a further maximum transverse cross-section, the further maximum transverse cross-section being at least 1.2 times greater than the first maximum transverse cross-section; a first introducer sheath having a maximum internal transverse cross-section less than the further maximum transverse cross-section of the substrate; a guide wire having a maximum transverse cross-section less than the minimum internal transverse cross-section of the introducer sheath; and a guidewire introducer needle having a minimum internal transverse cross-section greater than the maximum transverse cross-section of the guide wire.

Additionally the kit of parts may further comprise: a second introducer sheath having: a maximum internal transverse cross-section less than the further maximum transverse cross-section of the substrate; and a minimum internal transverse cross-section greater than the maximum transverse cross-section of the guide wire.

Stimulators implanted according to the methods described in this application may be advantageously used for stimulating: one or more nerves, one or more muscles, one or more organs, spinal cord tissue, brain tissue, one or more cortical surface regions, one or more sulci, and any combination thereof.

Stimulators implanted according to the methods described in this application may be advantageously used for treatment of: headaches, primary headaches, incontinence, occipital neuralgia, sleep apnea, hypertension, gastro-esophageal reflux disease, an inflammatory disease, limb pain, leg pain, back pain, lower back pain, phantom pain, chronic pain, epilepsy, an overactive bladder, poststroke pain, obesity, an autoimmune disorder, rheumatoid arthritis, inflammatory bowel disease, Crohn's disease, and any combination thereof.

These and further and other objects and features of the invention are apparent in the disclosure, which includes the above and ongoing written specification, with the drawings.

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art. The invention will be more particularly described in conjunction with the following drawings wherein.

DETAILED DESCRIPTION

Figure 1A:
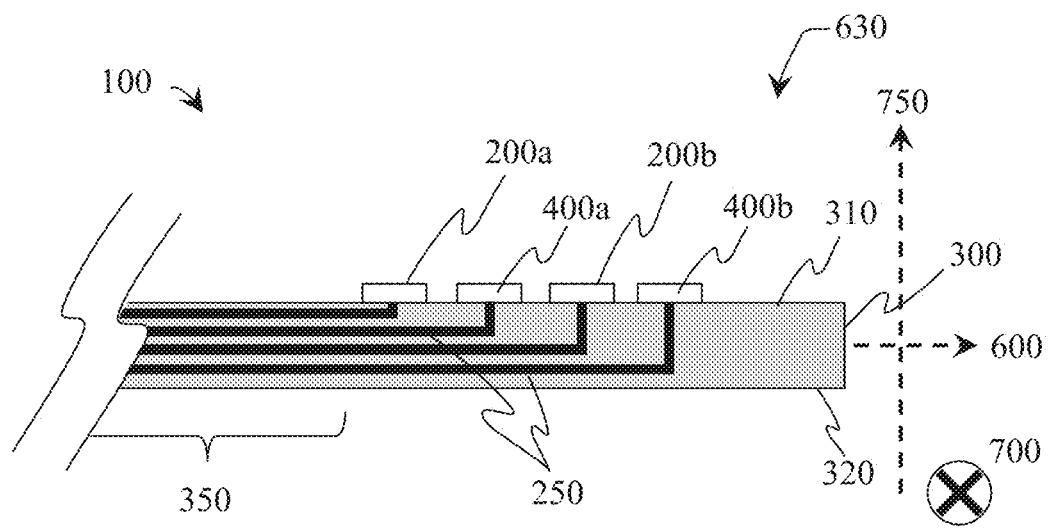
FIGS. 1A, 1B, 1C, 1D and 1E depict examples of an implantable stimulator.

An implantable stimulator, and methods for implanting a stimulator will now be disclosed in terms of various exemplary embodiments. This specification discloses one or more embodiments that incorporate features of the invention. The embodiment(s) described, and references in the specification to "one embodiment", "an embodiment", "an example embodiment", etc., indicate that the embodiment(s) described may include a particular feature, structure, or characteristic. Such phrases are not necessarily referring to the same embodiment. When a particular feature, structure, or characteristic is described in connection with an embodiment, persons skilled in the art may effect such feature, structure, or characteristic in connection with other embodiments whether or not explicitly described.

In the several figures, like reference numerals may be used for like elements having like functions even in different drawings. The embodiments described, and their detailed construction and elements, are merely provided to assist in a comprehensive understanding of the invention. Thus, it is apparent that the present invention can be carried out in a variety of ways, and does not require any of the specific features described herein. Also, well-known functions or constructions are not described in detail since they would obscure the invention with unnecessary detail. Any signal arrows in the drawings/figures should be considered only as exemplary, and not limiting, unless otherwise specifically noted.

The description is not to be taken in a limiting sense, but is made merely for the purpose of illustrating the general principles of the invention, since the scope of the invention is best defined by the appended claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items. As used herein, "at least one of A, B, and C" indicates A or B or C or any combination thereof. As used herein, the singular form of a word includes the plural, and vice versa, unless the context clearly dictates otherwise. Thus, the references "a", "an", and "the" are generally inclusive of the plurals of the respective terms.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

As used herein, ranges are used herein in shorthand, so as to avoid having to list and describe each and every value within the range. Any appropriate value within the range can be selected, where appropriate, as the upper value, lower value, or the terminus of the range.

The words "comprise", "comprises", and "comprising" are to be interpreted inclusively rather than exclusively. Likewise the terms "include", "including" and "or" should all be construed to be inclusive, unless such a construction is clearly prohibited from the context. The terms "comprising" or "including" are intended to include embodiments encompassed by the terms "consisting essentially of" and "consisting of". Similarly, the term "consisting essentially of" is intended to include embodiments encompassed by the term "consisting of". Although having distinct meanings, the terms "comprising", "having", "containing' and "consisting of" may be replaced with one another throughout the description of the invention.

"About" means a referenced numeric indication plus or minus 10% of that referenced numeric indication. For example, the term "about 4" would include a range of 3.6 to 4.4. All numbers expressing quantities of ingredients, reaction conditions, and so forth used in the specification are to be understood as being modified in all instances by the term "about." Accordingly, unless indicated to the contrary, the numerical parameters set forth herein are approximations that can vary depending upon the desired properties sought to be obtained. At the very least, and not as an attempt to limit the application of the doctrine of equivalents to the scope of any claims, each numerical parameter should be construed in light of the number of significant digits and ordinary rounding approaches.

Wherever the phrase "for example," "such as," "including" and the like are used herein, the phrase "and without limitation" is understood to follow unless explicitly stated otherwise.

"Typically" or "optionally" means that the subsequently described event or circumstance may or may not occur, and that the description includes instances where said event or circumstance occurs and instances where it does not.

Figure 1B:
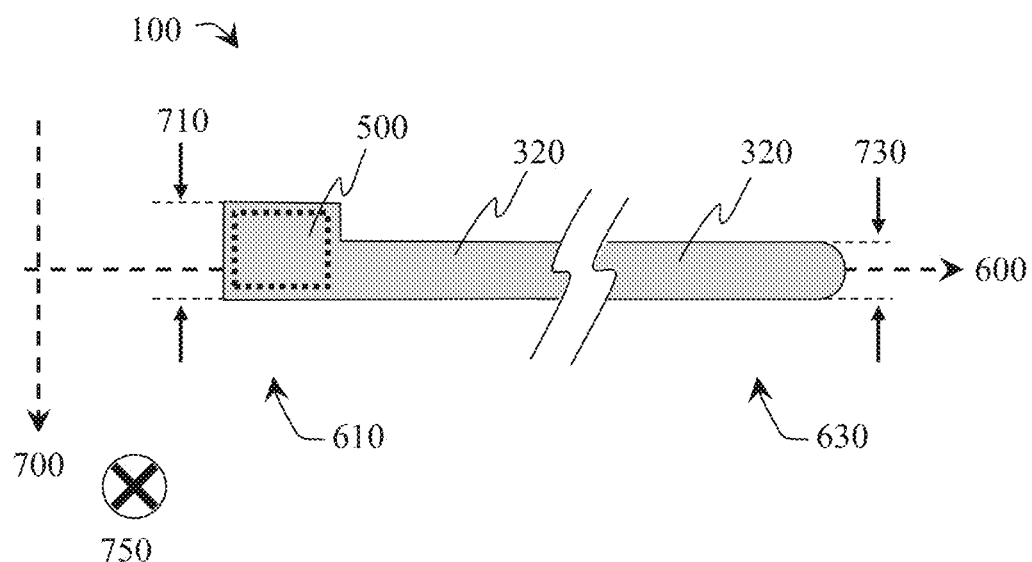
Figure 1C:
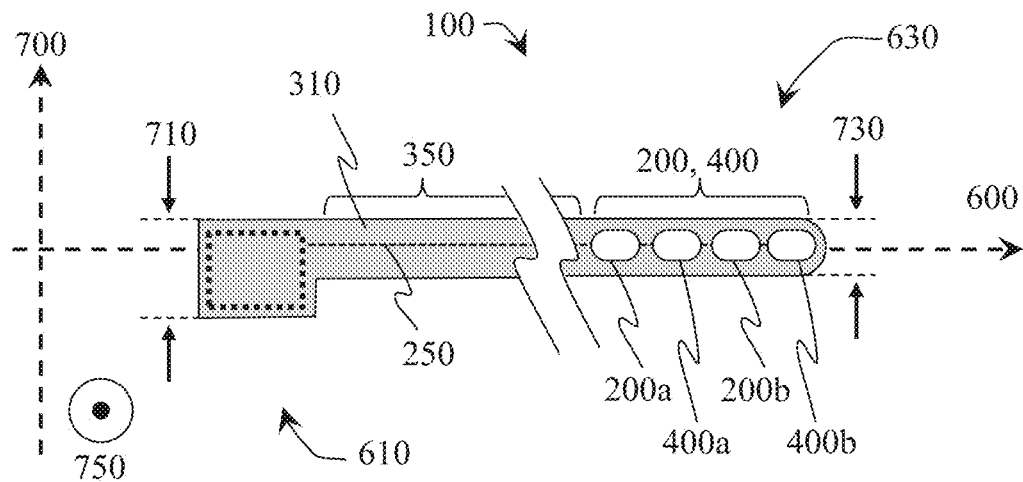

FIGS. 1A, 1B & 1C depict longitudinal cross-sections through a first embodiment 100 of an implantable stimulator comprising:

an electrode array 200, 400, comprised in a first portion 630, with at least two electrodes 200, 400. Optionally, the first portion 630 may be conformable.

In this example, one or more electrodes are provided of a first 200a, 200b type and one or more electrodes of a second type 400a, 400b. The electrodes 200, 400 are comprised in the first 310 or second 320 surface, and each is configurable for transferring treatment energy, in use, to (as a stimulation electrode) and/or from (as a return electrode) human or animal tissue. In this context, an array may be considered a systematic arrangement of two or more electrodes 200a, 200b, 400a, 400b. 1D, 2D or 3D arrays may be provided. Optionally, they may be arranged in rows and/or columns. In this example, the first portion 630 comprises a 1D array with two electrodes of the first type 200a, 200b and two electrodes of the second type 400a, 400b. However, as described below, any number and type of electrodes may be used.

The implantable stimulator 100 further comprises:

a further portion 610 comprising one or more electrical and/or electronic components. In this example, the further portion 610 comprises a pulse generator 500 (only depicted in FIGS. 1B and 1C), located along the further portion 610, for generating one or more electrical treatment stimulation pulses. Additionally or alternatively, the further portion 610 may comprise one or more pulse energy receiver. The further portion 610 may also be described as a proximal end; and a substrate 300 extending longitudinally from the further portion 610 to a first portion 630 along a longitudinal axis 600.

Optionally, the substrate (300) may comprise a conformable foil-like portion, as explained below. Additionally or alternatively, the substrate 300 may comprise two or more adjacent polymeric substrate layers The substrate 300 comprises a first 310 and second 320 surface, defining one or more thicknesses. Optionally, the surfaces may be substantially planar. Additionally or alternatively, the pulse energy receiver or pulse generator may be comprised between the first and second surfaces.

The implantable stimulator 100 also comprises:

one or more electrical interconnections 250, between the further portion 610 and the first 200a, 200b and the second 400a, 400b electrodes, for transferring electrical energy as one or more electrical treatment stimulation pulses to the first electrode 200a, 200b and/or the second electrodes 400a, 400b. The one or more electrical interconnections 250 are comprised between the first surface 310 and the second 320 surfaces. In other words, a plurality of electrical interconnections 250 are comprised between the first 310 and second 320 surfaces using metallization.

If the separation between the further portion 610 and the first portion 630 is relatively large, a portion 350 of the substrate may be provided which comprises no stimulation electrodes. The length of this portion 350 may be configured and arranged to allow the first portion 630 and the further portion 610 to be located at different positions on and/or in the body.

In this disclosure, the conformability of the at least two electrodes 200, 400 is determined to a high degree by the one or more of the following:

the conformability of the substrate 300 proximate the electrodes 200, 400;

the arrangement and positions of the electrodes 200, 400;

the materials and dimensions (or extent) of the materials comprised in the electrodes 200, 400;

the arrangement and positions of the one or more interconnections 250 proximate the electrodes 200, 400; and the materials and dimensions (or extent) of the materials comprised in the interconnections 200, 400.

By suitable configuration, arrangement and optimization, an implantable portion with at least two electrodes 200, 400 may be provided which is further configured and arranged to be foil-like (or film-like) and highly conformable.

As depicted, the substrate 300 is preferably elongated along the longitudinal axis 600, having a tape-like shape, allowing the further portion 610 to be disposed further away from the position of the electrodes 200, 400. This provides a high degree of flexibility if the distal and further portions of the stimulator 100 have different transverse cross-sections.

If the substrate 300 is arranged substantially planar (for example, by allowing the substrate 300 to conform to a planar surface), the first 310 and second 320 surfaces are disposed along substantially parallel transverse planes 600, 700. As depicted in FIG. 1A and FIG. 1C, the first surface 310 lies in a plane comprising the longitudinal axis 600 and a first transverse axis 700—the first transverse axis 700 is substantially perpendicular to the longitudinal axis 600. As depicted in FIG. 1A, the plane of the first surface 310 is substantially perpendicular to the plane of the cross-section drawing (substantially perpendicular to the surface of the paper). As depicted in FIG. 1A and FIG. 1B, the second surface 320 lies in a plane comprising the longitudinal axis 600 and the first transverse axis 700. As depicted in FIG. 1A, the plane of the first surface 310 is substantially perpendicular to the plane of the cross-section drawing (substantially perpendicular to the surface of the paper).

If the substrate 300 is conformable and foil-like, the substrate 300 typically has a maximum thickness of 0.5 millimeter or less, proximate the first 200a, 200b and second 400a, 400b electrodes.

As depicted, a thickness may be considered as a perpendicular distance between corresponding points on the first 310 and second surfaces 320. This is preferably determined when the substrate 300 conforms to a planar surface.

As depicted in FIG. 1A, the substrate 300 thickness is an extent along a second transverse axis 750—this second transverse axis 750 is substantially perpendicular to both the longitudinal axis 600 and the first transverse axis 700—it lies in the plane of the drawing (along the surface of the paper) as depicted. The first surface 310 is depicted as an upper surface and the second surface 320 is depicted as a lower surface. The extent along the second transverse axis 750 (thickness) may also be described as a dimension of a cross-section in the transverse plane 700, 750.

The thickness may therefore be determined by a perpendicular distance along the second transverse axis 750 between corresponding points on the first 310 and second surfaces 320.

The maximum thickness of a conformable and/or foil-like substrate 300 along the first portion 630 is preferably 0.5 mm or less, preferably 0.3 millimeters or less, even more preferably 0.2 millimeters or less, yet more preferably 0.1 millimeters or less.

In general, the lower the maximum thickness (in other words, the thinner the substrate), the higher the degree of conformance.

Additionally or alternatively, the maximum thickness may be determined proximate the first 200*a*, 200*b* and second 400*a*, 400*b* electrodes.

To clarify the differences between the different views depicted, the axes are given nominal directions:

- the longitudinal axis 600 extends from the further portion 610 (not depicted in FIG. 1A, but depicted in FIGS. 1B and 1C) on the left, to the first portion 630, depicted on the right of the page;
- the first transverse axis 700 extends into the page as depicted in FIG. 1A; and
- the second transverse axis 750 extends from bottom to top as depicted in FIG. 1A.

The substrate 300 may be configured and arranged as a multilayer, comprising two or more adjacent polymeric substrate layers having the first 310 and second 320 surface. The one or more electrical interconnections 250 are also comprised between the first 310 and second 320 surfaces. However, it is not necessary that the two or more polymeric layers and/or interconnections have similar extents along the first transverse axis 700. In other words, within the context of this disclosure, there may be regions where an interconnection 250 is sandwiched between regions of polymeric substrate (appears as a multilayer in a longitudinal cross-section), adjacent to regions where the polymeric substrate is substantially contiguous. Similarly, there may be regions where an interconnection 250 is sandwiched between two polymeric substrate layers (appears as a multilayer in a longitudinal cross-section), adjacent to regions where the substrate comprises two adjacent substrate layers. Similarly, a substrate comprising two or more polymeric substrate layer may be modified (physically and/or chemically), such that it appears to be one layer of polymeric substrate.

These polymeric substrate layers are selected for suitability to be conformable, and to comprises the one or more electrical interconnections 250. Preferably, the polymeric substrate materials are also biocompatible and durable, such as a material selected from the group comprising silicone rubber, siloxane polymers, polydimethylsiloxanes, polyurethane, polyether urethane, polyetherurethane urea, polyesterurethane, polyamide, polycarbonate, polyester, polypropylene, polyethylene, polystyrene, polyvinyl chloride, polytetrafluoroethylene, polysulfone, cellulose acetate, polymethylmethacrylate, polyethylene, and polyvinylacetate. Suitable examples of polymers, including LCP (Liquid Crystal Polymer) films, are described in "Polymers for Neural Implants", Hassler, Boretius, Stieglitz, Journal of Polymer Science: Part B Polymer Physics, 2011, 49, 18-33 (DOI 10.1002/polb.22169), In particular, Table 1 is included here as reference, depicting the properties of Polyimide (UBE U-Varnish-S), Parylene C (PCS Parylene C), PDMS (NuSil MED-1000), SU-8 (MicroChem SU-8 2000 & 3000 Series), and LCP (Vectra MT1300).

Conformable foil-like substrates 300 are configured to follow the contours of the underlying anatomical features very closely by being flexible. Very thin foil-like substrates 300 have the additional advantage that they have increased flexibility. In general, thinner elements allow placement in a plurality of subcutaneous locations and provide a higher degree of comfort to the subject.

Most preferably, the polymeric substrate layers comprise an LCP, Parylene and/or a Polyimide. LCP's are chemically and biologically stable thermoplastic polymers which allow for hermetic sensor modules having a small size and low moisture penetration.

Advantageously, an LCP may be thermoformed allowing complex shapes to be provided. Very thin (and subsequently very conformable) and very flat (highly planar) layers of an LCP may be provided. For fine tuning of shapes, a suitable laser may also be used for cutting.

For example, a conformable foil-like substrate 300 of LCP may have a thickness (extent along the second transverse axis 750) in the range 50 microns (um) to 720 microns (um), preferably 100 microns (um) to 300 microns (um). For example, values of 150 um (micron), 100 um, 50 um, or 25 um may be provided. The extent along the second transverse axis 750 (thickness) may also be described as a dimension of a cross-section in the transverse plane 700, 750.

When conforming to a substantially planar surface, the foil-like surface 300 is substantially comprised in a plane with a transverse extent substantially perpendicular to the longitudinal axis 600, wherein the planar width may be determined by a perpendicular distance between corresponding points on outer surfaces edges of the planar foil-like substrate 300 along the respective transverse extent. As depicted, this is along the first transverse axis 700. Electrode 200, 400 widths of 2 mm to 20 mm may be provided using LCP, for example. The extent along the first transverse axis 700 (width) may also be described as a dimension of a cross-section in the transverse plane 700, 750

Typically, such a conformal foil-like substrates has an average transverse extent along the second transverse axis 750 (thickness) which is equal to or less than the average transverse extent along the first transverse axis 700 (planar width).

At room temperature, thin LCP films have mechanical properties similar to steel. This is important as implantable substrates 300 should be strong enough to be implanted, strong enough to be removed (explanted) and strong enough to follow any movement of the neighboring anatomical features and/or structures without deteriorating.

LCP belongs to the polymer materials with the lowest permeability for gases and water. LCP's can be bonded to themselves, allowing multilayer constructions with a homogenous structure.

In contrast to LCP's, polyimides are thermoset polymers, which require adhesives for the construction of multilayer portions with at least two electrodes. Polyimides are thermoset polymer material with high temperature and flexural endurance.

An LCP may be used, for example, to provide conformable substrate 300 as a multilayer—in other words, two or more adjacent polymeric substrate layers. For example, these may be layers of 25 um (micron) thickness.

One or more electrical interconnections 250 may be provided between the first (310) and second (320) surfaces by metallization, for example. These may be conductors embedded in the substrate 300—for example, by having a single polymer layer and applying conductive material using suitable deposition techniques known from the semiconductor industry. For example, the substrate may comprise a first conformable layer and at least one second conformable layer, wherein a plurality of electrical interconnection layers 250 are positioned along the first layer using a deposition technique, and wherein the at least one second layer is secured to the first layer so as to cover the plurality of electrical interconnections.

If two or more adjacent polymeric substrate layers are provided, an interconnection layer may be provided using suitable techniques, for example those from the semiconductor industry. The polymeric substrate layers may also be considered adjacent when one of more adhesion layers are used between them.

Lamination may also be used to provide a substrate 300 with the desired physical and chemical properties, and/or to provide a convenient method of manufacture. For example, a substrate 300 may comprise three laminated polymer layers: two high temperature thermoplastic layers with a low-temperature layer (bond-ply) in between, and high-temperature layers towards the first surface 310 and second surface 320.

In another example, two layers of silicone may be provided as polymeric substrate layers: one layer of silicone is provided, metal is patterned on one of its outer surfaces, and a second layer of silicone is added over the metal patterning by, for example, jetting, over-moulding, or spin-coating.

The electrical interconnections 250 may comprise one or more conductors, such as a metal, formed as required—for example, in one or more conductive elements: wire, strand, foil, lamina, plate, and/or sheet. They may be a substantially contiguous (one conductor). They may also comprise more than one conductor, configured and arranged to be, in use, electrically connected with each other—in other words, the one or more conductors are configured and arranged to be substantially electrically contiguous in use.

Alternatively, the one or more electrical interconnections 250 may be comprised in one or more conductive interconnection layers 250, the one or more conductive interconnection layers being comprised between two adjacent polymeric substrate layers. As depicted in FIG. 1A, a plurality of interconnections may be provided at different dispositions (or depths) between the first surface 310 and the second surface 320.

An interconnection 250 in the context of this disclosure is not configured or arranged to be, in use, in contact with human or animal tissue. For example, by embedding the one or more interconnections 250 in one or more layers of a low conductance or insulating polymer, such as LCP. Additionally or alternatively, one or more encapsulation layers may be used.

One or more interconnection layers 250 may also be provided by metallization using techniques from the PCB (Printed Circuit Board) industry, such as metallization with a bio-compatible metal such as gold or platinum. Electroplating may be used. Layers comprising LCP films are particularly suitable for metallization. These electrical interconnections 250 and/or interconnect layers 250 are configured to transfer electrical energy as one or more electrical treatment stimulation pulses from the pulse generator 500 to the first electrode 200a, 200b and/or the second electrodes 400a, 400b.

Using suitable polymeric substrate materials, such as an LCP film, allows the conformable foil-like (or film-like) substrate 300 and the at least two electrodes 200, 400 to have a high width-to-height ration, providing a bio-compatible electronic foil (or film), or bio-electronic foil (or film).

For example, when the substrate 300 is arranged to conform to a substantially planar surface, the ratio of maximum planar width 700 to maximum thickness 750 proximate the first 200a, 200b and second 400a, 400b electrodes may be 7:1 or higher, preferably 10:1 or higher, more preferably 15:1 or higher, yet more preferably 30:1 or higher, even more preferably 50:1 or higher.

Ratios of 100:1 or higher may also be advantageous, and may be provided using one or more mechanically strong substrate layers of an LCP film, with a width of approximately 20 mm and a thickness of approximately 0.2 mm. This provides a high degree of flexibility, and therefore also a high degree of conformability. Additional measures may also be taken to increase the degree of conformability in the first transverse direction 700, such as varying the width of the substrate, adding one or more undulations and/or providing bending points.

When using a single row of electrodes 200, 400 and/or electrodes 200, 400 with a smaller width, the width may be, for example, four mm with a thickness of approximately 0.2 mm—this is a ratio of approximately 20:1.

Proximate the pulse generator 500, greater extents may be required which further depend, to a high degree, on the dimensions of the electronic components used, for example, a width of twenty mm and a thickness of three mm. This is a ratio of approximately 6.67:1.

As depicted in the example of FIG. 1A, the first portion 630 of the substrate 300 comprises:
  two electrodes 200a, 200b of a first type, comprised in the first surface 310, and
  two electrodes 400a, 400b of a second type, also comprised in the first surface 310. From proximal to first portion, the order depicted is 200a, 400a, 200b, 400b—in other words, each electrode of the first type 200a, 200b is proximate an electrode of the second type 400a, 400b and comprised in the same surface 310.

The substrate 300 comprises an electrical interconnection 250 between each electrode 200a, 400a, 200b, 400b and the pulse generator. In this embodiment, each electrical interconnection 250 is configured and arranged such that each electrode 200a, 400a, 200b, 400b is electrically connected substantially independently—consequently, one of the operating modes available by suitably configuring the pulse generator 500 is substantially independent operation. The pulse generator 500 may be configured using one or more hardware, firmware and/or software parameters.

Although depicted in FIG. 1A as individual connections 250 at different distances between the first 310 and second 320 surfaces, the skilled person will also realize that the same interconnections may be provided by a suitably configured interconnections 250 (or an interconnection layer 250) at approximately the same distance between the first 310 and second 320 surfaces.

"Comprised in" the first 310 or second 320 surface means that the electrodes 200a, 400a, 200b, 400b are relatively thin (for example, if the substrate is arranged to conform to a substantially planar surface, it may have an extent along the second transverse axis 750 of 20 to 50 microns or less. Thinner electrodes may be also be used to further increase the degree of conformability, for example 1 micron or less), and attached to (or at least partially embedded in) the surface.

The electrodes 200, 400 may comprise a conductive material such as gold, platinum, platinum black, TiN, IrO2, iridium, and/or platinum/iridium alloys and/or oxides. Conductive polymers, such as Pedot, may also be used. Preferably, bio-compatible conductive materials are used. PCB/metallization techniques may be used to manufacture them on or in the first 310 and/or second 330 surfaces of the one or more polymeric substrate layers.

Thicker metal layers are generally preferred over thinner metal layers for electrodes 200a, 200b, 400a, 400b because they can be subjected to bodily substances that may dissolve the metal. However, thicker metal layers typically increase rigidity (reduce conformability) proximate the thicker layer.

As depicted in FIG. 1, there is no substantial hardware difference between the first-type 200a, 200b and second type 400*a*, 400*b* electrodes—any difference in functionality is determined in this example mainly by the configuration (one or more hardware, firmware and/or software parameters) of the pulse generator 500. There may be a smaller influence on the electrical properties due to the arrangement and routing of the interconnections 250.

One or more electrodes of the same type 200*a*, 200*b* or 400*a*, 400*b* may be operated substantially the same by suitable configuration of the pulse generator 500—in other words, the stimulation energy applied to the electrodes 200, 400 is substantially the same at substantially the same time instance (usually measured as a voltage, a current, a power, a charge, or any combination thereof). This may also be used to anticipate and/or correct for a misalignment and/or lead migration—this is advantageous as it allows the configuration to be performed at least partially using software.

Additionally or alternatively, two or more electrodes 200, 400 may be configured and arranged using one or more parameters of the pulse generator 500 as a stimulation electrode or a return electrode. This may provide a higher degree of configurability as it only becomes necessary to implant the substrate 300 such that at least two of the electrodes are proximate the desired stimulation location.

In this embodiment 100, the electrodes of the first type 200*a*, 200*b* are nominally configured and arranged to be operated as a stimulation electrode.

The electrodes of the second type 400*a*, 400*b* are nominally configured to be operated as a return electrode—each is configured to provide, in use, an electrical return for one or more stimulation electrode 200*a*, 200*b*. In other words, the electrical return 400*a*, 400*b* closes the electrical circuit. It may also be similarly configured to provide an electrical ground for a corresponding electrical energy source.

Three configurations are thus provided based on this nominal configuration: either:
- a stimulation/return electrode pair 200*a*/400*a* proximate the first surface 310 at that stimulation/return location; or
- a stimulation/return electrode pair 200*b*/400*b* proximate the first surface 310 at that stimulation/return location; or
- a combination thereof.

In general, one or more stimulation electrodes 200*a*, 200*b* may be provided in such a stimulator 100. The number, dimensions and/or spacings of the stimulating electrodes 200*a*, 200*b* may be selected and optimized depending on the treatment—for example, if more than one stimulation electrode 200*a*, 200*b* is provided, each stimulation electrode 200*a*, 200*b* may provide:
- a different stimulation effect, a similar stimulation effect or the same stimulation effect.

To avoid a misalignment, a selection may be made of one or two electrodes 200*a*, 200*b* proximate the tissues where the effect is to be created.

Two or more stimulation electrodes 200*a*, 200*b* may be made active at substantially the same time if stimulation over a larger area is required and/or at a location between the active stimulation electrodes 200*a*, 200*b*.

A stimulation electrode 200*a*, 200*b* may have, for example, dimensions in the order of six to eight mm along the longitudinal axis 600, and three to five mm along the first transverse axis 700, so approximately 18 to 40 square mm (mm2).

A substrate 300, suitable for an implantable stimulator, may comprise, for example, up to twelve stimulation 200*a*, 200*b* and return 400*a*, 400*b* electrodes over a length of 15 cm to allow for a correction for misalignment, or to simply allow the specialist to select the most effective stimulation location.

FIG. 1B depicts a view of the second surface 320 of the implantable first portion of the substrate 300 depicted in FIG. 1A. In other words, the second surface 320 is depicted in the plane of the paper, lying along the longitudinal axis 600 (depicted from bottom to top) and in the first transverse axis 700 (depicted from left to right). The second transverse axis 750 extends into the page. The first surface 310 is not depicted in FIG. 1B, but lies at a higher position along the second transverse axis 750 (into the page), and is also substantially parallel to the plane of the drawing. The substrate 300 is arranged to conform to a substantially planar surface.

In general:
- the first portion 630 comprises substantially only one or more electrodes 200, 400 and one or more interconnections 250; and
- the further portion 630 comprises one or more electrical components, disposed between the second 320 surface and the first 310 surface. Alternatively, the one or more electrical components may be at least partially disposed on the first surface 310 or on the second surface 320. Alternatively, the one or more components may be at least partially embedded in the first surface 310 or in the second surface 320.

Depending on, for example, the degree of embedding and the one or more electrical components used, the maximum thickness and/or planar width may be optimized. Components may be thinned to minimize the thickness. Components may include one or more pulse energy receivers and/or one or more pulse generators 500 to provide, in use, stimulation pulses to the electrodes 200, 400. Additional optional electrical components, such as an antenna (for example, a coil or dipole or fractal antenna), may also influence the thickness and/or width depending on the degree that they are embedded in the substrate.

Advantageously, the further portion comprises a pulse generator 500. Optionally, it may be disposed between the second 320 surface and the first 310 surface. In FIGS. 1B and 1C, it is depicted with dotted lines. Alternatively, the pulse generator 500 may be at least partially disposed on the first surface 310 or on the second surface 320. Alternatively, the pulse generator 500 may be at least partially embedded in the first surface 310 or in the second surface 320.

Depending on, for example, the degree of embedding and the one or more electrical components used for the pulse generator 500, the maximum thickness (maximum transverse extent along the second transverse axis 750) may be optimized. Additionally or alternatively, the maximum planar width (maximum transverse extent along the first transverse axis 700) may be optimized.

If the substrate 300 is configured and arranged to be conformable and/or foil-like, the maximum thickness (extent along the second transverse axis 750) of the implantable stimulator 100 proximate the pulse generator 500 may be five millimeters or less, preferably four millimeters or less, even more preferably three millimeters or less, the thickness being determined by a perpendicular distance between corresponding points on outer planar surfaces when the implantable stimulator 100 conforms to a substantially planar surface.

The maximum transverse extent 710 at the further portion 610 is arranged off-center with respect to the longitudinal axis 600. In this example, the proximal 630 end, the portion comprising no stimulation electrodes 350 and the first portion 630 share a common boundary or edge along the first transverse axis. This may be more convenient to implant using the edge as a reference for positioning and/or creating an adequately sized skin pocket. In addition, the orientation of the further portion 610 may be used to determine upward and/or downward facing surface 310, 320. This may be advantageous where the electrodes 200, 400 are comprised in one surface 310, 320.

The stimulator 100 and the substrate 300 extend along the first transverse axis 700 (considered the planar width of the stimulator 100/substrate 300 when conforming to a substantially planar surface). As depicted, the maximum planar width 710 at the proximate end 610 is substantially greater than the maximum planar width 730 at the first portion of the substrate 300. In this example, the maximum planar width 710 proximate the pulse generator 500 is substantially greater than the maximum planar width 730 proximate the electrodes 200a, 200b, 400a, 400b.

The maximum planar width 710 proximate the energy receivers and/or pulse generator 500 depends on, for example, the hardware and components used—typically, it is at least the width of the largest integrated circuit used. Additional optional electrical components, such as an antenna (for example, a coil or dipole or fractal antenna), may also influence the maximum planar width.

The maximum planar width 730 proximate the electrodes 200a, 200b, 400a, 400b depends on, for example, the conductors used for the electrodes 200a, 200b, 400a, 400b and the one or more interconnections 250—typically, it is at least the width of the first electrode 200a, 200b or the second electrode 400a, 400b.

FIG. 1C depicts a view of the first surface 310 of the implantable first portion of the substrate 300 depicted in FIGS. 1A and 1B. In other words, the first surface 310 is depicted in the plane of the paper, lying along the longitudinal axis 600 (depicted from bottom to top) and in the first transverse axis 700 (depicted from right to left). The second transverse axis 750 extends out of the page. This is the view facing the animal or human tissue which is stimulated (in use). The second surface 320 is not depicted in FIG. 1C, but lies at a lower position along the second transverse axis 750 (into the page), and is also substantially parallel to the plane of the drawing. The substrate 300 is arranged to conform to a substantially planar surface.

The one or more interconnections 250 are disposed between the first 310 surface and the second 320 surface, as depicted in FIG. 1A. In FIG. 1C, they are depicted as dotted lines, representing the interconnections 250 (or suitably configured one or more interconnection layers 250) that have been provided for each of the electrodes 200a, 200b, 400a, 400b in this embodiment. A single dotted line 250 is depicted between the pulse generator 500 and the electrodes 200, 400 to indicate, in this example 100, that the interconnections 250 are at approximately the same disposition along the first transverse axis 700.

As depicted in FIG. 1C, the electrodes 200a, 200b, 400a, 400b each have a longitudinal extent (length) along the longitudinal axis 600 and a transverse extent (width) along the first transverse axis 700.

Although depicted as similar, in practice, each electrode 200a, 200b, 400a, 400b may vary in shape, transverse cross-section, orientation and/or size (or extent), depending on the intended use and/or the desired degree of configurability.

After implantation of the stimulator 100, or at least of the conformable first portion comprising the at least two electrodes 200, 400, the pulse generator 500 may be configured and arranged to provide, in use, electrical energy to the one or more electrodes of the first type 200a, 200b with respect to the electrical return applied to the one or more electrode of the second type 400a, 400b.

The configurability of the stimulator 100 allows, before, during and/or after implantation of at least of the first portion comprising the at least two electrodes 200, 400, the operation of the one or more electrodes 200a, 200b, 400a, 400b to be determined and/or adapted. The operation may also be reconfigured one or more times during the period that the stimulator 100 is implanted to optimize and/or prolong treatment.

For example, the pulse generator 500 may be initially configured to nominally operate 200a and 400a as respectively a stimulation/return electrode pair. After implantation of at least the first portion 200, 400, insufficient stimulation may be observed and/or measured. If it is assumed to be due to a mainly longitudinal misalignment, the pulse generator 500 may be alternatively configured, using one or more parameters, to nominally operate 200b and 400b as respectively a stimulation/return electrode pair.

The stimulator 100 may be further configured and arranged to switch the pulse generator 500 under predetermined and/or controlled conditions between these configurations. It may be convenient to further consider these configurations as a first and second electrode modes, and allow a user to select a mode as a preference and/or switch modes. Alternatively, the pulse generator 500 may switch modes under predetermined and/or controlled conditions.

Additionally or alternatively, other modes may also be provided—for example, configuring the pulse generator 500 to operate in:
a first electrode mode, wherein electrical stimulation energy is provided to one or more electrodes of the first type 200a, 200b as one or more electrical treatment stimulation pulses, the one or more electrodes of the second type 400a, 400b being configured to provide, in use, a corresponding electrical return for the one or more first electrodes 200a, 200b; or
a second electrode mode, wherein to one or more electrodes of the second type 400a, 400b as one or more electrical treatment stimulation pulses, the one or more electrodes of the first type 200a, 200b being configured to provide, in use, a corresponding electrical return for the one or more second electrodes 400a, 400b.

Again, the stimulator 100 may be further configured and arranged to switch the pulse generator 500 under predetermined and/or controlled conditions between these configurations or modes. Additionally or alternatively, a user may be allowed to select a mode as a preference and/or switch modes.

The skilled person will realize that the electrodes 200a, 200b, 400a, 400b may be configured to operate in more complex configurations, such as:
400a and 200a may be operated as respectively a stimulation/return electrode pair (reversing the original intended operation);
400b and 200b may be operated as respectively a stimulation/return electrode pair;
if an intermediate stimulation is preferred, two or more electrodes 200a, 200b, 400a, 400b may be operated substantially simultaneously as one or more stimulation electrodes;
one or more electrodes 200a, 200b, 400a, 400b may be operated as one or more return electrodes;

electrode 400*a* operated as a stimulation electrode, in combination with electrode 200*a* and electrode 200*b* as return electrodes;

electrode 400*a* and 200*b* operated as a stimulation electrode, in combination with electrode 200*a* and electrode 400*b* as a return electrode.

Alternatively or additionally, the shape, orientation, transverse cross-section, and/or size (or length) of one or more stimulation electrodes may be differently configured compared to one or more return electrodes.

A number of parameters and properties may be considered when configuring and arranging the substrate 300 proximate the at least two electrodes 200, 400 for conformability, such as:

the transverse 700 and/or longitudinal extent 600 of the one or more electrodes 200*a*, 200*b*, 400*a*, 400*b* the thickness of the substrate 300, or the perpendicular distance between the first surface 310 and the second surface 320 the materials comprised in the substrate 300, and their physical properties the number and extent of interconnections 250 and/or interconnection layers 250 between the first surface 310 and second surface 320.

There have been attempts to make traditional leads, such as cylindrical leads, much thinner to allow subcutaneous implantation and/or to increase comfort by flattening. But the surface area of the flattened electrodes may become disadvantageously small.

For example, a conventional 0.2 mm round lead with 1 cm long electrodes is estimated to result in an electrode with approximately 6 mm2 electrode surface.

However, using the conformable first portions with at least two electrodes described herein, a relatively thin substrate 300 with dimensions of 0.2 mm thick, and four mm wide may be configured and arranged to provide approximately 35 mm2 electrode surface in the same length. It is estimated that this may reduce impedance by a factor of approximately 35/6, and reduce power consumption by approximately 35/6.

Figure 1D:
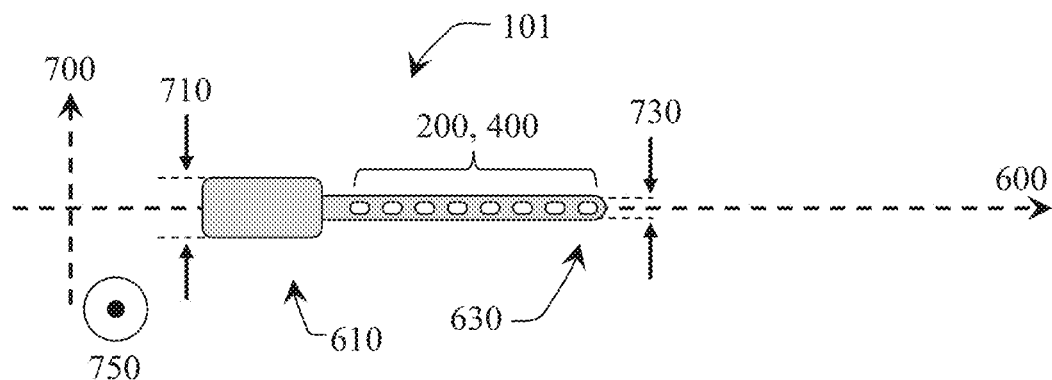

FIG. 1D depicts a second embodiment of an implantable stimulator 101. It is the same as the first embodiment 100 depicted in FIG. 1A to 1C, except:

the first portion 630 comprises a 1D array of eight electrodes 200, 400, which may be configured as one or more stimulation electrodes 200 and one or more associated return electrodes 400;

the separation between the further portion 610 and the first portion 630 is relatively small, so the portion of the substrate comprising no stimulation electrodes is also relatively small; and the maximum transverse extent 710 at the further portion 610 is arranged approximately centered with respect to the longitudinal axis 600. This centered configuration may make it easier for the specialist to use implantation tools and to estimate the required extents for any skin pockets to be formed.

Alternatively or additionally, a short portion of the substrate comprising no stimulation electrodes may be manufactured longer, but shortened during the implantation—for example, by folding, twisting and/or implanting at least a portion of the surplus portion.

Figure 1E:
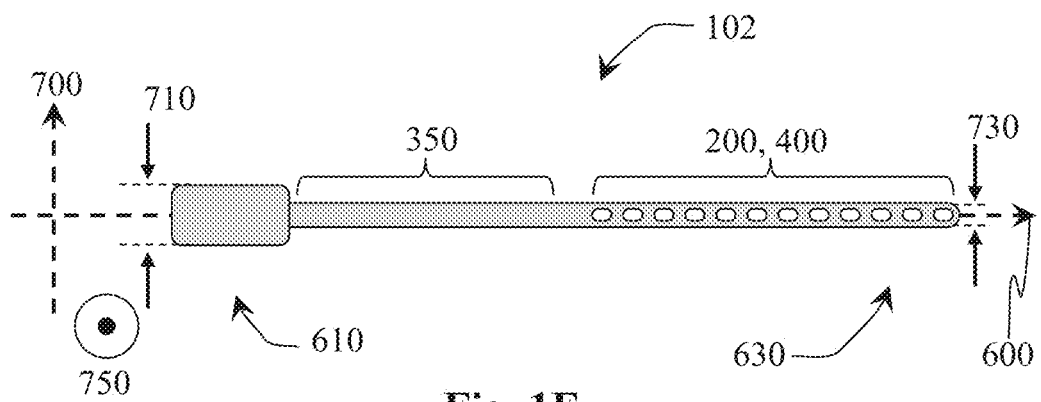

FIG. 1E depicts the third embodiment of an implantable stimulator 102. It is the same as the first embodiment 100 depicted in FIG. 1A to 1C, except:

the first portion 630 comprises a 1D array of twelve electrodes 200, 400, which may be configured as one or more stimulation electrodes 200 and one or more associated return electrodes 400;

the separation between the further portion 610 and the first portion 630 is visible and relatively large. So the portion of the substrate comprising no stimulation electrodes 350 is also relatively large; and the maximum transverse extent 710 at the further portion 610 is arranged approximately symmetrical with respect to the maximum transverse extent 730 at the first portion 630. This may be more convenient to manufacture.

Alternatively or additionally, the portion of the substrate comprising no stimulation electrodes 350 may be provided by disabling and/or disconnecting one or more electrodes 200, 400 in a portion with at least two electrodes 630.

In general, stimulators 100 may be implanted by first creating a subcutaneous tunnel and/or using an implantation tool. However, a high degree of conformability may make successful implantation more difficult. Even when using a suitable insertion tool, the electrode positions may be found later to be incorrect due to, for example, misalignment, lead migration during implantation, or lead migration after transplantation.

At least the first portion 630 comprising the at least two electrodes 200, 400, is implanted. However, it may be advantageous to also implant the further portion 610.

In addition, during implantation, it may be difficult to precisely identify the desired position for the stimulation—for example, the stimulator electrodes should be positioned sufficiently close to the nerve to be stimulated. But nerve pathways may not always be clearly visible to the specialist performing the implantation, and the disposition and path of the nerve pathways vary greatly from person-to-person.

A further problem may occur when longitudinally-extended stimulators have relatively larger transverse extents (here described as thickness or width)—the dimensions of implantation tools and/or subcutaneous tunnels are typically dimensioned based on the transverse extent. This means that to implant stimulators with relatively larger transverse extents, larger dimensioned tools may be required and/or more invasive procedures may be required when using conventional methods.

In general, for any type of implantable stimulator with any type of lead and/or interconnection with any transverse cross-sectional shape, the tunnels and/or tools are dimensioned based on the largest transverse cross-section of the portions of the stimulator to be implanted. If the first 700 and second 750 transverse axes are substantially perpendicular to the longitudinal axis 600, then it may also be defined as the maximum transverse extent along one or more transverse axes 700, 750.

For stimulators with varying transverse cross-sections at positions along the longitudinal axis 600, the dimensions of implantation tools and/or subcutaneous tunnels are typically dimensioned based on the maximum transverse cross-section at any point along the longitudinal axis 600 of the implantable portion.

This may be particularly disadvantageous for stimulators where the interconnecting wires cannot be disconnected from the further portion without a risk of damaging the encapsulation. As the stimulation source generally has a larger transverse cross-section, it is this transverse cross-section which generally determines the minimum size of incisions and/or implantation tools.

For the stimulators 100 disclosed herein, the maximum transverse cross-section 710 of the further portion 610, is substantially greater than the maximum transverse cross-section 730 of the first portion 630. In this context, substantially greater means that the maximum proximal transverse cross-section 710 is at least 20% greater than the maximum distal transverse cross-section. In other words, greater by at least a factor of 1.2. In practice, stimulators may have factors greater than 1.3, 1.5, 2.0, 3.0, 5.0, 10, as smaller first portions are often preferred.

For example, maximum proximal transverse cross sections 710 may be in the range 10 mm to 50 mm, such as 20 mm. For example, maximum distal transverse cross sections 730 may be in the range 2 mm to 20 mm, such as 4 mm For such asymmetric stimulators, conventional implantation methods are less suitable.

Although in the examples disclosed herein, the maximum transverse cross-sections 710, 730 are both along the first transverse axis 700, it will be obvious to the skilled person that the methods may be advantageously used where the maximum transverse cross-sections 710, 730 may be along identical transverse axes, similar transverse axes, or along substantially different transverse axes 700, 750.

Figure 8D:
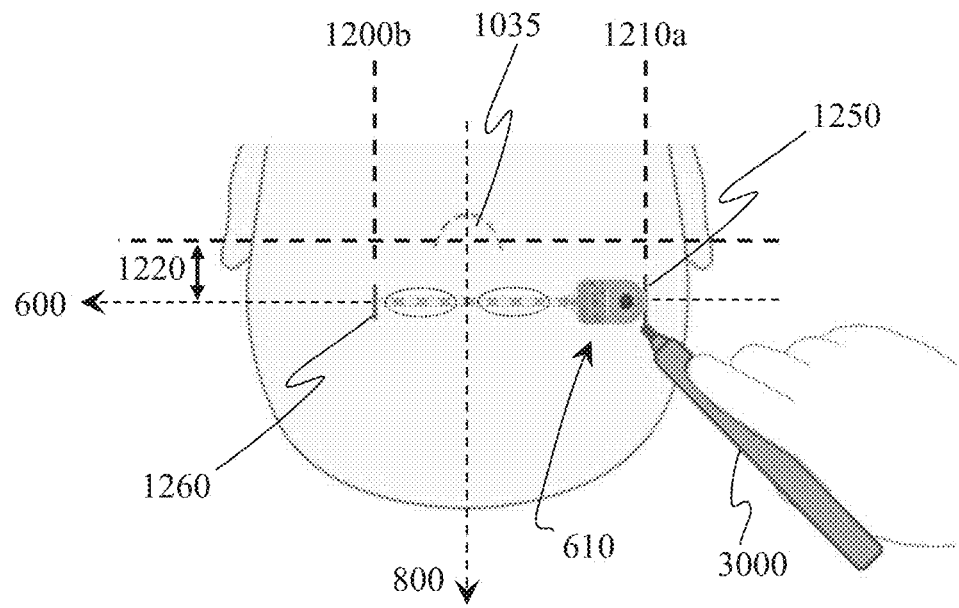
FIG. 8A to 8O depict a method to implant a stimulator, suitable for occipital nerve stimulation (ONS).
Figure 8E:
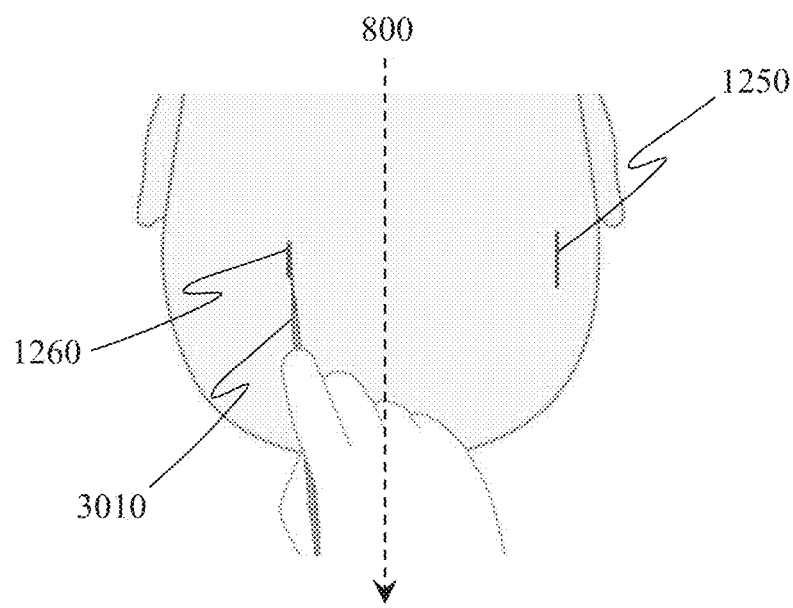
Figure 8F:
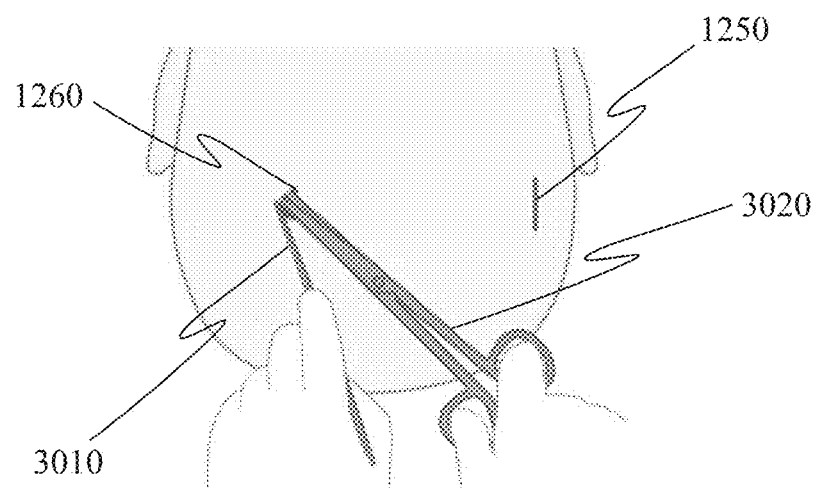
Figure 8G:
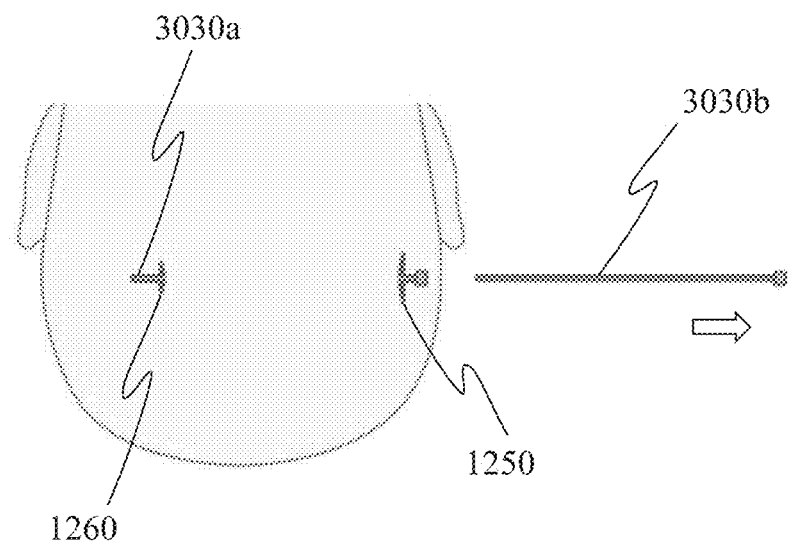
Figure 8H:
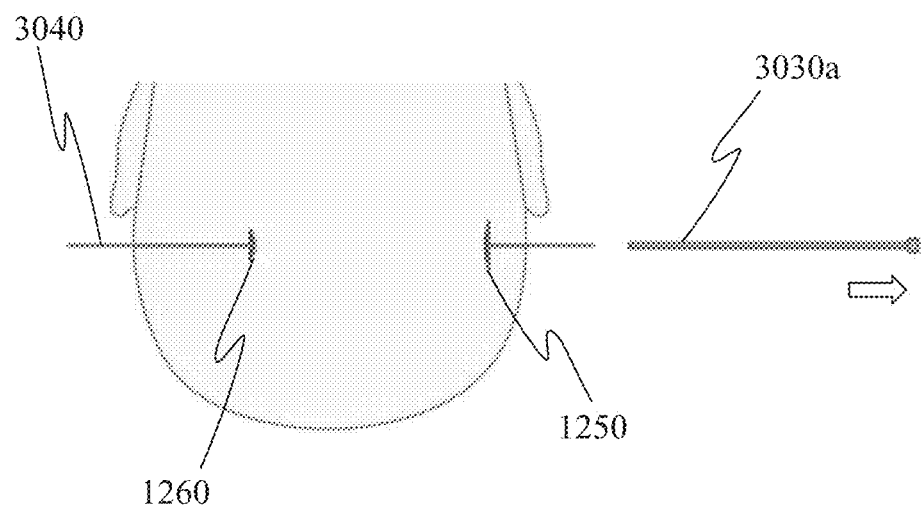
Figure 8I:
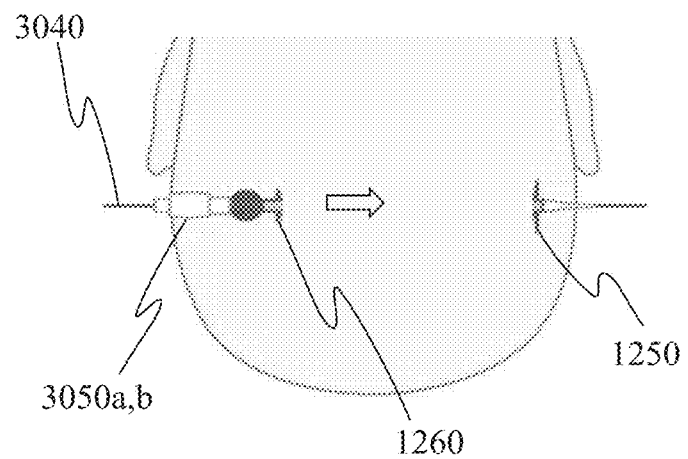
Figure 8J:
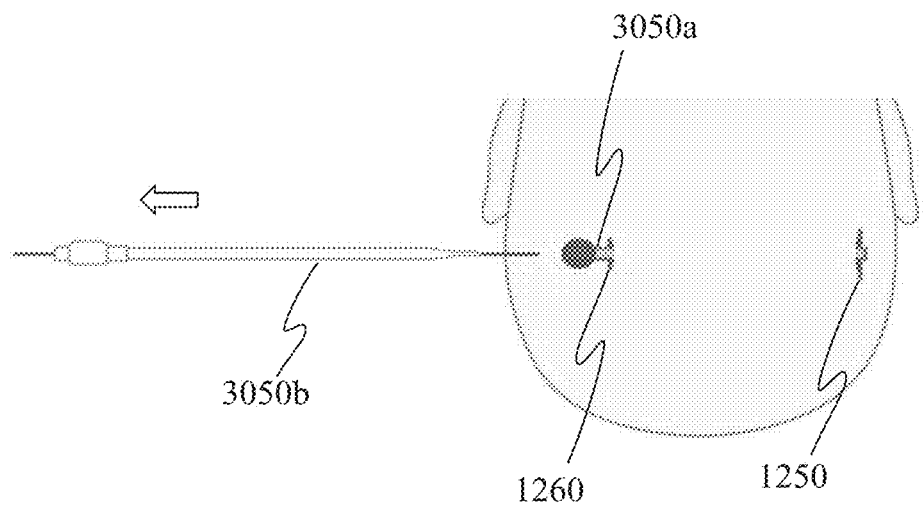
Figure 8K:
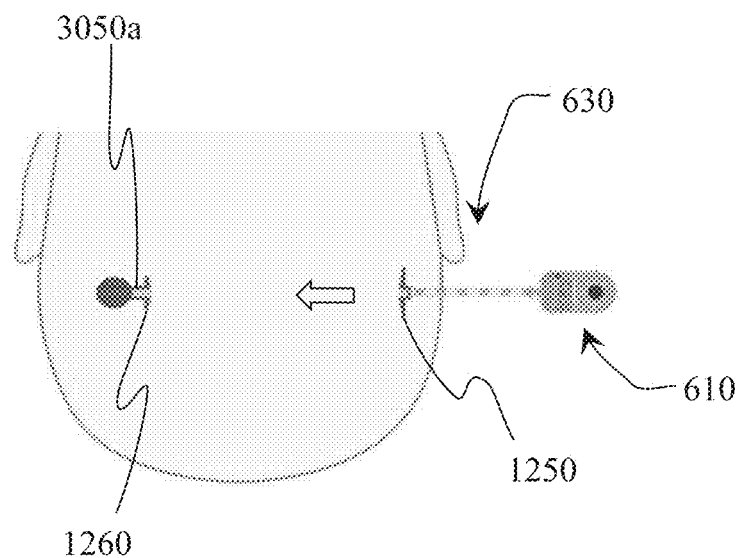
Figure 8L:
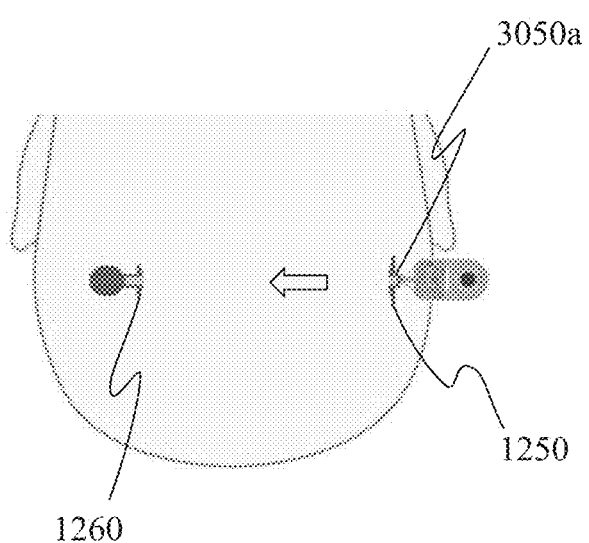
Figure 8M:
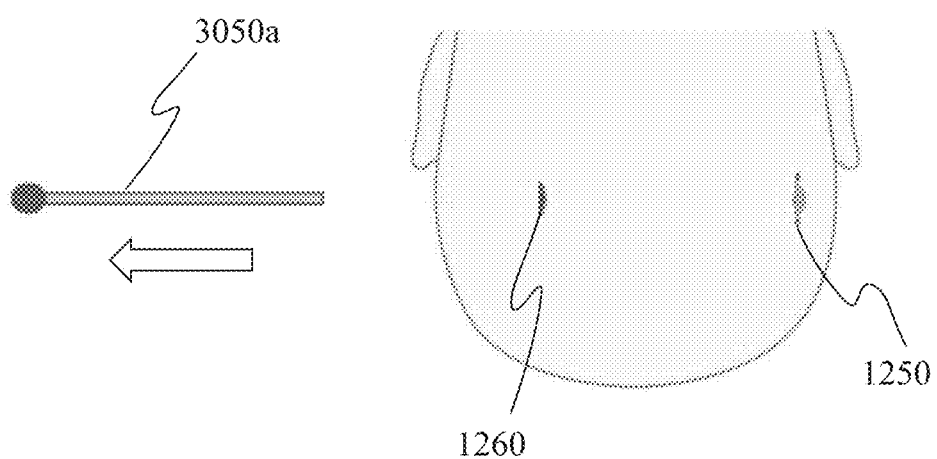
Figure 8N:
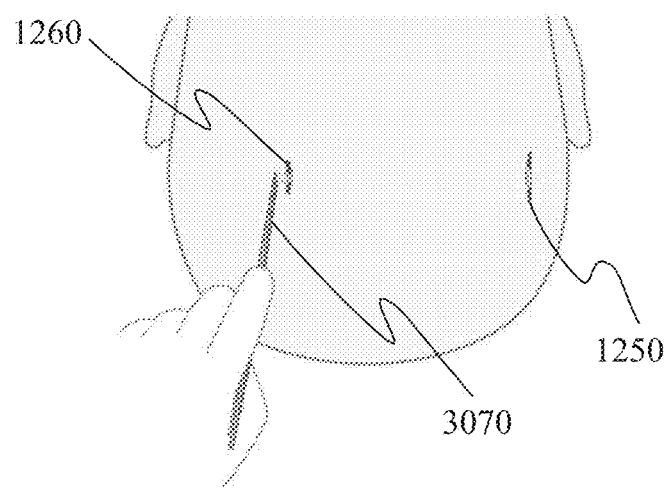
Figure 8O:
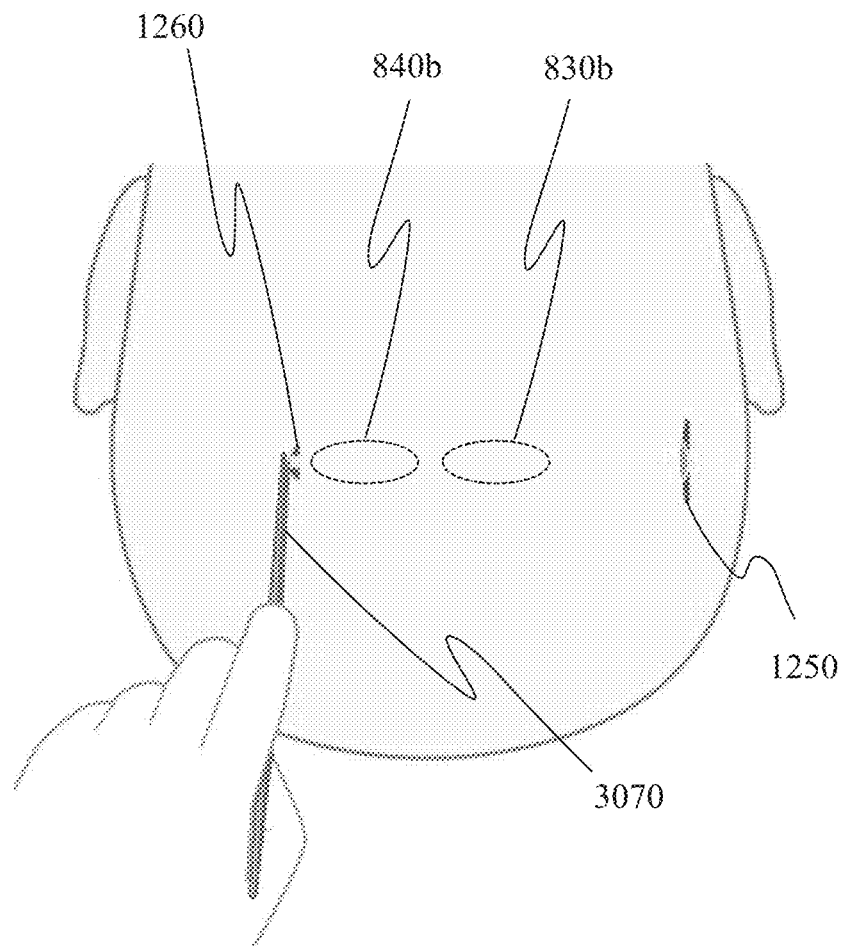

FIG. 8A-8O depict a first method to implant a stimulator at a target location, namely at approximately one cm superior ("above") to the occipital protuberance inion of a subject 1000. The disposition of the implanted stimulator is suitable for occipital nerve stimulation (ONS).

Figure 6:
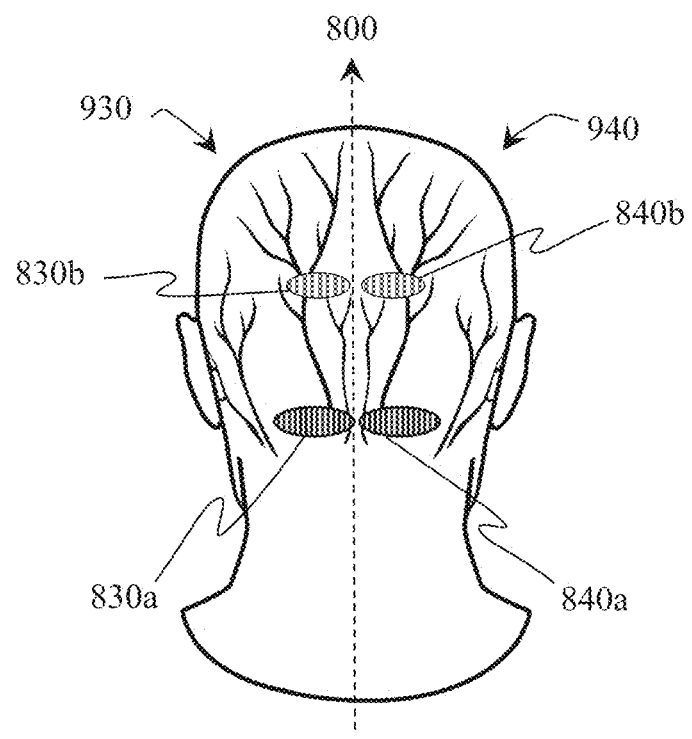

This disclosure considers a first location 840a and a second location 840b for a right occipital nerve stimulation and a first position 830a and a second location 830b for left occipital nerve stimulation—both are depicted in FIG. 6 and described further below.

In human anatomy, the external occipital protuberance is located near the middle of the squamous part of occipital bone. The inion is the highest point of this protuberance—it is commonly used as an anatomical landmark—for example, in the 10-20 system in electroencephalography (EEG) recording.

Using this first method, the second embodiment of implantable stimulator 101 depicted in FIG. 1D, may be advantageously implanted due to a relatively small portion 350 comprising no stimulation electrodes 200.

Additionally or alternatively, the portion of the substrate comprising no stimulation electrodes comprised in the first 100 and third embodiments 102 may shortened during implantation to provide a suitably dimensioned stimulator. Advantageously, it may be shortened by the specialist creating one or more additional skin pockets to retain excess length of the substrate.

FIGS. 8A and 8B depict a recommended starting position from as viewed from above the subject 1000 and above the back 1015 of the subject's head. The head of the subject is 1000 is placed face-down. A median plane 800 of the subject 1000 is depicted vertically in FIGS. 8A and 8D, the arrow indicating the cranial direction. The median plane 800 is a plane of symmetry which divides the head of the subject 1000 into left and right, passing through, for example, the spinal cord.

As depicted, the target area for stimulation is the second location 840b for a right occipital nerve stimulation and/or the second position 830b for left occipital nerve stimulation—the first portion 630 of the implantable stimulator 101 is configured and arranged to stimulate one or more regions on the back 1015 of the subject's 1000 head.

It may be advantageous to initially shave the region of skin being treated, including the area 1100 on the back 1015 of the head. In most subject's 1000, this position is covered with hair, which will further hide scarring and/or protruding portions which may occur after implantation.

FIG. 8C depicts an initial positioning of the implantable stimulator 101 from above the back 1015 of the subject to determine the positions for the incisions.

Through palpation and/or suitable scanning/imaging, the external occipital protuberance inion 1035 of the subject 1000 is located—this is to be used as the main anatomic landmark to help with positioning of the stimulator 101 for the first method.

The implantable stimulator 101 is positioned such that an approximate center of the first portion 630 electrodes array 200, 400 is positioned approx. one cm 1220 superior ("above") to the occipital protuberance 1035 in the cranial direction along the median axis 800. The longitudinal length of the portion comprising at least two electrodes 200, 400 extends laterally from the median plane 800, from the first lateral border 1200a to the second lateral border 1200b.

For example, an eight cm long portion with at least two electrodes 200, 400 may be used to provide approximately two laterally-disposed forty mm lengths of portions with at least two electrodes 200, 400 on each side of the approximate center of the first portion 630. The longitudinal axis 600 of the portion with at least two electrodes 200, 400 is disposed approximately perpendicular to the median axis 800. The first 1200a and second 1200b lateral borders are disposed approximately parallel to the median plane 800. In the case that electrodes 200, 400 are comprised throughout the first portion 630, at the center point, the number of electrodes 200, 400 from the middle of the protuberance 1035 are approximately equal.

The dimensions of the portion with at least two electrodes 200, 400 may be predetermined and/or controlled to provide stimulation over a suitable area of tissue. For implantation at regions where anatomic variation is relatively low for the expected subjects, it may be advantageous to provide a stimulator with standardized dimensions. Additionally or alternatively, it may be advantageous to provide a range of standardized sizes and/or size ranges that the specialist may choose from. Additionally or alternatively, the stimulator may be configured and arranged to be custom fit for one or more subjects. Additionally or alternatively, flexibility may be provided to the specialist by allowing one or more electrodes 200, 400 from a plurality of electrodes to be selected for the required stimulation.

Additionally or alternatively, it may be advantageous to use data from one or more anatomical databases, such as DINED: https://dined.io.tudelft.nl/en/about to determine the most appropriate dimensions.

The stimulator 101 is flattened by the specialist over the outer surface of skin laterally from the median plane 800 to find the placement of the further portion 610 with either a pulse generator 500 or a pulse energy receiver, such as a coil. As depicted, it is on the left side of the subject's 1000 head. The longitudinal length of the further portion 610 extends from the further lateral border 1210a to the first lateral border 1200a/1210b. The first 1200a/1201b and further 1210a lateral borders are disposed approximately parallel to the median plane 800. The implantable stimulator 101 is preferably visually and/or manually checked to reduce the risk that the implantable stimulator substrate is strained and/or twisted along its path—FIG. 8C.

It will be obvious to the skilled person that the method may be mirrored such that the further portion 610 is implanted on the right side of the subject's 1000 head.

FIG. 8D depicts initial marking of the incision sites. The extent 1250 of the further portion 610 is marked on the skin as a first incision mark 1250 at the further lateral border 1210a. A second 1260 incision mark is marked on the skin to indicate the extent of the portion with at least two electrodes 200, 400 (first portion 630) at the left lateral border 1200*b*. The first 1250 and second 1260 incision marks extend approximately parallel to the median plane 800. For example, a tissue marker 3000 may be used. It may also be advantageous to determine and mark the extent and positions of vascular structures (not depicted) in this area—this may reduce the risk that the vascular structures are damaged during the rest of the implantation method.

FIG. 8E depicts initial incisions. Two incisions are made using a tissue knife 3010, such as a surgical scalpel: the first at the first incision mark 1250, approximately thirty mm in length; and the second at the second incision mark 1260, approximately twenty mm are made. The first 1250 and second 1260 incisions extend approximately parallel to the median plane 800.

FIG. 8F depicts the forming of skin pockets for receiving one or more portions of the stimulator. Using a tissue knife 3010 and/or blunt scissors/forceps 3020, a second skin pocket is created extending approximately ten mm by, for example, blunt dissection around the second 1260 incisions. Similarly, a first skin pocket is created, for example, by blunt dissection around the first incision 1250. As the maximum extent in transverse directions 700, 750 of the implantable stimulator at the further portion 610 is greater than the maximum transverse extent of the first portion 630, the skin pocket at the first incision 1250 is correspondingly larger than at the second 1260 incision.

FIG. 8G depicts a possible preparation of the implant path. The tip of a guidewire introducer needle assembly 3030*a,b*, preferably an epidural needle such as a Tuohy needle assembly, is inserted at the first incision 1250 and further inserted under the skin until the tip emerges from the second incision 1260. The guidewire introducer mandrin 3030*b* is removed from the guidewire introducer needle assembly 3030*a,b* to leave the guidewire introducer needle 3030*a* extending under the skin from the first incision 1250 to the second incision 1260. The guidewire introducer needle 303*a* is preferably blunt.

As depicted in FIG. 8H, a guide wire 3040 is inserted through the guidewire introducer needle 3030*a*. The guidewire introducer needle 3030*a* is removed from under the skin to leave the guide wire 3040 extending under the skin from the first incision 1250 to the second incision 1260, extending on both sides from the incisions 1250, 1260.

As depicted in FIG. 8I, a first introducer assembly 3050*a,b* is inserted under the skin over the guidewire 3040 from the second incision 1260 to the first incision 1250.

As depicted in FIG. 8J, the guide wire 3040 and first introducer mandrin 3050*b* are removed from under the skin to leave the first introducer sheath 3050*a*, extending under the skin through the second incision 1260 to the first 1250 incision.

Alternatively, the first introducer assembly 3050*a,b* may be inserted under the skin over the guidewire 3040 from the first incision 1250 to the second incision 1260. The guide wire 3040 and first introducer mandrin 3050*b* may be removed from under the skin to leave the first introducer sheath 3050*a*, extending under the skin through the first 1250 incision to the second incision 1260 position.

As depicted in FIGS. 8K and 8L, the first portion 630 of the implantable stimulator 101, comprising the portion with at least two electrodes 200, 400, is inserted into the first introducer sheath 3050*a* from the first incision 1250 to the second incision 1260. The first portion 630 of the implantable stimulator 101 is comprised within the body of the first introducer sheath 3050*a*.

As depicted in FIGS. 8M and 8N, the first introducer sheath 3050*a* is removed. The first portion of the implantable stimulator 101 is pulled using, for example, tweezers or silicone-tipped tweezers 3070, such that it extends further from the second incision 1260 position, and the further portion of the implantable stimulator 101 with the electrical components is introduced into the skin pocket at the first incision 1250.

As depicted in FIG. 8O, the first portion of implantable stimulator 101 is also pulled at the second incision 1260 using tweezers 3070 to check that the lead substrate is flattened underneath the skin—this may be checked visually, using palpation and optionally with a diagnostic imager, such as an x-ray imager. If the portion with at least two electrodes 200, 400 positioning is incorrect, it may be corrected by gently pulling on the distal and/or further portion using silicone-tipped tweezers.

The tip of the first portion 630 is guided into the skin pocket at the second incision 1260. The first 1250 and second 1260 incisions are closed, preferably in layers with subcutaneous and cutaneous sutures.

In this first method, the dimensions of implantation tools and/or subcutaneous tunnels are typically dimensioned based on the maximum transverse cross-section 700, 730, 750 of the first portion 630, and in particular the portion with at least two electrodes 200, 400.

In other words, although the maximum proximal transverse cross-section 710 is at least 1.2 times greater than the maximum distal transverse cross-section 730, the further portion 610 dimensions do not directly influence the dimensions of implantation tools and/or subcutaneous tunnels. However, the skilled person will realize that the first skin pocket created around the first incision 1250 should be dimensioned to be sufficiently large enough for the further portion 610.

In this first method, the following implantation tools may be used:
- a guidewire introducer needle assembly 3030*a,b*, comprising a guidewire introducer needle 3030*a* enclosing a guidewire introducer mandrin 3030*b* (FIG. 8G). Preferably the guidewire introducer needle 303*a* is blunt. An epidural needle is preferred—it is a hollow hypodermic needle, very slightly curved at the end, suitable for inserting epidural catheters. A mandrin is a stiff wire or tube used to give more flexible guidewire introducer needles more resilience and strength when being inserted and/or removed. Additionally or alternatively, a mandrin may provide for closure of the lumen of the needle. The lumen of the guidewire introducer needle 3030*a* is at least large enough to receive a suitable guide wire 3040—in other words, the guidewire introducer needle 3030*a* has a minimum internal transverse cross-section which is greater than the maximum transverse cross-section of the guide wire 3040; The length is at least the distance from the first lateral border 1200*a* to the second lateral border 1200*b*. Typically, a gauge of 20G is used. For example, a Tuohy needle assembly may be used;
- a guide wire 3040 is inserted through the guidewire introducer needle 3030*a* (FIG. 8H). The guidewire introducer needle 3030*a* is removed from under the skin to leave the guide wire 3040 extending under the skin. The maximum transverse cross-section of the guide wire 3040 is at least sufficiently smaller than the inner lumen dimensions of the guidewire introducer needle 3030*a* so that the guide wire 3040 may be inserted—in other words, the guide wire 3040 has a maximum transverse cross-section less than the minimum internal transverse cross-section of the guidewire introducer needle 3030a. The length is at least the distance from the first lateral border 1200a to the second lateral border 1200b. Typically, a gauge of 20G is used; and a first introducer assembly 3050a,b is inserted under the skin over the guidewire 3040 (FIG. 8I). An introducer is generally an instrument, such as a catheter, needle, or endotracheal tube, for introduction of a flexible device. The first introducer assembly 3050a,b comprises a first introducer sheath 3050a enclosing a hollow first introducer mandrin 3050b. The lumen of the introducer mandrin 3050b is at least large enough to receive the guide wire 3040—in other words, the introducer sheath 3050a has a minimum internal transverse cross-section that is greater than the maximum transverse cross-section of the guide wire 3040. The length is at least the distance from the first lateral border 1200a to the second lateral border 1200b. Typically, a gauge of 20G is used. The lumen of the first introducer sheath 3050a is also at least large enough to receive the first portion 630 of the implantable stimulator 101—in other words, the introducer sheath 3050a has a minimum internal transverse cross-section that is greater than the maximum transverse cross-section of the first portion 630 of the stimulator. The method is particularly advantageous when the first introducer sheath 3050a has a maximum internal transverse cross-section less than the maximum proximal transverse cross-section 710 of the substrate 300;

In summary, the method comprises at least the steps of:
identifying a target location for stimulation;
forming a first 1250 and second 1260 incision on opposite sides of the target location;
introducing a first introducer sheath 3050a under the skin from the second incision 1260 to the first incision 1250, the first introducer sheath 3050a having a maximum internal transverse cross-section less than the maximum proximal transverse cross-section 710 of the substrate 300;
introducing the first portion 630 of the implantable stimulator 100, comprising the portion with at least two electrodes 200, 400, into the first introducer sheath 3050a from the first incision 1250 to the second incision 1260;
removing the first introducer sheath 3050a, whereby the implantable stimulator extends under the skin from the further portion 610 at the first incision 1250 to the first portion 630 at the second incision 1260 whereby the at least two electrodes 200, 400 is arranged to transfer treatment energy to the target location.

So, using an introducer sheath 3050a and two incisions 1250, 1260, the stimulator 100, 101, 102, 103, 104, 105, may be implanted at many target locations in the body of the subject.

It may also be advantageous to implant the further portion 610 on the side of the subject's 1000 head, superior ("above") to the ear 1020, 1021. In that case, the first method may further comprise additional acts, similar to the second method explained below, where a third incision is made to allow implantation of the further portion superior to ("above") the ear 1020, 1021. In that case, the first embodiment 100 depicted in FIG. 1A to 1C, or the third embodiment of implantable stimulator 102 depicted in FIG. 1E, may be thus advantageously implanted due to the portion 350 comprising no stimulation electrodes 200.

Figure 3A:
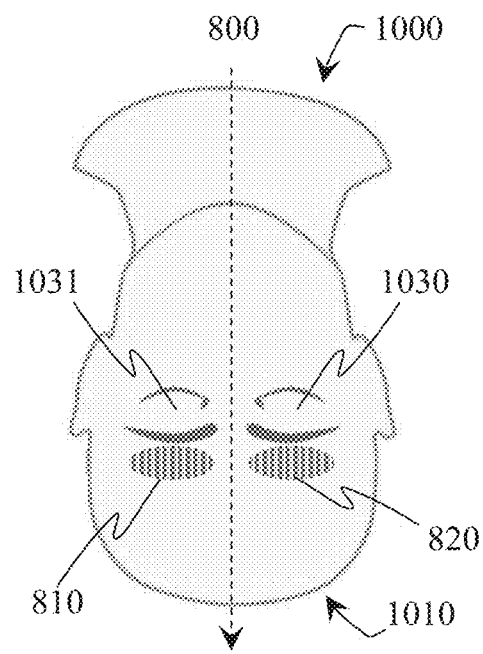
FIG. 3A to 3V depict a method to implant a stimulator, suitable for supraorbital nerve stimulation (SONS)
Figure 3B:
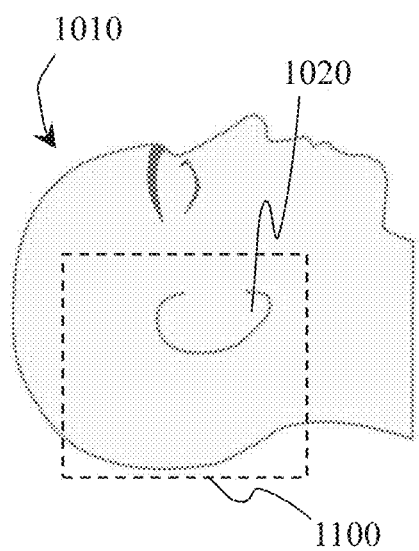
Figure 3C:
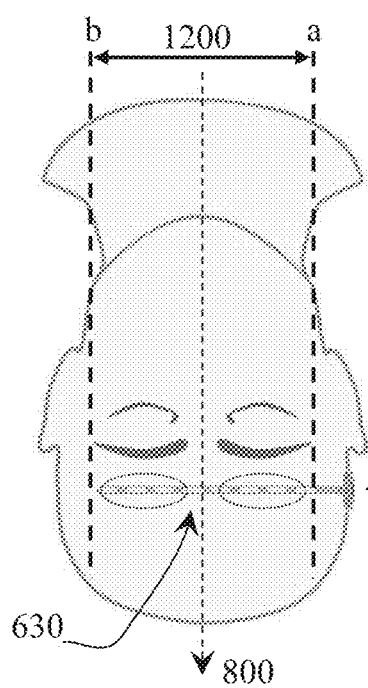
Figure 3D:
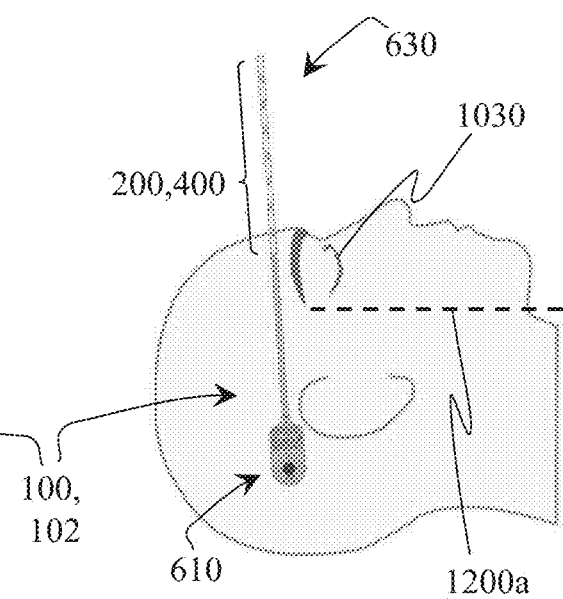
Figure 3E:
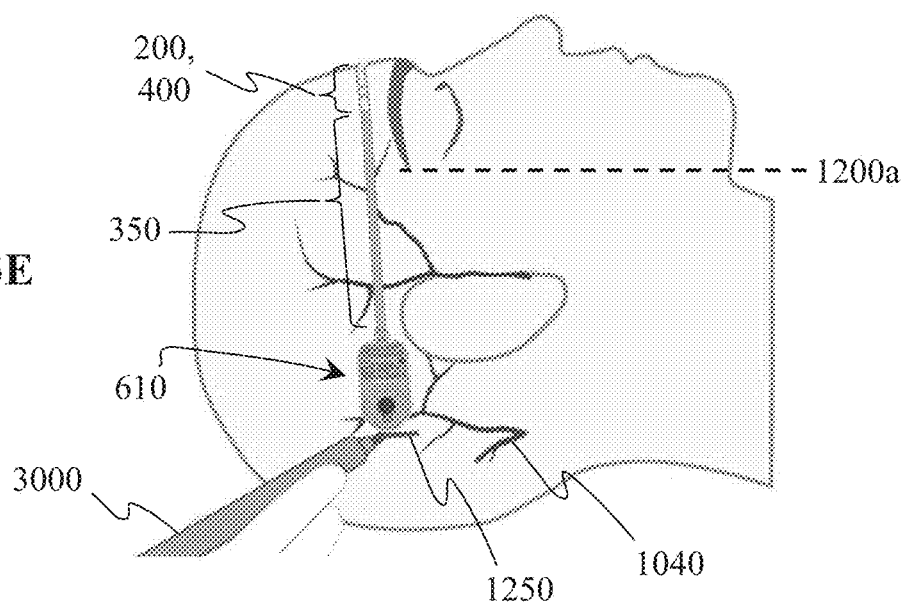
Figure 3F:
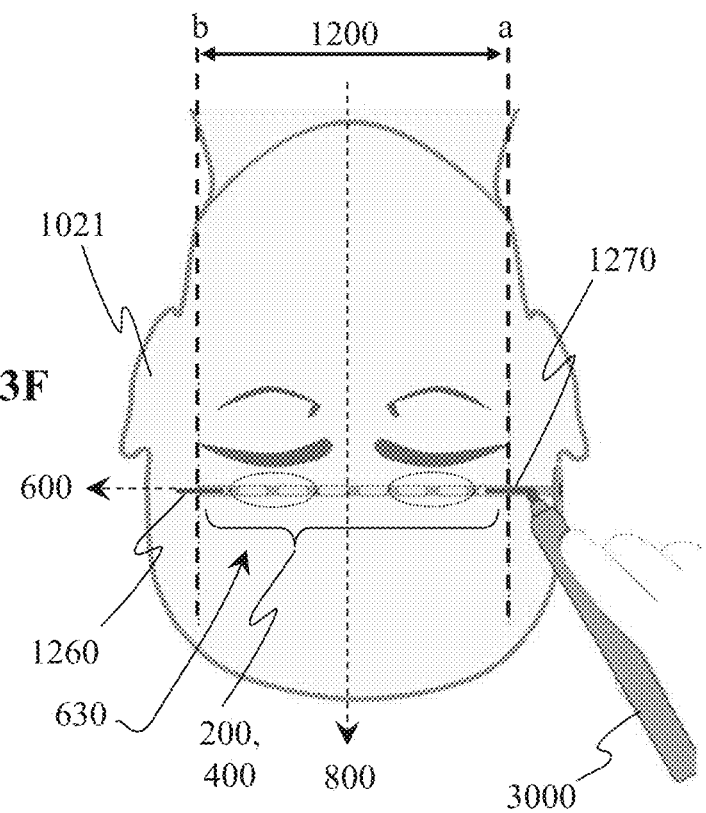
Figure 3G:
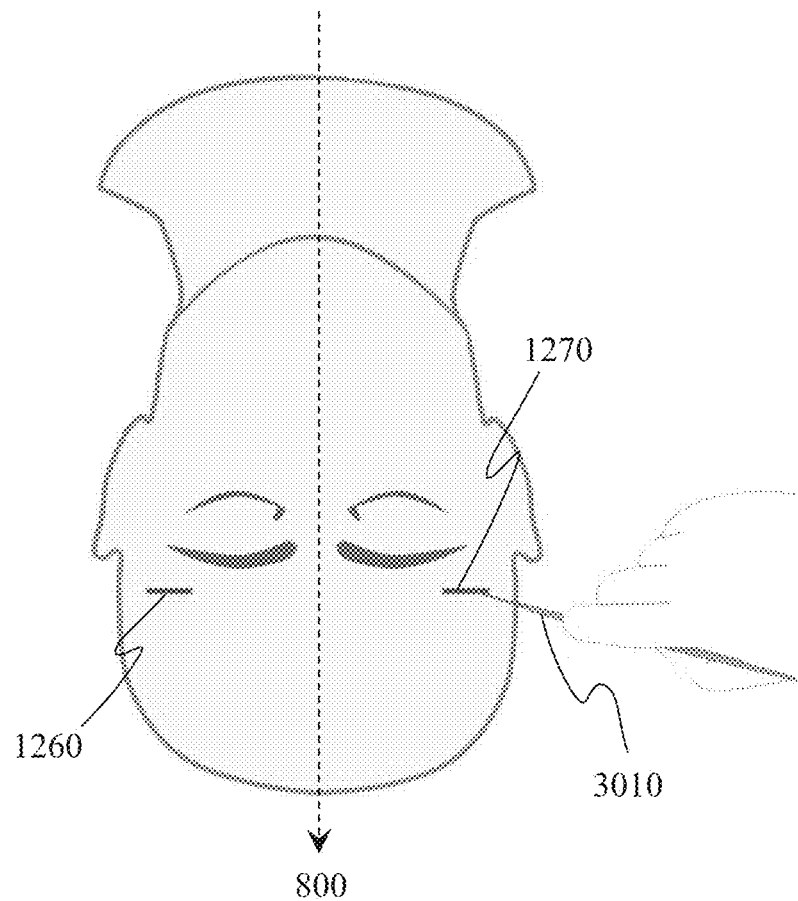
Figure 3H:
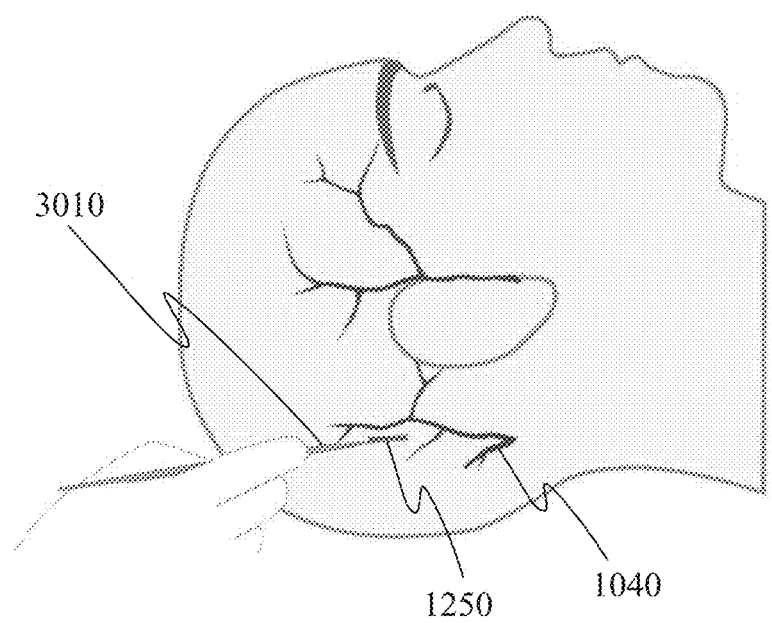
Figure 3I:
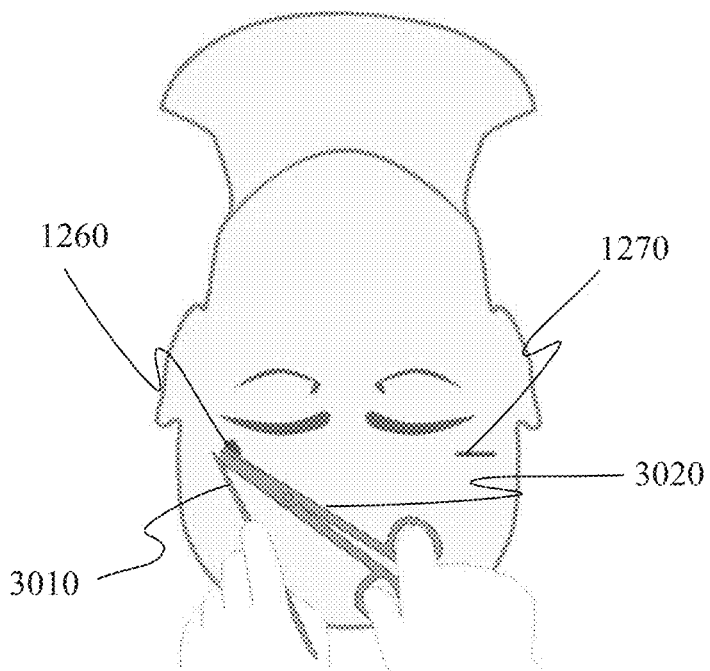
Figure 3J:
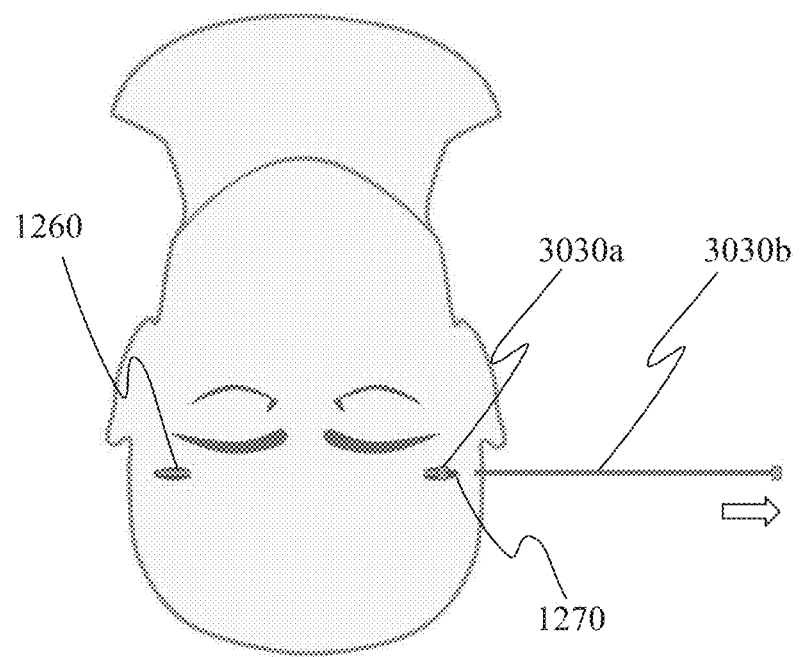
Figure 3K:
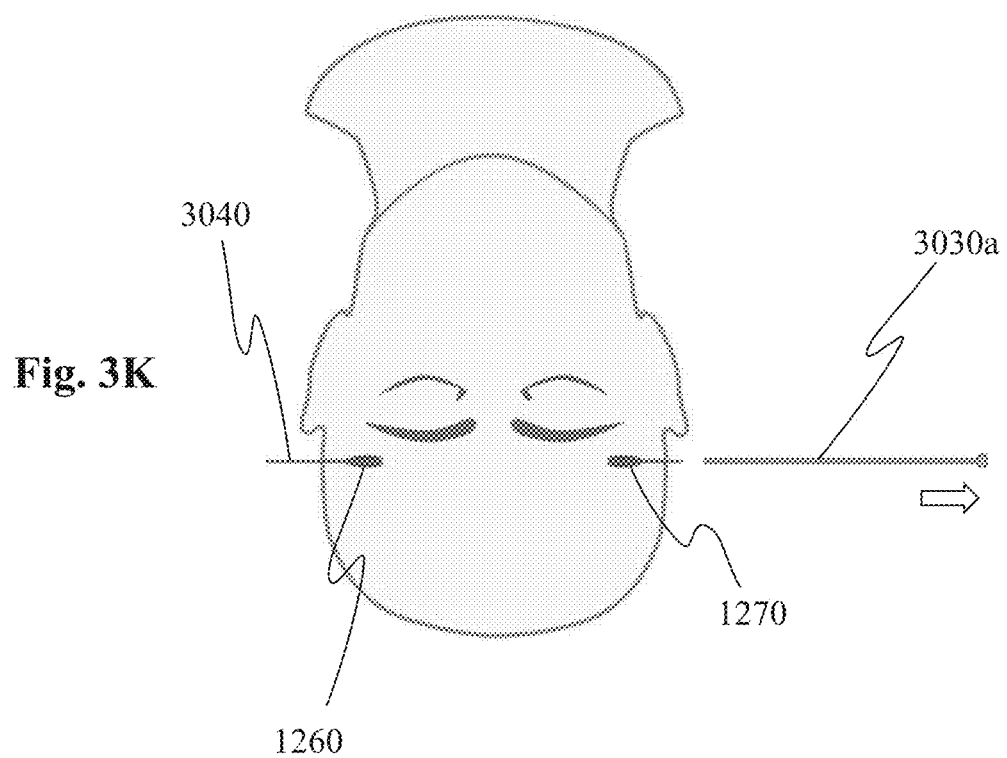
Figure 3L:
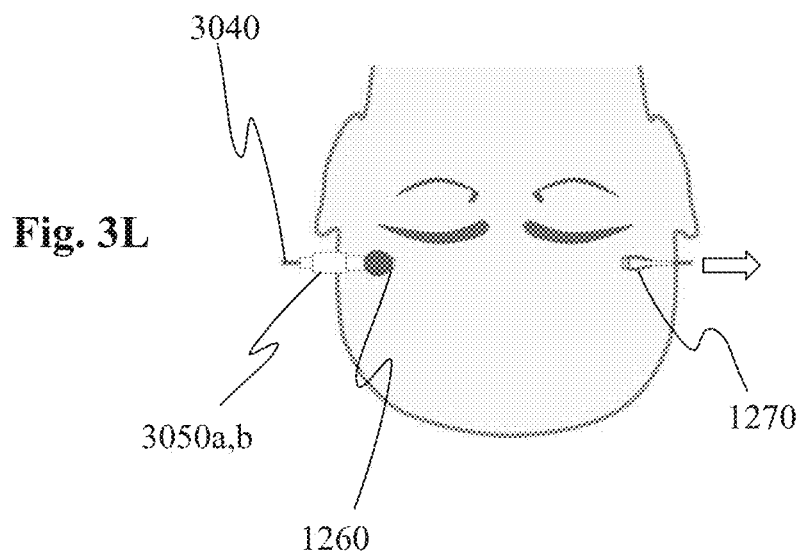
Figure 3M:
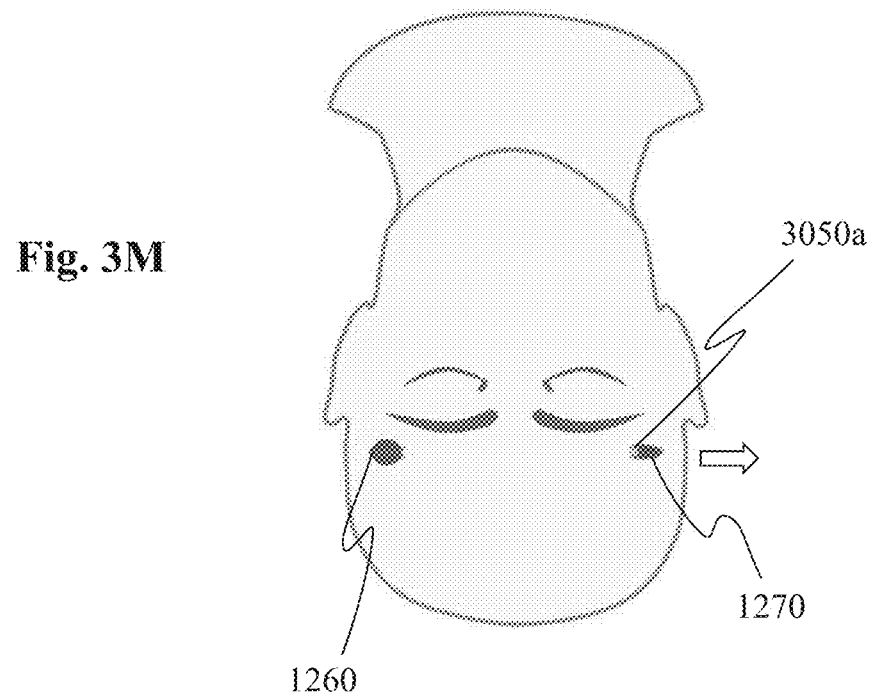
Figure 3N:
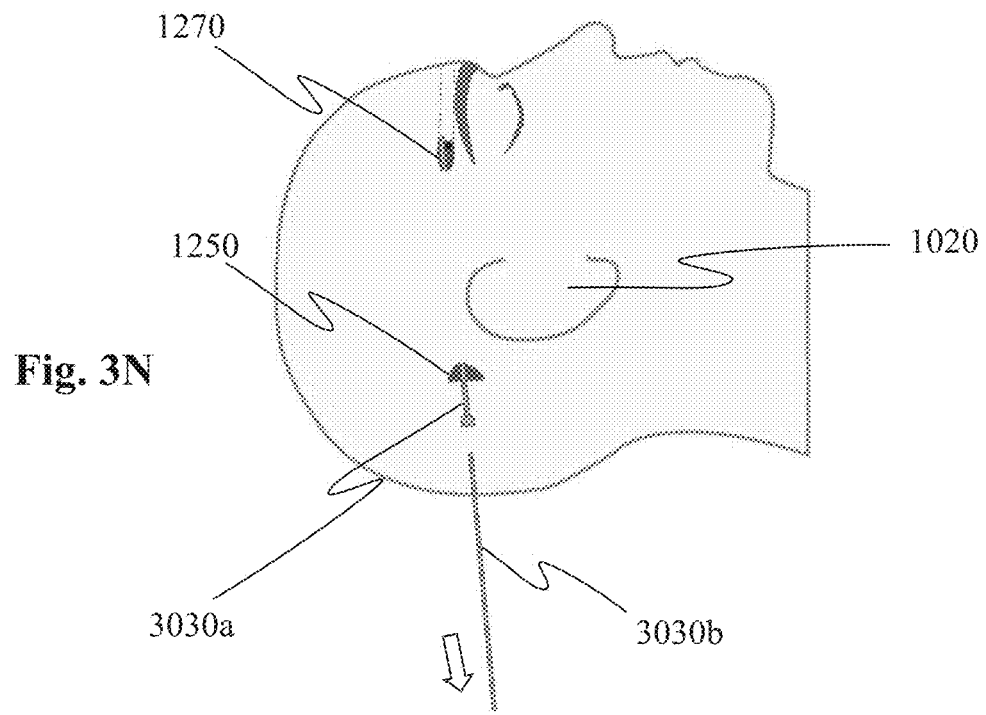
Figure 3O:
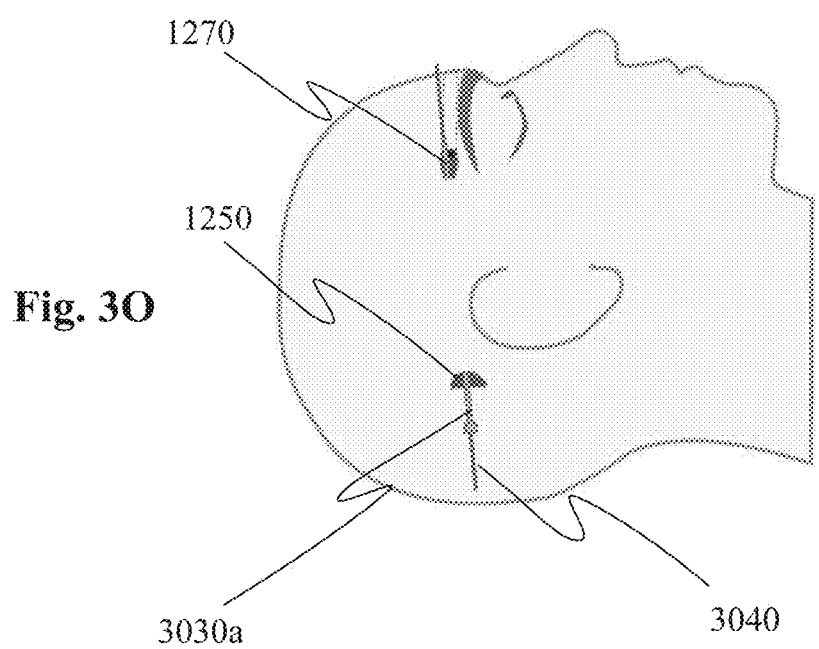
Figure 3P:
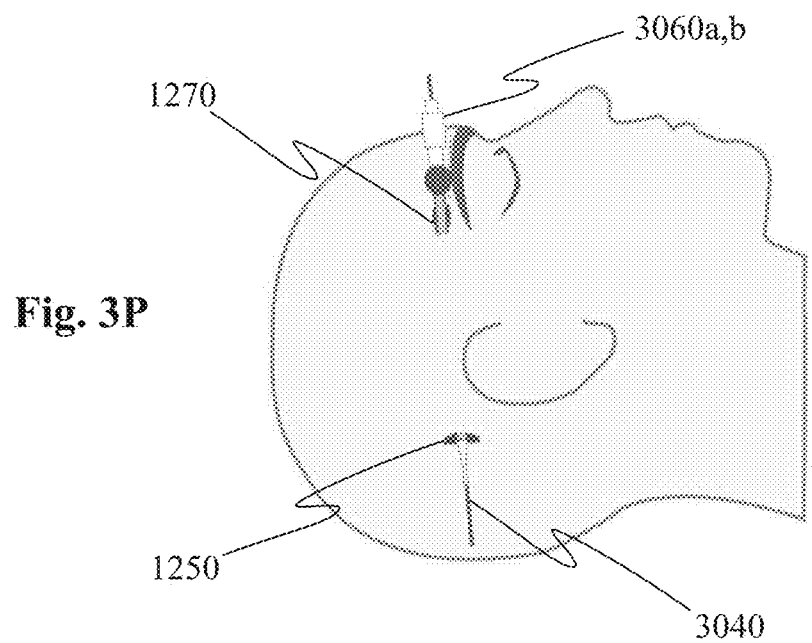
Figure 3Q:
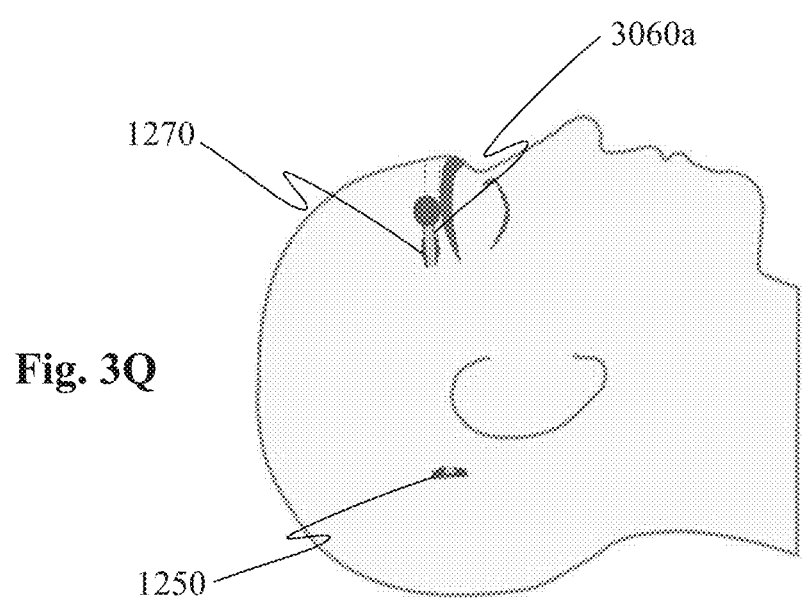
Figure 3R:
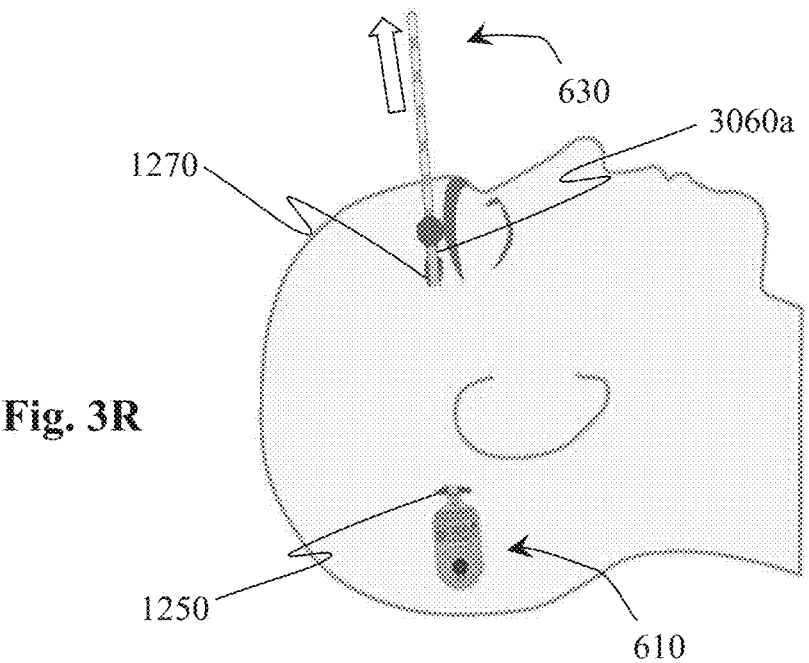
Figure 3S:
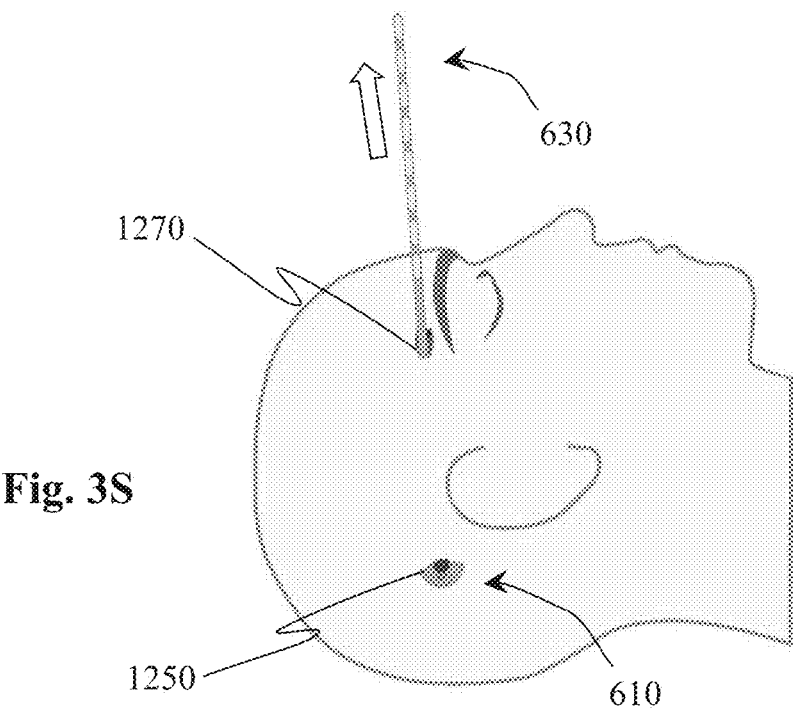
Figure 3T:
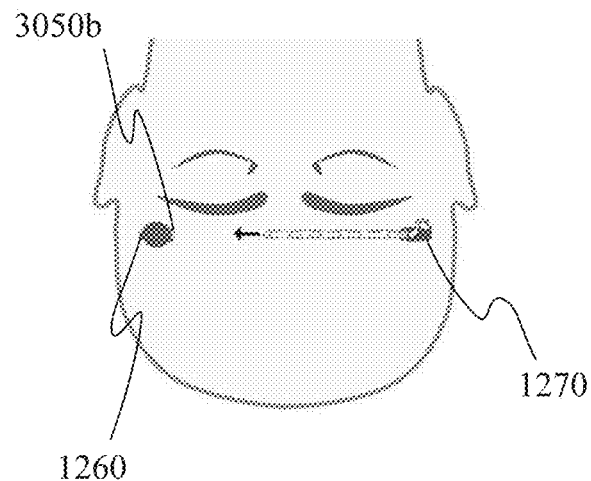
Figure 3U:
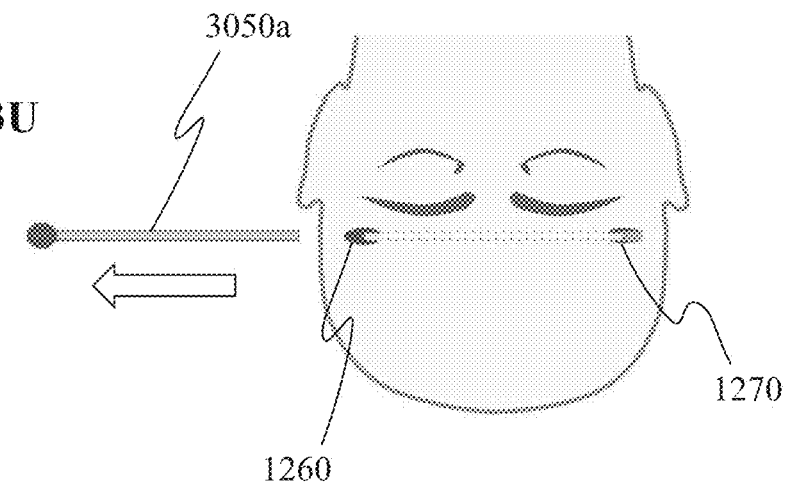
Figure 3V:
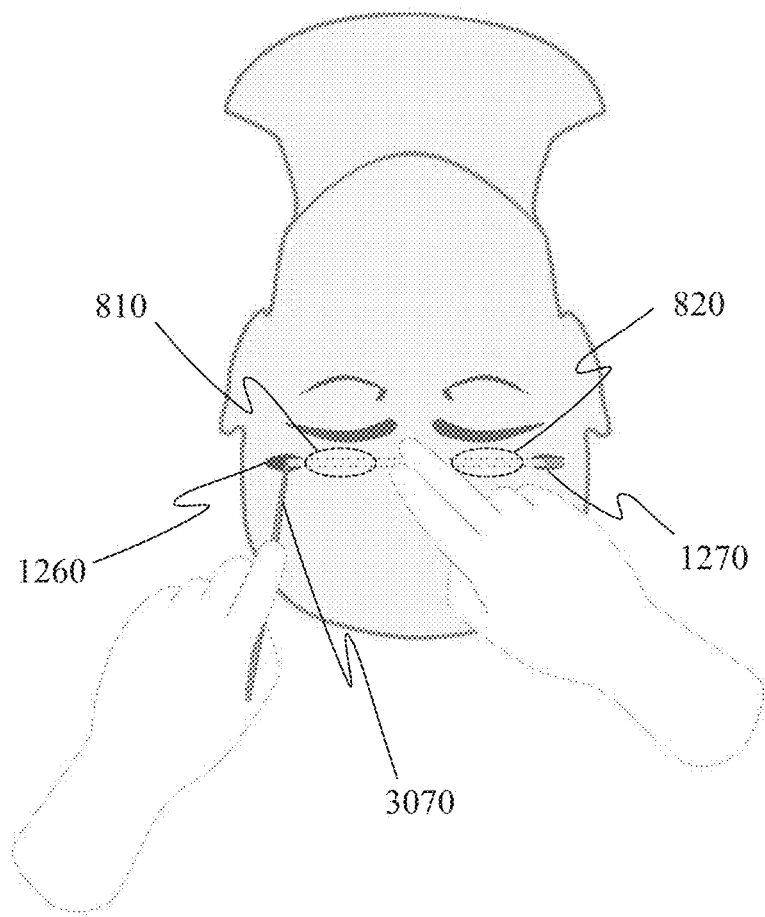

FIG. 3A-3V depict a second method to implant a stimulator, namely at a target location of disposed midway on a subject's 1000 forehead 1010 superior ("above") to the right 1030 and left orbita 1031. The disposition of the implanted stimulator is suitable for supraorbital nerve stimulation (SONS). It is similar to the first method described above in relation to FIG. 8A to 8O. The main differences are:
a further incision is used to implant along a curved portion of skin; and
the incisions for the first portion are oriented along the typical direction of wrinkles, which may reduce scarring.

Using this second method, the first embodiment 100 depicted in FIG. 1A to 1C, or the third embodiment of implantable stimulator 102 depicted in FIG. 1E, may be advantageously implanted due to the portion 350 comprising no stimulation electrodes 200. Additionally or alternatively, one or more electrodes 200, 400 in an array comprised in the second embodiment 101 may be disconnected and/or disabled to form and/or extend the portion 350.

FIGS. 3A and 3B depict a recommended starting position, viewed respectively from above the subject 1000 and the right side of the subject's 1000 head. The head of the subject is 1000 is placed in a supine position. A median plane 800 of the subject 1000 is depicted vertically in FIG. 3A, the arrow indicating the cranial direction.

As depicted, the target area for stimulation is a left supraorbital nerve 810 and/or a right supraorbital nerve 820—the first portion 630 of the implantable stimulator 100, 102 is configured and arranged to stimulate one or more regions in the forehead 1010 between the orbita 1030, 1031 and the dorsal side (top) of the skull.

It may be advantageous to initially shave the region of skin being treated, including the eyebrows (not indicated) and the areas 1100 on each side of the head around the right ear 1020 for the further portion 610—for example, see the highlighted area 1100 depicted in FIG. 3B. It will be obvious to the skilled person that the method may be mirrored such that the further portion 610 is implanted around the left ear 1021.

FIGS. 3C and 3D depict an initial positioning of the implantable stimulator 100, 102, viewed respectively from above the subject and the right side of the subject's 1000 head, to determine the positions for the incisions.

Through palpation and/or suitable scanning/imaging, the lateral borders of the orbita 1030, 1031, formed by the zygomatic bones, are used as the main anatomical landmarks to help position the stimulator 100, 102 for the second method.

The implantable stimulator 100, 102 is positioned laterally, superior ("above") to the left 1031 and right 1030 orbita, approximately perpendicular to the median plane 800, such that the first portion 630 with electrodes 200, 400 is on the forehead 1010 directly above the target locations 810, 820. In this case, the portion with at least two electrodes 200, 400 extends 1200 at least from the lateral border 1200a of the right orbita 1030 until the opposite lateral border 1200b of the left orbita 1031—FIG. 3C.

The dimensions of the portion with at least two electrodes 200, 400 may be predetermined and/or controlled as discussed above for the first method.

Additionally or alternatively, the data from specific studies may also be used, such as a Study of frontal hairline patterns for natural design and restoration; Sirinturk, Bagheri et al; Surgical and Radiologic Anatomy, vol 39, p. 679-684 (2017); DOI 10.1007/s00276-016-1771-1. In this study, they measured the average width of the forehead and specifically the supraorbital region of 200 adults. The average width of the female supraorbital region was 125.3±13 mm, and of the male supraorbital region was 133.9±15.9 mm.

The stimulator 100, 102 is flattened by the specialist over the outer surface of skin laterally from the median plane 800 to find the placement of the further portion 610 with either a pulse generator 500 or a pulse energy receiver, such as a coil. As depicted, it is on the right side of the subject's 1000 head superior ("above") to the right ear 1020. The implantable stimulator 100, 102 is preferably visually and/or manually checked to reduce the risk that the implantable stimulator substrate is strained and/or twisted along its path—FIG. 3D.

It will be obvious to the skilled person that the method may be mirrored such that the further portion 610 is implanted on the left side of the subject's 1000 head superior ("above") to the left ear 1021.

FIG. 3E depicts initial marking of an incision site. The extent 1250 of the further portion 610 is marked on the skin as a first incision mark 1250. The further portion 610 is to be implanted on the right-side of the subject 1000, superior ("above") to the right ear 1020. The first incision mark 1250 extends approximately parallel to the median plane 800. For example, a tissue marker 3000 may be used. It may also be advantageous to determine the extent and positions of vascular structures 1040 in this area—this may reduce the risk that the vascular structures 1040 are damaged during the rest of the implantation method.

FIG. 3F depicts further marking of the incision sites. A second 1260 and third 1270 incision mark is marked on the skin along the longitudinal path 600 of the portion with at least two electrodes 200, 400 portion of the implantable stimulator 100, 102 at respectively the lateral border 1200b of the left orbita 1031 and the lateral border 1200a of the right orbita 1030. The second 1260 and third 1270 incision marks extend laterally, which is approximately perpendicular to the median plane 800, in approximately the same direction as forehead wrinkles. This may increase comfort for the subject in some cases, and may reduce scarring in some cases.

Preferably, the second 1260 and third 1270 incision marks do not extend too far towards the median plane 800 because it may make the third 1270 incisions more difficult to reach (as described below) when tunneling from behind the ear towards the orbita with an guidewire introducer needle across the orbita curve. Otherwise the subcutaneous trajectory may need more force to reach the first portion 630.

FIG. 3G depicts initial incisions. Two incisions, each extending approximately twenty mm laterally, are made using a tissue knife 3010, such as a surgical scalpel. The second 1260 and third 1270 incisions are proximate the lateral borders respectively of each orbita 1031, 1030 and extend approximately perpendicular to the median plane 800.

FIG. 3H depicts a further incision. An incision, extending approximately thirty mm, is made using a tissue knife 3010 at the first incision mark 1250. The first 1250 incision depicted is on the right side of the head. The first incision 1250 extends longitudinally, approximately parallel to the median plane 800. Preferably vascular structures 1040 in this area are avoided.

FIG. 3I depicts the forming of skin pockets. Using a tissue knife 3010 and/or blunt scissors/forceps 3020, two skin pockets are created on the fascia of approximately ten mm by, for example, blunt dissection around the second 1260 and 1270 incisions.

Similarly (not depicted in FIG. 3I), a skin pocket is formed on the temporal side by, for example, blunt dissection around the first incision 1250. As the maximum transverse extent 700, 750 of the implantable stimulator at the further portion 610 is greater than the maximum transverse extent 700, 750 at the first portion 630, the skin pocket at the first incision 1250 is similarly greater than at the second 1260 and third 1270 incisions.

FIG. 3J depicts a possible preparation of the implant path. The tip of a guidewire introducer needle assembly 3030a,b, preferably as an epidural needle such as a Tuohy needle assembly, is inserted at the third incision 1270 and further inserted under the skin until the tip emerges from the second incision 1260. The guidewire introducer needle 3030a,b is preferably blunt. The guidewire introducer mandrin 3030b is removed from the guidewire introducer needle assembly 3030a,b to leave the guidewire introducer needle 3030a extending under the skin from the third incision 1270 to the second incision 1260.

As depicted in FIG. 3K, a guide wire 3040 is inserted through the guidewire introducer needle 3030a. The guidewire introducer needle 3030a is removed from under the skin to leave the guide wire 3040 extending under the skin from the third incision 1270 to the second incision 1260, extending on both sides from the incisions 1260, 1270.

As depicted in FIG. 3L, a first introducer assembly 3050a,b is inserted under the skin over the guidewire 3040 from the second incision 1260 to the third incision 1270.

As depicted in FIG. 3M, the guide wire 3040 and first introducer mandrin 3050b are removed from under the skin to leave the first introducer sheath 3050a, extending under the skin through the second incision 1260 to the third 1270 incision.

Alternatively, the first introducer assembly 3050a,b may be inserted under the skin over the guidewire 3040 from the third incision 1270 to the second incision 1260. The guide wire 3040 and first introducer mandrin 3050b may be removed from under the skin to leave the first introducer sheath 3050a, extending under the skin through the third 1270 incision to the second incision 1260 position.

As depicted in FIG. 3N, the tip of the guidewire introducer needle assembly 3030a,b is inserted at the first incision 1250 and further inserted under the skin until the tip emerges from the third incision 1270. Due to the flexibility of guidewire introducer needles in general, it is expected that the same guidewire introducer needle assembly 3030a,b may be used as described above in relation to FIGS. 3J and 3K. However, it may be advantageous to provide a further guidewire introducer needle assembly, configured and arranged to perform these actions.

The guidewire introducer mandrin 3030b is removed from the guidewire introducer needle assembly 3030a,b to leave the guidewire introducer needle 3030a extending under the skin from the first incision 1250 to the third incision 1270.

As depicted in FIG. 3O, the guide wire 3040 is inserted through guidewire introducer needle 3030a. The guidewire introducer needle 3030a is removed from under the skin to leave the guide wire 3040 extending under the skin through the first incision 1250 to the third incision 1270, extending on both sides from the incisions 1250, 1270. Due to the flexibility of guide wires in general, it is expected that the same guide wire 3040 may be used as described above in relation to FIG. 3K. However, it may be advantageous to provide a further guide wire, configured and arranged to perform these actions.

As depicted in FIG. 3P, a second introducer assembly 3060a,b is inserted under the skin over the guidewire 3040 from the third incision 1270 to the first incision 1250. The second introducer 3060*a,b* may be identical, similar or different to the first introducer 3050*a,b*. It may the same type of introducer, but with identical, similar or different dimensions.

As depicted in FIG. 3Q, the guide wire 3040 and second introducer mandrin 3060*b* are removed from under the skin to leave the second introducer sheath 3050*a*, extending under the skin through the third incision 1270 to the first incision 1250.

Alternatively, the second introducer assembly 3060*a,b* may be inserted under the skin over the guidewire 3040 from the first incision 1250 to the third incision 1270. The guide wire 3040 and second introducer mandrin 3060*b* may be removed from under the skin to leave the second introducer sheath 3060*a*, extending under the skin through the first 1250 incision to the third incision 1270 position.

As depicted in FIG. 3R, the first portion 630 of the implantable stimulator 100, 102, comprising the at least two electrodes 200, 400, is inserted into the second introducer sheath 3060*a* from the first incision 1250 to the third incision 1270. The first portion 630 of the implantable stimulator 100, 102 extends from the third incision 1270 position.

As depicted in FIG. 3S, the second introducer sheath 3060*a* is removed. The first portion 630 of the implantable stimulator 100, 102 is pulled, using, for example, tweezers or silicone-tipped tweezers 3070, such that it extends further from the third incision 1270 position, and the further portion 610 of the implantable stimulator 100, 102 with the electrical components is introduced into the ipsilateral skin pocket at the first incision 1250.

As depicted in FIG. 3T, the first portion 630 of the implantable stimulator 100, 102, comprising the portion with at least two electrodes 200, 400, that extends from the third incision 1270 is threaded through the first introducer sheath 3050*a* to the second incision 1260.

As depicted in FIG. 3U, the first introducer sheath 3050*a* is removed.

As depicted in FIG. 3V, the first portion 630 of implantable stimulator 100, 102 is pulled at the second incision 1260 using tweezers 3070. It is advantageous to check that the lead substrate is flattened underneath the skin—this may be checked visually, using palpation and optionally with a diagnostic imager, such as an x-ray imager. If the portion with at least two electrodes 200, 400 is incorrectly positioned, it may be corrected by gently pulling on the distal 630 and/or further portion 610 using silicone-tipped tweezers. Alternatively or additionally, the positioning may be corrected by gently pulling at the substrate portion accessible through the third incision 1270.

The tip of the first portion 630 is guided into the skin pocket at the second incision 1260. The first 1250, second 1260 and third 1270 incisions are closed, preferably in layers with subcutaneous and cutaneous sutures.

In this second method, similar to the first method, the dimensions of implantation tools and/or subcutaneous tunnels are typically dimensioned based on the maximum transverse cross-section 700, 730, 750 of the first portion 630, and in particular the portion with at least two electrodes 200, 400.

In this second method, the following implantation tools may be used:
- a guidewire introducer needle assembly 3030*a,b*, comprising a guidewire introducer needle 3030*a* enclosing a guidewire introducer mandrin 3030*b* (FIG. 3J). The lumen of the guidewire introducer needle 3030*a* is at least large enough to receive a suitable guide wire 3040—in other words, the guidewire introducer needle 3030*a* has a minimum internal transverse cross-section which is greater than the maximum transverse cross-section of the guide wire 3040. The length is at least the distance from the first lateral border 1200*a* to the second lateral border 1200*b*. Typically, a gauge of 20G is used. For example, an epidural needle such a Tuohy needle assembly may be used. Preferably, the guidewire introducer needle is blunt;
- a guide wire 3040 is inserted through the guidewire introducer needle 3030*a* (FIG. 3K). The guidewire introducer needle 3030*a* is removed from under the skin to leave the guide wire 3040 extending under the skin. The maximum transverse cross-section of the guide wire 3040 is at least sufficiently smaller than the inner lumen dimensions of the guidewire introducer needle 3030*a* so that the guide wire 3040 may be inserted—in other words, the guide wire 3040 has a maximum transverse cross-section less than the minimum internal transverse cross-section of the guidewire introducer needle 3030*a*. The length is at least the distance from the first lateral border 1200*a* to the second lateral border 1200*b*. Typically, a gauge of 20G may be used;
- a first introducer assembly 3050*a,b* is inserted under the skin over the guidewire 3040 (FIG. 3L). The first introducer assembly 3050*a,b* comprises a first introducer sheath 3050*a* enclosing a hollow first introducer mandrin 3050*b*. The lumen of the introducer mandrin 3050*b* is at least large enough to receive the guide wire 3040—in other words, the introducer sheath 3050*a* has a minimum internal transverse cross-section that is greater than the maximum transverse cross-section of the guide wire 3040. The length is at least the distance from the first lateral border 1200*a* to the second lateral border 1200*b*. Typically, a gauge of 20G may be used. The lumen of the first introducer sheath 3050*a* is also at least large enough to receive the first portion 630 of the implantable stimulator 100, 102—in other words, the introducer sheath 3050*a* has a minimum internal transverse cross-section that is greater than the maximum transverse cross-section of the first portion 630 of the stimulator. The method is particularly advantageous when the first introducer sheath 3050*a* has a maximum internal transverse cross-section less than the maximum proximal transverse cross-section 710 of the substrate 300;
- optionally, a further guidewire introducer needle assembly, comprising a further guidewire introducer needle enclosing a further guidewire introducer mandrin (FIG. 3N, FIG. 3O). The lumen of the further guidewire introducer needle is at least large enough to receive a further guide wire. The length is at least the distance from the first incision 1250 to the third incision 1270. Typically, a gauge of 20G is used. For example, an epidural needle such as Tuohy needle assembly may be used. Preferably, the further guidewire introducer needle is blunt. Preferably, the same guidewire introducer needle assembly 3030*a,b* is used as described above in relation to FIGS. 3J and 3K;
- a further guide wire is inserted through the further guidewire introducer needle (FIG. 3O). The further guidewire introducer needle is removed from under the skin to leave the further guide wire extending under the skin. The maximum transverse cross-section of the further guide wire is at least sufficiently smaller than the inner lumen dimensions of the further guidewire introducer needle so that the further guide wire may be inserted—in other words, the further guide wire has a maximum transverse cross-section less than the minimum internal transverse cross-section of the further guidewire introducer needle. The length is at least the distance from the first incision 1250 to the third incision 1270. Typically, a gauge of 20G is used; Preferably, the same guide wire 3040 is used as described above in relation to FIG. 3K; and a second introducer assembly 3060*a,b* is inserted under the skin over the further guidewire (FIG. 3P). The second introducer assembly 3060*a,b* comprises a second introducer sheath 3060*a* enclosing a hollow second introducer mandrin 3060*b*. The lumen of the second introducer mandrin 3060*b* is at least large enough to receive the further guide wire—in other words, the second introducer sheath 3060*a* has a minimum internal transverse cross-section that is greater than the maximum transverse cross-section of the further guide wire. The length is at least the distance from the first incision 1250 to the third incision 1270. Typically, a gauge of 20G is used. The lumen of the second introducer sheath 3060*a* is also at least large enough to receive the first portion 630 of the implantable stimulator 100, 102—in other words, the second introducer sheath 3060*a* has a minimum internal transverse cross-section that is greater than the maximum transverse cross-section of the first portion 630 of the stimulator. The method is particularly advantageous when the second introducer sheath 3060*a* has a maximum internal transverse cross-section less than the maximum proximal transverse cross-section 710 of the substrate 300. The second introducer 3060*a,b* may be identical, similar or different to the first introducer 3050*a,b*. It may the same type of introducer, but with identical, similar or different dimensions.

In summary, the method comprises at least the steps of:
identifying a target location for stimulation;
forming a first 1250 and second 1260 incision on opposite sides of the target location;
forming a third 1270 incision between the first 1250 and second 1260 incisions;
introducing the first introducer sheath 3050*a* under the skin from the second incision 1260 to the third incision 1270;
introducing a second introducer sheath 3060*a* under the skin from the third incision 1270 to the first incision 1250, the first and second introducer sheaths 3050*a*, 3060*a* having maximum internal transverse cross-section less than the maximum proximal transverse cross-section 710 of the substrate 300;
introducing the first portion 630 of the implantable stimulator 100, comprising the at least two electrodes 200, 400, into the second introducer sheath 3060*a* from the first incision 1250 to the third incision 1270;
removing the second introducer sheath 3060*a*;
introducing the first portion 630 of the implantable stimulator 100, comprising the at least two electrodes 200, 400, into the first introducer sheath 3050*a* from the third incision 1270 to the second incision 1260; and
removing the first introducer sheath 3050*a*, whereby the implantable stimulator extends under the skin from the further portion 610 at the first incision 1250 to the first portion 630 at the second incision 1260.

whereby the at least two electrodes 200, 400 are arranged to transfer treatment energy to the target location.

So, using a first and second introducer sheath 3050*a*, 3060*a* and three incisions 1250, 1260, 1270, the stimulator 100, 101, 102, 103, 104, 105, may be implanted at many target locations in the body of the subject where the further portion 610 and first portions 630 are to be implanted over at least one portion of curved skin.

The methods described above using one or more introducer sheaths may be used to reliably position a stimulation device at an implantation site sufficiently close to the nerve to be stimulated. Additionally, the methods described below for reliably implanting under the nerve may be used to further improve the introducer sheath methods.

A further complication is determining a suitable subcutaneous depth for the portion with at least two electrodes 200, 400.

Figure 2A:
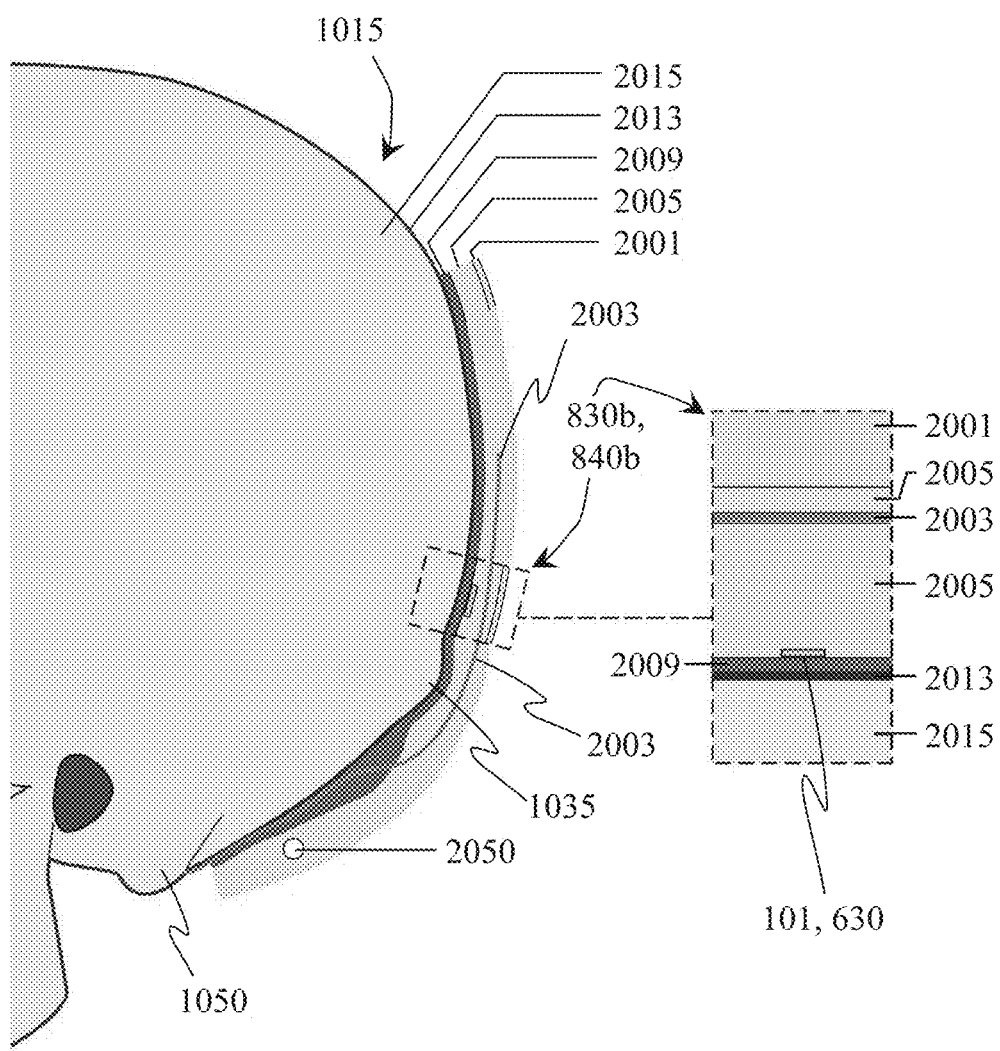
FIG. 2A depicts a transverse cross-section through the head of a subject in the target region for occipital nerve stimulation.

FIG. 2A depicts a transverse cross-section through the head of a subject 1000 in a median plane. In particular, it depicts in transverse cross-section, the layers of skin typically found at the back 1015 of the subject's 1000 head in the target region for left occipital nerve 830*b* stimulation and/or right occipital 840*b* nerve stimulation. Anatomical landmarks also depicted are the mastoid process 1050 and the (external) occipital protuberance inion 1035.

At this target location 830*b*, 840*b* for stimulation, superior ("above") to the mastoid process 1050 and superior ("above") to the occipital protuberance inion 1035, the skin comprises a plurality of layers, including (in order of increasing depth from outer to inner): an outer skin layer 2001, subcutaneous fat 2005 surrounding the nerve tissue 2003 to be stimulated, an (inner) aponeurosis layer 2009 and underlying bone tissue 2015.

In more detail, the skin at this target location may include (in order of increasing depth from outer to inner): an outer skin layer 2001, subcutaneous fat 2005 surrounding the nerve tissue 2003 to be stimulated, an (inner) aponeurosis layer 2009, a periosteum layer 2013 and underlying bone tissue 2015.

In general, aponeurosis 2009 is a type or a variant of the deep fascia that attaches sheet-like muscles needing a wide area of attachment. Their primary function is to join muscles and the body parts they act upon, whether bone or other muscles.

In general, fascia is a band or sheet of connective tissue, primarily collagen, beneath the skin that attaches, stabilizes, encloses, and separates muscles and other internal organs.

Skin layers may also include one or more layers of connective tissue and/or one or more layers of fascia. For clarity, these have not been included in the drawings, and are not discussed in detail in this application.

The implantation method therefore comprises:
forming one or more 1250, 1260, 1270 incisions proximate the target location;
removing one or more skin layers, including an outer skin layer 2001 and subcutaneous fat 2005; and
introducing the first portion 630 in the skin whereby the at least two electrodes 200, 400 are disposed between the nerve tissue 2003 to be stimulated and the aponeurosis layer 2009. The first portion 630 may be disposed above the aponeurosis layer 2009.

As the skin layers are removed one-by-one, it is relatively straightforward for the specialist to identify the transition between the subcutaneous fat layer 2005 and the underlying tissue, such as the aponeurosis layer 2009 and/or the periosteum layer 2013.

Aponeurosis 2009 appears to be shiny, with a whitish-silvery color. The layers 2009 are usually very sparingly supplied with blood vessels and nerves.

By introducing the first portion 630 below the subcutaneous fat layer 2005 in a region with aponeurosis 2009, the chance that the first portion 630 is implanted under the nerve tissue 2003 to be stimulated is very high.

This has the advantage over other proposed locations for stimulator implantations. Conventionally, stimulators are often implanted in the subcutaneous fat layer 2005 in locations 2050 closer but superior ("above") to the mastoid process 1050. The mastoid process 1050 is located posterior and inferior ("below") to the ear canal, lateral to the styloid process, and appears as a conical or pyramidal projection. These proposed locations 2050 are inferior ("below") to the occipital protuberance inion 1035.

At this conventional location 2050, the skin comprises a different plurality of layers (in order of increasing depth from outer to inner): an outer skin layer 2001, subcutaneous fat 2005, muscle tissue 2019 surrounding the nerve tissue 2003 to be stimulated, a periosteum layer 2013 and underlying bone tissue 2015.

A frequent disadvantage of such conventional locations 2050 is the extended distance to the nerve tissue to be stimulated, which typically requires a higher level of energy to be transferred into tissue, which may reduce energy efficiency. This may also result in unwanted stimulation of muscle tissue 2019 disposed between the nerve 2003 and the stimulator 2050.

Aponeurosis 2009 is mainly found at skin locations where there is little or no muscle tissue 2019. So by selecting locations where aponeurosis 2009 is present, the risk that muscle tissue 2019 is disposed between the stimulator 101 and the nerve tissue 2003 to be stimulated is greatly reduced.

In addition, the risk of unwanted muscle stimulation may be reduced due to the reduced risk of being close to muscle tissue 2019.

It may be advantageous to introduce the first portion 630 such that the at least two electrodes 200, 400 is disposed in skin layers directly adjacent to or in the aponeurosis layer 2009. There are fewer blood vessels, so the risk of damage to other anatomical structures may also be reduced. For example:

between subcutaneous fat 2005 and the aponeurosis layer 2009;

directly adjacent to the aponeurosis layer 2009;

in the aponeurosis layer 2009.

It therefore reduces the risk even further that the first portion 630 is inserted over the nerve tissue 2003 to be stimulated. In this context, "under" the nerve 2003 is a skin depth location between the nerve tissue 2003 and the underlying bone tissue 2015, and "over" the nerve 2003 is a skin depth location between the nerve tissue 2003 and an outer skin layer 2001.

By being implanted deeper, comfort for the subject may be improved. In addition, if it the chance that the stimulator is implanted under the nerve tissue is relatively high, it may allow a first portion with electrodes on only one surface (either the first or second surface) to be more reliably used.

It is advantageous to implant any type of stimulator with one or more stimulation electrodes under the occipital nerve tissue 2003 to be stimulated. Particularly advantageous is to implant the first portion 630 of a stimulator as disclosed herein 100, 101, 102, 103, 104, 105 under the nerve tissue 2003 to be stimulated. It is even more advantageous to use the method depicted in FIG. 8A to FIG. 8O and described above.

By using a first portion 630 with a greatly reduced thickness, such as 0.5 mm or less, introduction deeper under the skin becomes possible. Additionally or alternatively, comfort for the subject may be improved if the stimulator 101 is located deeper under the skin.

By using a conformable first portion 630, insertion may be made more precisely at the interfaces between skin layers—the risk may be reduced of tissue damage during insertion, and the conformable first portion 630 may more easily follow anatomical curvature.

Figure 2B:
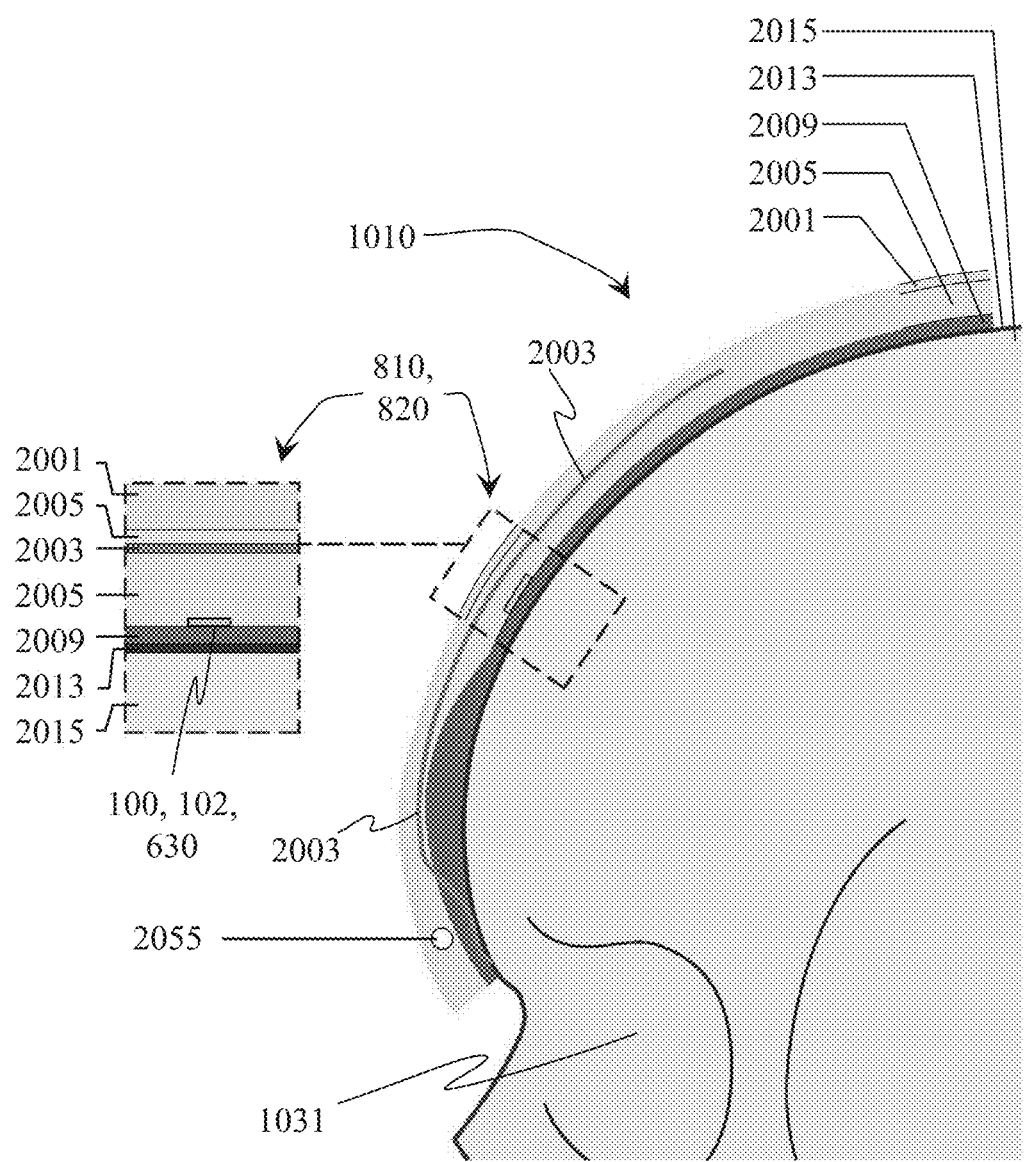
FIG. 2B depicts a transverse cross-section through the head of a subject in the target region for supraorbital nerve stimulation.

FIG. 2B depicts a transverse cross-section through the head of a subject 1000 in a median plane. In particular, it depicts in transverse cross-section, the layers of skin typically found at the forehead 1010 of a subject 1000 in the target region for left supraorbital nerve 810 stimulation and/or right supraorbital 820 nerve stimulation.

At this target location 810, 820 for stimulation, superior ("above") to the orbita 1031, the skin comprises a plurality of layers, including (in order of increasing depth from outer to inner): an outer skin layer 2001, nerve tissue 2003 to be stimulated, an (inner) aponeurosis layer 2009 and underlying bone tissue 2015.

In more detail, the skin at this target location may include (in order of increasing depth from outer to inner): an outer skin layer 2001, subcutaneous fat 2005 surrounding the nerve tissue 2003 to be stimulated, an (inner) aponeurosis layer 2009, a periosteum layer 2013 and underlying bone tissue 2015.

These are the same layers as described above for FIG. 2A, so the advantages and disadvantages discussed are also the same.

The target locations 810, 820 have the advantage over other proposed locations for stimulator implantations. Conventionally, stimulators are often implanted in the subcutaneous fat layer 2005 in locations closer (less superior) to the orbita 1031.

At these conventional locations 2055, the skin comprises a different plurality of layers (in order of increasing depth from outer to inner): an outer skin layer 2001, subcutaneous fat 2005, muscle tissue 2019 surrounding the nerve tissue 2003 to be stimulated, a periosteum layer 2013 and underlying bone tissue 2015.

These are the same layers as described above for FIG. 2A, so the disadvantages discussed are also the same.

It is advantageous to implant any type of stimulator with one or more stimulation electrodes under the supraorbital nerve tissue 2003 to be stimulated. Particularly advantageous is to implant the first portion 630 of a stimulator as disclosed herein 100, 101, 102, 103, 104, 105 under the nerve tissue 2003 to be stimulated. It is even more advantageous to use the method depicted in FIG. 3A to FIG. 3V and described above.

Figure 2C:
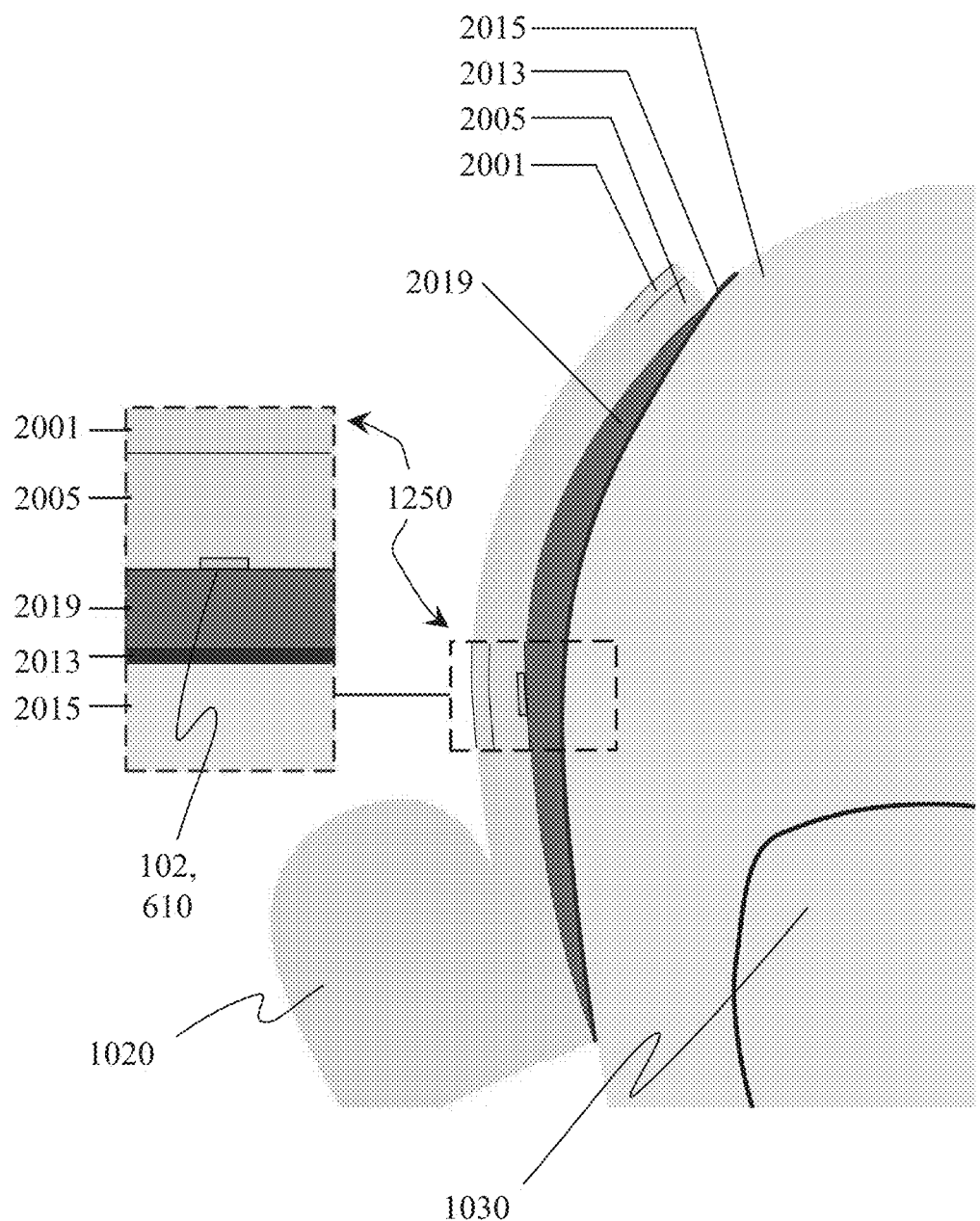
FIG. 2C depicts a transverse cross-section through the head of a subject in a convenient region for the further portion to be implanted.

FIG. 2C depicts a transverse cross-section through the head of a subject 1000 in a coronal plane. The coronal plane or frontal plane divides the head into front and back parts.

In particular, it depicts in transverse cross-section, the layers of skin typically found superior ("above") to the right ear 1020 of a subject 1000 in a convenient region for the further portion 610 to be implanted. In this example, it depicts a cross-section through the first incision 1250 depicted in FIG. 3A to 3V.

At this convenient location, the skin comprises a plurality of layers, including (in order of increasing depth from outer to inner): an outer skin layer 2001, muscle tissue 2019, and underlying bone tissue 2015.

In more detail, the skin at this target location may include (in order of increasing depth from outer to inner): an outer skin layer 2001, a subcutaneous fat layer 2005, muscle tissue 2019, a periosteum layer 2013 and underlying bone tissue 2015.

These are similar layers as described above for FIG. 2A and FIG. 2B, so the advantages and disadvantages discussed are also the same. At these locations, muscle tissue 2019 is present, so there is little or no aponeurosis 2009. It is also preferably a region selected with little or no nerve tissue, so it is not necessary to take this into account when determining the implantation depth. In particular, insertion close to the interface between the subcutaneous fat layer 2005 and the underlying tissue layers 2019, 2013 generally requires less force to be applied.

The implantation method of the further portion 610 therefore comprises:
  forming an incision 1250 proximate the implantation location;
  removing one or more skin layers, including an outer skin layer 2001 and subcutaneous fat 2005; and
  introducing the further portion 610 of the substrate 300 in the skin layers, whereby the further portion 610 is disposed between subcutaneous fat 2005 and above or in muscle tissue 2019.

This may allow a more complete implantation of the implantable stimulator, which may reduce infection risk, and may increase the positional stability of the first portion 630.

As the skin layers are removed one-by-one, it is relatively straightforward for the specialist to identify the transition between the subcutaneous fat layer 2005 and the underlying tissue, such as muscle tissue 2019 and/or the periosteum layer 2013.

Conventionally, implants are implanted just under the outer layer of skin 2001. However, by implanting deep or below subcutaneous fat 2005, comfort may be improved for the subject as the further portion 610 is covered by more skin layers. It may also be advantageous for the specialist to implant the first portion 630 and further portion 610 at approximately the same depth in the skin.

In embodiments where the further portion 610 is also implanted, it may be advantageous for the further portion 610 to be disposed above or in the muscle tissue 2019. For example:
  between the subcutaneous fat layer 2005 and the aponeurosis layer 2009;
  adjacent to the muscle tissue 2019;
  in the muscle tissue 2019.

Deeper locations may increase the amount of skin layers that cover the further portion 610, which may further increase comfort for the subject.

It is advantageous to implant any type of stimulator with a further portion directly adjacent or in muscle 2019. Particularly advantageous is to implant the further portion 610 of a stimulator as disclosed herein 100, 101, 102, 103, 104, 105. It is even more advantageous to use the methods depicted in FIG. 3A to FIG. 3V or FIG. 8A to 8O, as described above.

The methods described above may be used to reliably implant below the nerve tissue to be stimulated. Additionally, the methods described above using one or more introducer sheaths may be used to further improve the under-nerve implantation methods.

Figure 5:
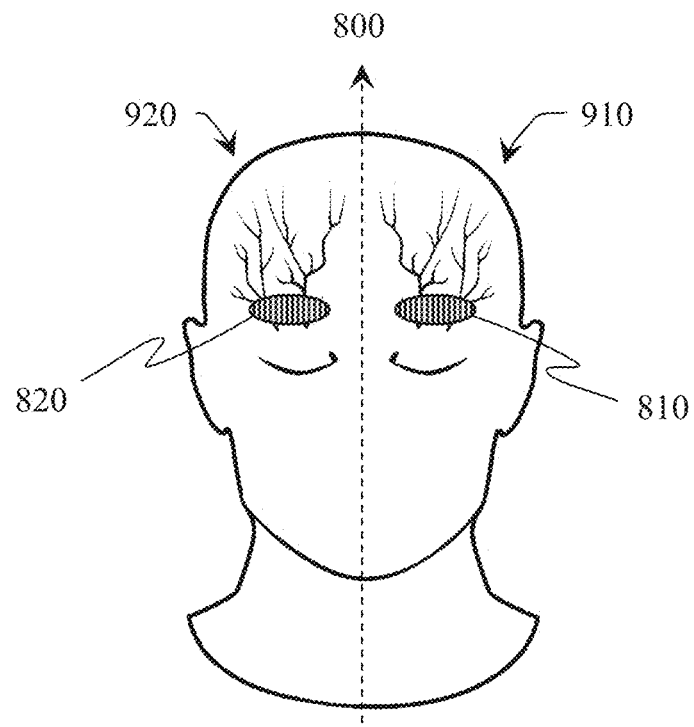
FIG. 5 and FIG. 6 depict examples of nerves that may be stimulated to treat headaches.

FIG. 5 and FIG. 6 depict examples of nerves that may be stimulated using a suitably configured implantable first portion of stimulators 100, 101, 102, 103, 104, 105 to provide neurostimulation to treat, for example, headaches or primary headaches.

FIG. 5 depicts the left supraorbital nerve 910 and right supraorbital nerve 920 which may be electrically stimulated using a suitably configured device. FIG. 6 depicts the left greater occipital nerve 930 and right greater occipital nerve 940 which may also be electrically stimulated using a suitably configured device.

Depending on the size of the region to be stimulated and the dimensions of the portions of the device to be implanted, a suitable location may be determined to provide the electrical stimulation required for the treatment. For example, one or more of:
  if an appropriate location can be found to make the pocket for the further portion 610, then the stimulator 100, 101, 102, 103, 104, 105, may be implanted using an introducer sheath 3050a and two incisions 1250, 1260;
  if the specialist wishes to position the further portion further away, or the region of skin is curved, then the stimulator 100, 101, 102, 103, 104, 105, using a first and second introducer sheath 3050a, 3060a and three incisions 1250, 1260, 1270.

Approximate implant locations for the distal part of the stimulation device comprising stimulation devices 100, 101, 102, 103, 104, 105 are depicted in FIG. 5 and FIG. 6 as regions:
  location 810 for left supraorbital stimulation and location 820 for right supraorbital stimulation for treating chronic headache such as migraine and cluster.
  location 830a or location 830b for left occipital stimulation and location 840a or location 840b for right occipital stimulation for treating chronic headache such as migraine, cluster, and occipital neuralgia.

In many cases, these will be the approximate locations 810, 820, 830a/b, 840a/b for the implantable stimulator 100, 101, 102, 103, 104, 105.

For each implant location, 810, 820, 830a/b, 840a/b a separate stimulation system may be used. Where implant locations 810, 820, 830a/b, 840a/b are close together, or even overlapping, a single stimulation system may be configured to stimulate at more than one implant location 810, 820, 830a/b, 840a/b by increasing the length of the substrate 300 and/or the length of the portion with at least two electrodes 200, 400.

A plurality of stimulation devices 100, 101, 102, 103, 104, 105 may be operated separately, simultaneously, sequentially or any combination thereof to provide the required treatment.

Figure 7:
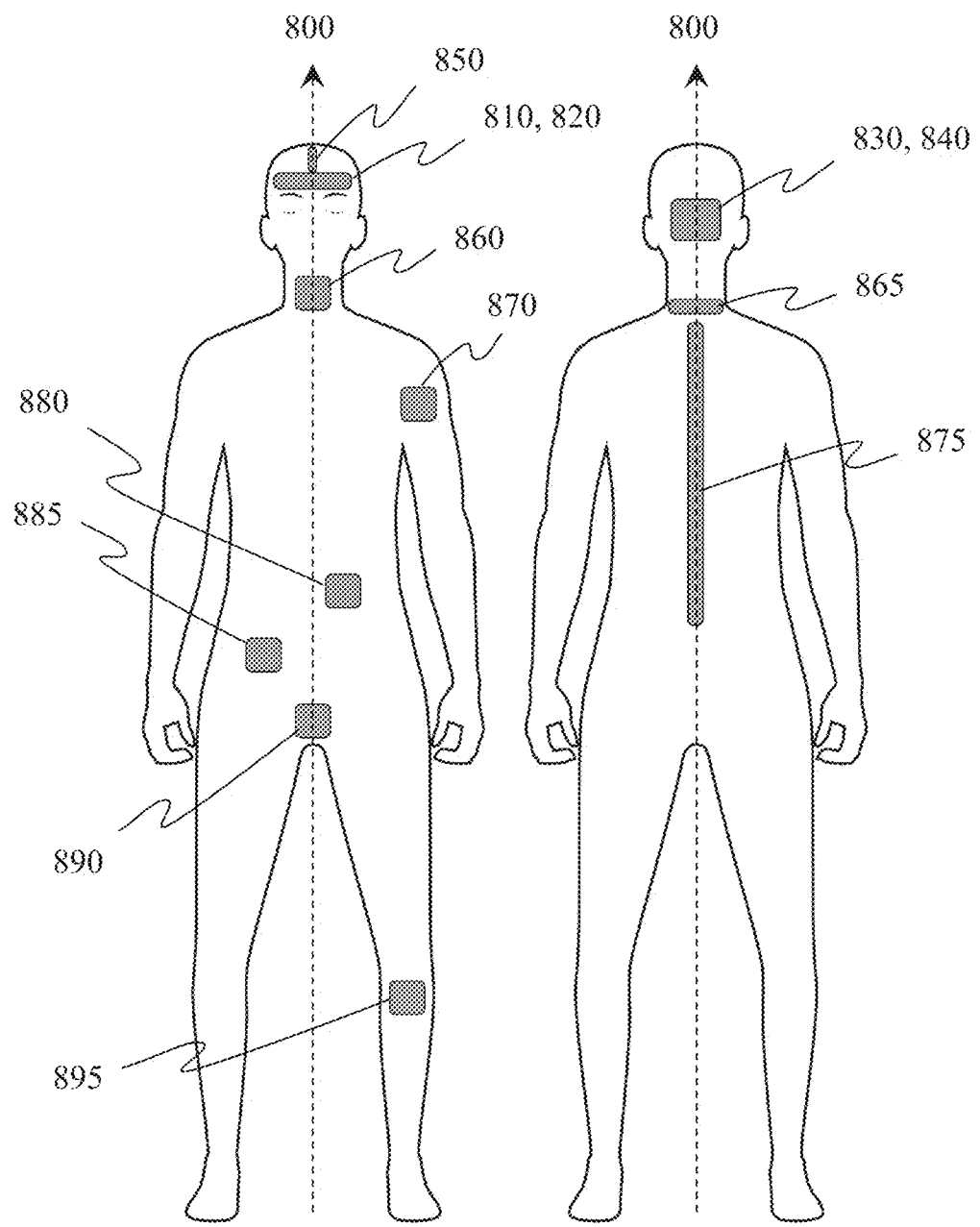
FIG. 7 depicts examples of nerves that may be stimulated for other treatments.

FIG. 7 depict further examples of nerves that may be stimulated using a suitably configured improved implantable stimulator 100, 101, 102, 103, 104, 105 to provide neurostimulation to treat other conditions. The locations depicted in FIG. 5 and FIG. 6 (810, 820, 830, 840) are also depicted in FIG. 7.

Depending on the size of the region to be stimulated and the dimensions of the part of the device to be implanted, a suitable location is determined to provide the electrical stimulation required for the treatment. Approximate implant locations for the part of the stimulation device comprising stimulation electrodes are depicted as regions:
  location 810 for cortical stimulation for treating epilepsy;
  location 850 for deep brain stimulation for tremor control treatment in Parkinson's disease patients; treating dystonia, obesity, essential tremor, depression, epilepsy, obsessive compulsive disorder, Alzheimer's, anxiety, bulimia, tinnitus, traumatic brain injury, Tourette's, sleep disorders, autism, bipolar; and stroke recovery
  location 860 for vagus nerve stimulation for treating epilepsy, depression, anxiety, bulimia, obesity, tinnitus, obsessive compulsive disorder, heart failure, Crohn's disease and rheumatoid arthritis;

location 860 for carotid artery or carotid sinus stimulation for treating hypertension;

location 860 for hypoglossal & phrenic nerve stimulation for treating sleep apnea;

location 865 for cerebral spinal cord stimulation for treating chronic neck pain;

location 870 for peripheral nerve stimulation for treating limb pain, migraines, extremity pain;

location 875 for spinal cord stimulation for treating chronic lower back pain, angina, asthma, pain in general;

location 880 for gastric stimulation for treatment of obesity, bulimia, interstitial cystitis;

location 885 for sacral & pudendal nerve stimulation for treatment of interstitial cystitis;

location 885 for sacral nerve stimulation for treatment of urinary incontinence, fecal incontinence;

location 890 for sacral neuromodulation for bladder control treatment; and location 895 for fibular nerve stimulation for treating gait or footdrop.

Other condition that may be treated include gastroesophageal reflux disease, an autoimmune disorder, inflammatory bowel disease and inflammatory diseases.

Depending on the size of the region to be stimulated and the dimensions of the portions of the device to be implanted, a suitable location may be determined to provide the electrical stimulation required for the treatment. For example, one or more of:

if an appropriate location can be found to make the pocket for the further portion 610, then the stimulator 100, 101, 102, 103, 104, 105, may be implanted using an introducer sheath 3050*a* and two incisions 1250, 1260;

if the specialist wishes to position the further portion further away, or the region of skin is curved, then the stimulator 100, 101, 102, 103, 104, 105, using a first and second introducer sheath 3050*a*, 3060*a* and three incisions 1250, 1260, 1270.

in many cases, appropriate locations can also be found where the at least two electrodes 200, 400 are disposed under the nerve tissue 2003 to be stimulated and above or in the aponeurosis layer 2009.

The conformability and minimum thickness of the substrate 100 and portion with at least two electrodes 200, 400 makes one or more implantable stimulators 100, 101, 102, 103, 104, 105 highly advantageous for the stimulation of one or more nerves, one or more muscles, one or more organs, spinal cord tissue, brain tissue, one or more cortical surface regions, one or more sulci, and any combination thereof.

The descriptions thereof herein should not be understood to prescribe a fixed order of performing the method steps described therein. Rather the method steps may be performed in any order that is practicable. Similarly, the examples are used to explain the algorithm, and are not intended to represent the only implementations of these algorithms—the person skilled in the art will be able to conceive many different ways to achieve the same functionality as provided by the embodiments described herein.

Many types of implantable first portions of stimulation devices are depicted. But this does not exclude that the rest of the device is implanted. This should be interpreted as meaning that at least the electrode portion of the first portion is preferably configured and arranged to be implanted.

The invention is not limited to the particular embodiments illustrated in the drawings and described above in detail. Those skilled in the art will recognize that other arrangements could be devised, for example:

one or more electrodes of the first type 200*a*, 200*b* are comprised in the first surface 310 and one or more electrodes of the second type 400*a*, 400*b* are comprised in the second surface 320; or one or more electrodes of the first type 200*a*, 200*b* are comprised in the first surface 310 and one or more electrodes of the second type 400*a*, 400*b* are also comprised in the first surface 310; or one or more electrodes of the first type 200*a*, 200*b* are comprised in the second surface 320 and one or more electrodes of the second type 400*a*, 400*b* are comprised in the first surface 310; or one or more electrodes of the first type 200*a*, 200*b* are comprised in the second surface 320 and one or more electrodes of the second type 400*a*, 400*b* are also comprised in the second surface 320; or any combination thereof.

Figure 4A:
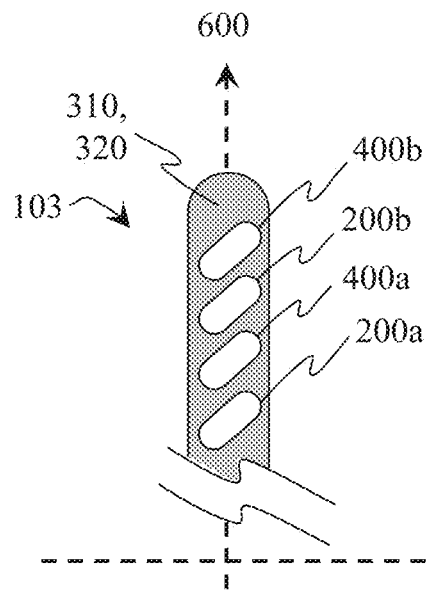
FIGS. 4A, 4B and 4C depict alternative electrode configurations suitable for being comprised in an implantable stimulator.
Figure 4B:
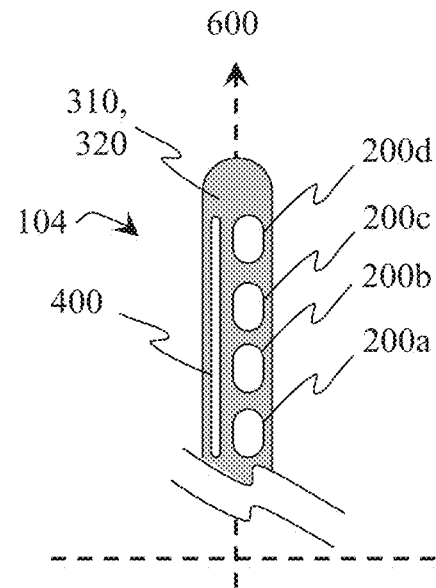
Figure 4C:
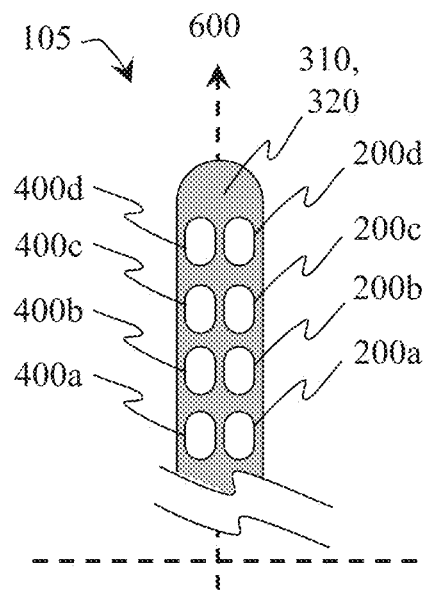

FIGS. 4A, 4B and 4C depict alternative portions with at least two electrodes 200, 400 configurations suitable for being comprised in an implantable stimulator 100, 101, 102 as described herein.

FIG. 4A depicts an implantable first portion of a further embodiment 103 of a stimulator. Similar to the first portion depicted in FIG. 1C, the first surface 310 comprises:

two electrodes 200*a*, 200*b* of a first type and two electrodes 400*a*, 400*b* of a second type. From proximal to first portion, the order depicted is 200*a*, 400*a*, 200*b*, 400*b*—in other words, each electrode of the first type 200*a*, 200*b* is proximate an electrode of the second type 400*a*, 400*b* and comprised in the same surface 310.

The first portion depicted in FIG. 4A is the same as that depicted in FIG. 1A, except:

the electrodes 200, 400 are extended at angle to the longitudinal axis 600. This may reduce the sensitivity to longitudinal misalignment because the longitudinal locations over which tissue stimulation may be provided are increased.

Additionally or alternatively, the second surface 320 may similarly comprise two electrodes 200*a*, 200*b* of the first type and two electrodes 400*a*, 400*b* of the second type.

As discussed above, each electrode 200*a*, 200*b*, 400*a*, 400*b* may be operated as one or more stimulation electrodes or operated as one or more return electrodes.

FIG. 4B depicts an implantable first portion of a further embodiment 104 of a stimulator. Similar to the first portion depicted in FIG. 1C, the first surface 310 comprises four electrodes. However, in this embodiment 104, the first surface 310 comprises:

four electrodes 200*a*, 200*b*, 200*c*, 200*d* of a first type and an electrode 400 of a second type. From proximal to first portion, the order depicted is 200*a*, 200*b*, 200*c*, 200*d*. Transversely adjacent to the four electrodes of the first type 200 is an electrode of the second type 400, extending longitudinally to be adjacent to each electrode of the first type 200.

Nominally, the electrodes of the first type 200 may be operated as one or more stimulation electrodes. The electrode of the second type 400 may be nominally operated as a return electrode for one or more of the stimulation electrodes.

This may reduce the sensitivity to longitudinal misalignment because the four different longitudinal locations are provided which may be selected for stimulation over which tissue stimulation may be provided are increased.

Additionally or alternatively, the second surface 320 may similarly comprise four electrodes 200*a*, 200*b*, 200*c*, 2003 of the first type and one adjacent and longitudinally extended electrode 400 of the second type.

As discussed above, each electrode 200a, 200b, 200c, 200d, 400 may be operated as one or more stimulation electrodes or operated as one or more return electrodes.

FIG. 4C depicts an implantable first portion of a further embodiment 105 of a stimulator. Similar to the first portion depicted in FIG. 4B, the first surface 310 comprises four electrodes 200a, 200b, 200c, 200d of a first type. However, in this embodiment 105, the first surface 310 further comprises four adjacent electrodes 400a, 400b, 400c, 400d of a second type. From proximal to first portion, the order depicted is 200a/400a, 200b/400b, 200c/400c, 200d/400d. Transversely adjacent to each of the four electrodes of the first type 200 is an electrode of the second type 400 at approximately the same disposition along the longitudinal axis 600.

Nominally, the electrodes of the first type 200 may be operated as one or more stimulation electrodes. The electrodes of the second type 400 may be nominally operated as a return electrode for one or more of the stimulation electrodes. Nominally, adjacent electrodes may be considered as a stimulation/return pair 200/400.

In other words, a 2×4 electrode array is provided—two along a transverse axis and four along the longitudinal axis.

This may reduce the sensitivity to longitudinal misalignment because the four different stimulation/return 200/400 pairs are provided at substantially different longitudinal locations are provided which may be selected for stimulation over which tissue stimulation may be provided are increased.

Additionally or alternatively, the second surface 320 may similarly comprise four electrodes 200a, 200b, 200c, 200d of the first type and four adjacent electrodes 400a, 400b, 400c, 400d of the second type.

As discussed above, each electrode 200a, 200b, 200c, 200d, 400a, 400b, 400c, 400d may be operated as one or more stimulation electrodes or operated as one or more return electrodes. This may also reduce the sensitivity to a transverse misalignment.

The stimulator 100, 101, 102, 103, 104, 105 may further comprise:
an energy receiver, configured and arranged to wirelessly receive energy from an associated energy transmitter when the associated energy transmitter is proximate;
the pulse generator 500 being further configured and arranged to receive electrical energy from the energy receiver for its operation.

The stimulator 100, 101, 102, 103, 104, 105 may be further modified. For example:
the substrate 300 and pulse generator 500 may be embedded in one or more flexible bio-compatible encapsulation layers. These layers may comprise: a Liquid Crystal Polymer (LCP), a Polydimethylsiloxane (PDMS), a silicone polyurethane, a Polyimide, a parylene, a bio-compatible polymer, a biocompatible elastomer, and any combination thereof.

By providing relatively larger higher electrode 200, 400 surfaces, stimulators 100, 101, 102, 103, 104, 105 may be operated at a lower energy/lower power. This may be advantageous in applications where high frequency and/or burst stimulation is used.

High frequency operation may require more energy to be provided by the pulse generator 500. In applications where energy/power is critical (for example, if an increased operating lifetime is desired from a power source for the pulse generator 500), any reduction in required power may be advantageous. High frequency operation may be considered as generating electrical stimulation pulses with a frequency of 1000 Hz or more, preferably 1500 Hz or more, more preferably 2000 Hz or more, yet more preferably 2500 Hz or more.

Experiments with burst stimulation have been performed—for example, Burst Occipital Nerve Stimulation for Chronic Migraine and Chronic Cluster Headache by Garcia-Ortega et al, Neuromodulation 2019; 22: 638-644, DOI: 10.1111/ner.12977.

For burst operation, the pulse generator 500 is further configured and arranged to generate electrical stimulation pulses in groups of stimulation pulses.

For example, groups (or bursts) of stimulation pulses may comprise 2 to 10 pulses, more preferably 2 to 5 stimulation pulses. Stimulation pulses in a group may have, for example, a repetition frequency of more than 500 Hz, typically 1000 Hz or more. Groups may be repeated, for example, at more than 5 Hz, typically 40 Hz or more.

As with high frequency operations, burst operation may require more energy to be provided by the pulse generator 500, and any reduction in required power may be advantageous.

Additionally, the speed of charge-balance recovery may also increase with a lower impedance. By using a relatively thin-foil substrate 300, stimulation between an electrode of the first type 200 comprised in one surface 310, 320 and an electrode of the second type 400 comprised in the other surface 310, 320, the current path in tissue is relatively short, reducing impedance.

Similarly, using a substrate 300, and stimulation between an electrode of the first type 200 comprised in one surface 310, 320 and an adjacent electrode of the second type 400 comprised in the same surface 310, 320, provide a relatively short path through tissue.

The invention encompasses every possible combination of the various features of each embodiment disclosed. One or more of the elements described herein with respect to various embodiments can be implemented in a more separated or integrated manner than explicitly described, or even removed or rendered as inoperable in certain cases, as is useful in accordance with a particular application While the invention has been described with reference to specific illustrative embodiments, modifications and variations of the invention may be constructed without departing from the spirit and scope of the invention as set forth in the following claims.

REFERENCE NUMERALS 100, 101, 102 implantable stimulators
103, 104, 105 further embodiments of implantable stimulators
200a, 200b one or more stimulation electrodes
250 one or more stimulation electrical interconnection layers
300 a substrate
310 a first surface of the substrate
320 a second surface of the substrate
350 a portion of the substrate comprising no stimulation electrodes
400a, 400b one or more return electrodes
500 a pulse generator
600 a longitudinal axis
610 a further portion or a proximal end
630 a first portion or a distal end
700 a first transverse axis
710 a maximum proximal transverse cross-section 730 a maximum distal transverse cross-section
750 a second transverse axis
800 median plane of subject
810 location for left supraorbital nerve or cortical stimulation
820 location for right supraorbital nerve or cortical stimulation
830a first location for left occipital nerve stimulation
830b second location for left occipital nerve stimulation
840a first location for right occipital nerve stimulation
840b second location for right occipital nerve stimulation
850 location for deep brain stimulation
860 location for vagus nerve, carotid artery, carotid sinus, phrenic nerve or hypoglossal stimulation
865 location for cerebral spinal cord stimulation
870 location for peripheral nerve stimulation
875 location for spinal cord stimulation
880 location for gastric stimulation
885 location for sacral & pudendal nerve stimulation
890 location for sacral neuromodulation
895 location for fibular nerve stimulation
910 left supraorbital nerve
920 right supraorbital nerve
930 left greater occipital nerve
940 right greater occipital nerve
1000 subject being treated
1010 forehead of subject
1015 back of subject's head
1020 right ear of subject
1021 left ear of subject
1030 right orbita of subject
1031 left orbita of subject
1035 occipital protuberance inion
1040 vascular structure
1050 mastoid process
1100 (optional) area to be shaved
1200 extent for portion with at least two electrodes—(b) left to (a) right
1210 extent for further portion—(b) left to (a) right
1220 offset from landmark
1250 a first incision
1260 a second incision
1270 a third incision
2001 outer skin layer
2003 nerve tissue
2005 subcutaneous fat
2009 aponeurosis layer
2013 periosteum layer
2015 bone tissue, for example skull
2019 muscle tissue
2050 typical location for occipital nerve stimulation
2055 conventional location for supraorbital nerve stimulation
3000 tissue marker
3010 tissue knife, e.g. a surgical scalpel
3020 blunt scissors/forceps
3030a,b guidewire introducer needle assembly (a, b) comprising a guidewire introducer needle (a) and a removable guidewire introducer mandrin (b)
3040 guide wire
3050a,b first introducer assembly (a, b) comprising a first introducer sheath (a) and a removable first introducer mandrin (b)
3060a,b second introducer assembly (a, b) comprising a second introducer sheath (a) and a removable second introducer mandrin (b)
3070 tweezers, such as silicone-tipped tweezers

The invention claimed is:

1. A method for implanting an implantable stimulator under nerve tissue of a subject, the implantable stimulator comprising:
   a substrate, comprising a first surface and a second surface, wherein a thickness of the substrate is defined by the first and second surfaces; and
   at least two electrodes, located along a conformable first portion of the substrate, the thickness of the substrate along the conformable first portion being equal to or less than 0.5 millimeters;
   the method comprising:
   identifying a target location for stimulation which in transverse cross-section comprises an outer skin layer, nerve tissue to be stimulated, and an inner aponeurosis layer;
   forming one or more incisions proximate the target location;
   introducing the conformable first portion in the skin layers at the target location, whereby the at least two electrodes are disposed (a) under the nerve tissue to be stimulated and (b) above or in the inner aponeurosis layer.

2. The method according to claim 1, the method further comprising:
   introducing the conformable first portion, whereby the at least two electrodes are disposed in the skin layers between subcutaneous fat and the aponeurosis layer.

3. The method according to claim 1, the method further comprising:
   introducing the first portion, whereby the at least two electrodes are disposed in the skin layers directly adjacent to the aponeurosis layer.

4. The method according to claim 1, the method further comprising:
   removing one or more skin layers, including an outer skin layer and subcutaneous fat, before introducing the first portion.

5. The method according to claim 1, the method further comprising:
   forming an incision proximate an implantation location; and
   introducing a further portion of the substrate in the skin layers via the incision proximate an implantation location, whereby the further portion is disposed below at least some subcutaneous fat and above or in muscle tissue.

6. The method according to claim 5, the method further comprising:
   introducing the further portion, whereby the further portion is disposed in the skin layers between subcutaneous fat and a bone layer.

7. The method according to claim 5, the method further comprising:
   introducing the further portion, whereby the further portion is disposed in the skin layers directly adjacent to the muscle tissue.

8. The method according to claim 5, the method further comprising:
   removing one or more skin layers, including an outer skin layer and subcutaneous fat, before introducing the further portion.

9. The method according to claim 5, the implantable stimulator further comprising a pulse energy receiver or pulse generator located along the further portion.

10. The method according to claim 5, wherein the thickness of the substrate along the further portion is 4 millimeters or less.

11. The method according to claim 1, wherein:
the substrate is longitudinally-extended, further comprising a further portion; and
the first portion has a first maximum transverse cross-section and the further portion has a further maximum transverse cross-section, the further maximum transverse cross-section being at least 1.2 times the first maximum transverse cross-section;
the one or more incisions proximate the target location a first incision and a second incision on opposite sides of the target location;
the method further comprising:
introducing a first introducer sheath under the skin from the second incision to the first incision, the first introducer sheath having a maximum internal transverse cross-section less than the further maximum transverse cross-section of the substrate;
introducing the conformable first portion, comprising the at least two electrodes, into the first introducer sheath from the first incision to the second incision;
removing the first introducer sheath, whereby the implantable stimulator extends under the skin from the further portion at the first incision to the conformable first portion at the second incision, whereby the at least two electrodes are arranged to transfer treatment energy to the target location.

12. The method according to claim 11, the method further comprising:
forming a third incision between the first and second incisions;
introducing the first introducer sheath under the skin from the second incision to the third incision instead of from the second incision to the first incision;
introducing a second introducer sheath under the skin from the third incision to the first incision, the second introducer sheath having a maximum internal transverse cross-section less than the further maximum transverse cross-section of the substrate;
introducing the first portion of the implantable stimulator, comprising the at least two electrodes, into the second introducer sheath from the first incision to the third incision position;
removing the second introducer sheath;
introducing the first portion of the implantable stimulator, comprising the at least two electrodes, into the first introducer sheath from the third incision to the second incision; and
removing the first introducer sheath, whereby the implantable stimulator extends under the skin from the further portion at the first incision to the first portion at the second incision.

13. The method according to claim 1, wherein the substrate comprises a first and second surface defining a thickness of the substrate, the thickness of the substrate along the conformable first portion being 0.3 millimeter or less.

14. The method according to claim 1, wherein the conformable first portion is foil-like, comprising two or more adjacent polymeric substrate layers.

15. The method according to claim 1, wherein the conformable portion comprises a Liquid Crystal Polymer (LCP).

16. The method according to claim 1, wherein the substrate comprises a first conformable layer and at least one second conformable layer, wherein a plurality of electrical interconnection layers are positioned along the first layer using a deposition technique, and wherein the at least one second layer is secured to the first layer so as to cover the plurality of electrical interconnections.

17. The method according to claim 1, the method further comprising configuring and arranging the implantable stimulator for stimulating:
one or more nerves, one or more muscles, one or more organs, spinal cord tissue, brain tissue, one or more cortical surface regions, one or more sulci, and any combination thereof.

18. The method according to claim 1, the method further comprising configuring and arranging the implantable stimulator for treatment of:
headaches, primary headaches, incontinence, occipital neuralgia, sleep apnea, hypertension, gastro-esophageal reflux disease, an inflammatory disease, limb pain, leg pain, back pain, lower back pain, phantom pain, chronic pain, epilepsy, an overactive bladder, post-stroke pain, obesity, an autoimmune disorder, rheumatoid arthritis, inflammatory bowel disease, Crohn's disease, and any combination thereof.

19. A method for implanting an implantable stimulator, the implantable stimulator comprising:
a longitudinally-extended substrate having a conformable first portion and a further portion;
at least two electrodes, comprised in the conformable first portion;
wherein the first portion has a first maximum transverse cross-section and the further portion has a further maximum transverse cross-section, the further maximum transverse cross-section being at least 1.2 times the first maximum transverse cross-section;
the method comprising:
identifying a target location of a subject for stimulation;
forming a first and second incision on opposite sides of the target location;
introducing a first introducer sheath under the skin from the second incision to the first incision, the first introducer sheath having a maximum internal transverse cross-section less than the further maximum transverse cross-section of the substrate;
introducing the conformable first portion, comprising the at least two electrodes, into the first introducer sheath from the first incision to the second incision;
removing the first introducer sheath, whereby the implantable stimulator extends under the skin from the further portion at the first incision to the conformable first portion at the second incision whereby the at least two electrodes are arranged to transfer treatment energy to the target location.

20. The method according to claim 19, the method further comprising:
introducing a guide wire under the skin between the first and second incisions, the guide wire having a maximum transverse cross-section less than the minimum internal transverse cross-section of the introducer sheath;
introducing the first introducer sheath over the guide wire under the skin from the second incision to the first incision; and
removing the guidewire, whereby the first introducer sheath extends under the skin from the second incision to the first incision.

21. The method according to claim 19, the method further comprising:

inserting the tip of an guidewire introducer needle into the first incision and further inserting the guidewire introducer needle under the skin until the tip emerges from the second incision, the guidewire introducer needle having a minimum internal transverse cross-section greater than the maximum transverse cross-section of the guide wire;

inserting the guide wire through the guidewire introducer needle; and removing the guidewire introducer needle from under the skin to leave the guide wire extending under the skin through the first incision to the second incision.

22. The method according to claim 19, the method further comprising:

forming a skin pocket around the first incision, arranged to accept the further portion of the implantable stimulator; and introducing the further portion of the implantable stimulator into the skin pocket at the first incision.

23. The method according to claim 19, wherein the target location is under nerve tissue of the subject.

24. The method according to claim 19, wherein the implantable stimulator further comprises a pulse energy receiver or pulse generator located along the further portion.

25. The method according to claim 19, wherein the substrate comprises a first and second surface defining a thickness of the substrate, the thickness of the substrate along the further portion is 5 millimeters or less, preferably 4 millimeters or less, even more preferably 3 millimeters or less.

26. The method according to claim 19, the method further comprising:

forming a third incision between the first and second incisions;

introducing the first introducer sheath under the skin from the second incision to the third incision instead of from the second incision to the first incision;

introducing a second introducer sheath under the skin from the third incision to the first incision, the second introducer sheath having a maximum internal transverse cross-section less than the further maximum transverse cross-section of the substrate;

introducing the first portion of the implantable stimulator, comprising the at least two electrodes, into the second introducer sheath from the first incision to the third incision position;

removing the second introducer sheath;

introducing the first portion of the implantable stimulator, comprising the at least two electrodes, into the first introducer sheath from the third incision to the second incision; and removing the first introducer sheath, whereby the implantable stimulator extends under the skin from the further portion at the first incision to the first portion at the second incision.

27. The method according to claim 19, wherein the target location identified for stimulation comprises, in transverse cross-section, an outer skin layer, nerve tissue to be stimulated, and an inner aponeurosis layer;

the method further comprising:

introducing the conformable first portion in the skin layers at the target location, whereby the at least two electrodes are disposed under the nerve tissue to be stimulated and above or in the aponeurosis layer.

28. A method for implanting an implantable stimulator under nerve tissue of a subject, the implantable stimulator comprising:

a substrate, comprising a first surface and a second surface, wherein a thickness of the substrate is defined by the first and second surfaces;

at least two electrodes, located along a conformable first portion of the substrate, the thickness of the substrate along the conformable first portion being equal to or less than 0.3 millimeters;

wherein the substrate is longitudinally-extended, further comprising a further portion; and a pulse energy receiver or pulse generator located along the further portion;

wherein the thickness of the substrate along the further portion is 4 millimeters or less;

wherein the conformable first portion has a first maximum transverse cross-section and the further portion has a further maximum transverse cross-section, the further maximum transverse cross-section being at least 1.2 times the first maximum transverse cross-section;

wherein the conformable first portion is foil-like, comprising two or more adjacent polymeric substrate layers;

wherein the conformable first portion comprises a Liquid Crystal Polymer (LCP);

wherein a plurality of electrical interconnection layers are positioned along a first of the polymeric substrate layers using a deposition technique, and wherein at least one second of the polymeric substrate layers is secured to the first layer so as to cover the plurality of electrical interconnections;

the method comprising:

identifying a target location for stimulation which in transverse cross-section comprises an outer skin layer, nerve tissue to be stimulated, and an inner aponeurosis layer;

forming a first incision and a second incision on opposite sides of the target location;

introducing a first introducer sheath under the skin from the second incision to the first incision, the first introducer sheath having a maximum internal transverse cross-section less than the further maximum transverse cross-section of the substrate;

forming another incision in line with and outside the first and second incisions;

introducing a second introducer sheath under the skin from the first incision to the another incision, the second introducer sheath having a maximum internal transverse cross-section less than the further maximum transverse cross-section of the substrate;

introducing the conformable first portion of the implantable stimulator, comprising the at least two electrodes, into the second introducer sheath from the another incision to the first incision;

removing the second introducer sheath;

introducing the conformable first portion of the implantable stimulator, comprising the at least two electrodes, into the first introducer sheath from the first incision to the second incision; and removing the first introducer sheath, whereby the implantable stimulator extends under the skin from the further portion at the another incision to a tip of the conformable first portion at the second incision, whereby the at least two electrodes are arranged under the nerve tissue to be stimulated and between subcutaneous fat and the aponeurosis layer, directly adjacent to the aponeurosis layer;

removing one or more skin layers, including an outer skin layer and subcutaneous fat, before introducing the conformable first portion;

forming an incision proximate an implantation location;

introducing the further portion of the substrate in the skin layers via the incision proximate the implantation location, whereby the further portion is disposed below at least some subcutaneous fat, directly adjacent to and above or in muscle tissue, and between subcutaneous fat and a bone layer;

removing one or more skin layers, including an outer skin layer and subcutaneous fat, before introducing the further portion; and configuring and arranging the implantable stimulator for stimulating one or more nerves for treatment of headaches.

\* \* \* \* \*